United States Patent
Roth et al.

(10) Patent No.: US 9,675,663 B2
(45) Date of Patent: Jun. 13, 2017

(54) TUSC2 THERAPIES

(71) Applicant: Board of Regents, The University of Texas System, Austin, TX (US)

(72) Inventors: Jack Roth, Houston, TX (US); David Stewart, Ottawa (CA); Charles Lu, Houston, TX (US); Ignacio I. Wistuba, Houston, TX (US); Shaoyu Yan, Pearland, TX (US); Maria I. Nunez, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/480,341

(22) Filed: Sep. 8, 2014

(65) Prior Publication Data
US 2014/0377339 A1   Dec. 25, 2014

Related U.S. Application Data

(62) Division of application No. 13/410,811, filed on Mar. 2, 2012, now abandoned.

(60) Provisional application No. 61/448,463, filed on Mar. 2, 2011, provisional application No. 61/472,530, filed on Apr. 6, 2011, provisional application No. 61/513,244, filed on Jul. 29, 2011, provisional application No. 61/603,686, filed on Feb. 27, 2012.

(51) Int. Cl.
| | |
|---|---|
| *A61K 38/17* | (2006.01) |
| *A61K 9/127* | (2006.01) |
| *A61K 48/00* | (2006.01) |
| *G01N 33/50* | (2006.01) |
| *A61K 31/517* | (2006.01) |
| *C07K 14/47* | (2006.01) |
| *A61K 31/7088* | (2006.01) |
| *A61K 31/7135* | (2006.01) |
| *A61K 39/395* | (2006.01) |
| *A61K 45/06* | (2006.01) |
| *C07K 16/28* | (2006.01) |
| *C07K 16/30* | (2006.01) |
| *A61K 39/00* | (2006.01) |

(52) U.S. Cl.
CPC .......... *A61K 38/1709* (2013.01); *A61K 9/127* (2013.01); *A61K 31/517* (2013.01); *A61K 31/7088* (2013.01); *A61K 31/7135* (2013.01); *A61K 38/17* (2013.01); *A61K 39/3955* (2013.01); *A61K 39/39558* (2013.01); *A61K 45/06* (2013.01); *A61K 48/005* (2013.01); *A61K 48/0033* (2013.01); *C07K 14/47* (2013.01); *C07K 16/2863* (2013.01); *C07K 16/3023* (2013.01); *G01N 33/5011* (2013.01); *A61K 2039/505* (2013.01); *G01N 2510/00* (2013.01); *G01N 2800/52* (2013.01)

(58) Field of Classification Search
CPC .... A61K 9/127; A61K 38/17; A61K 38/1709; A61K 48/005; G01N 33/5011; G01N 2510/00; G01N 2800/52
USPC .............. 424/93.6, 450, 489; 435/40.5, 375; 436/64; 514/2, 44; 530/350; 536/23.1, 536/23.5
See application file for complete search history.

(56) References Cited

U.S. PATENT DOCUMENTS

| | | | |
|---|---|---|---|
| 7,977,468 B2 | 7/2011 | Ji et al. | ........................ 536/23.1 |
| 2002/0164715 A1* | 11/2002 | Ji | ........................ A01K 67/0271 435/69.5 |
| 2006/0251726 A1* | 11/2006 | Lin | ........................ A61K 9/127 424/489 |
| 2009/0023207 A1 | 1/2009 | Ji et al. | ........................ 435/366 |

OTHER PUBLICATIONS

Ji et al, Cancer Res. 62:2715-2720, 2002.*
Deng et al, Cancer Gene Therapy 15:29-39, 2008.*
Ito et al, Cancer Gene Therapy 11:733-739, 2004.*
Tanaka et al, Lung Cancer 39:289-296, 2003.*
Joseph et al, Ann. N.Y. Acad. Sci. 926:204-216, 2000.*
Pisters et al, Clinical Cancer Res. 10:2587-2593, 2004.*
Deng et al., "Synergistic tumor suppression by coexpression of *FUS1* and *p53* is associated with down-regulation of murine double minute-2 and activation of the apoptotic protease-activating factor 1-dependent apoptotic pathway in human non-small cell lung cancer cells," *Cancer Res.*, 67(2):709-717, 2007.
Ito et al., "Liposomal vector mediated delivery of the 3p *FUS1* gene demonstrates potent antitumor activity against human lung cancer in vivo," *Cancer Gene Ther.*, 11:733-739, 2004.
Ji et al., "3p21.3 tumor suppressor cluster: prospects for translational applications," *Future Oncology*, 1:79-92, 2005.
Ji et al., "Expression of several genes in the human chromosome 3p21.3 homozygous deletion region by an adenovirus vector results in tumor suppressor activities in vitro and in vivo," *Cancer Research*, 62:2715-2720, 2002.
Ji et al., "Tumor suppressor FUS1 signaling pathway," *J Thorac Oncol.*, 3(4):327-330, 2008.
Kanjer et al., "In vivo model for research of breast cancer biomarkers," *Arch Oncol*, 14(3-4):141-145, 2006.
Kawashima et al., "Synergistic inhibition of EGFR tyrosine kinase activity and NSCLC cell growth by combination treatment with FUS1-nanoparticle and gefitinib," *Proc. Amer. Assoc. Cancer Res.*, 46:637, Abstract #2707, 2005.
Kondo et al., "Overexpression of candidate tumor suppressor gene *FUS1* isolated from the 3p21.3 homozygous deletion region leads to G1 arrest and growth inhibition of lung cancer cells," *Oncogene*, 20:6258-6262, 2001.

(Continued)

*Primary Examiner* — Kevin Hill
(74) *Attorney, Agent, or Firm* — Parker Highlander PLLC

(57) ABSTRACT

A method for predicting a subject's response to a TUSC2 therapy is provided. In particular, a subject's response is predicted based on the proportion of cancers cells that are apoptotic. Also provided is a method of treating a subject previously predicted to have a favorable response with a TUSC2 therapy. Methods for treating cancer by administration of a TUSC2 therapeutic in conjunction with an EGFR inhibitor and/or a protein kinase inhibitor are also disclosed. Kits and reagents for use in TUSC2 therapy are provided.

21 Claims, 30 Drawing Sheets

(56) References Cited

OTHER PUBLICATIONS

Lu et al., "Phase I clinical trial of systemically administered *TUSC2(FUS1)*-nanoparticles mediating functional gene transfer in humans," *PLoS One*, 7(4):e34833, 2012.
Nagler et al., "Squamous cell carcinoma of the tongue: the prevalence and prognostic roles of p53, Bcl-2, c-erbB-2 and apoptotic rate as related to clinical and pathological characteristics in a retrospective study," *Cancer Letters*, 186:137-150, 2002.
Office Action issued in U.S. Appl. No. 13/410,811, mailed Aug. 14, 2013.
Office Action issued in U.S. Appl. No. 13/410,811, mailed Feb. 7, 2014.
Office Action issued in U.S. Appl. No. 13/410,811, mailed Jun. 9, 2014.
Office Action issued in U.S. Appl. No. 13/410,811, mailed May 28, 2013.
PCT International Preliminary Report on Patentability issued in International Application No. PCT/US2012/027529, mailed Sep. 12, 2013.
PCT Invitation to Pay Additional Fees issued in International Application No. PCT/US2012/027529, mailed May 7, 2012.
PCT Search Report and Written Opinion issued in International Application No. PCT/US2012/027529, mailed Jul. 6, 2012.
Prudkin et al., "Loss and reduction of Fus1 protein expression is a frequent phenomenon in the pathogenesis of lung cancer," *Clin Cancer Res.*, 14(1):41-47, 2008.
Pu et al., "PI3K/PTEN/AKT/mTOR pathway genetic variation predicts toxicity and distant progression in lung cancer patients receiving platinum-based chemotherapy," *Lung Cancer*, 71:82-88, 2011.
Qiu et al., "In vitro enzymatic characterization of near full length EGFR in activated and inhibited states," *Biochemistry*, 48:6624-6632, 2009.
Ramesh et al., "Successful treatment of primary and disseminated human lung cancers by systemic delivery of tumor suppressor genes using an improved liposome vector," *Mol. Ther.*, 3:337-350, 2001.
Sakai et al., "Enhanced sensitivity of tumor cells to the EGFR/VEGFR inhibitor ZD6474 by FUS1 and FHIT-nanoparticle-mediated gene therapy in human lung cancer," *Proceedings of the American Association for Cancer Research Annual Meeting*, 50:669, Abstract #2772, 2009.
Sakai et al., "Overcoming drug resistance to EGFR-tyrosine kinase inhibitors by FUS1 or FHIT-gene therapy in human lung cancer," *Proceedings of the American Association for Cancer Research Annual Meeting*, 51:882, 2010.
Scott et al., "A histopathological assessment of the response of rectal adenocarcinoma to combination chemo-radiotherapy: relationship to apoptotic activity, p53 and bcl-2 expression," *Eur. J. Surg. Oncol.*, 24:169-173, 1998.
Stewart et al., "Exponential decay nonlinear regression analysis of patient survival curves: preliminary assessment in non-small cell lung cancer," *Lung Cancer*, 71:217-223, 2011.
Uno et al., "Myristoylation fo the Fus1 protein is required for tumor suppression in human lung cancer cells," *Cancer Res.*, 64:2969-2976, 2004.
Wu et al., "The Src-PI3K-Akt and apoptosis signaling pathway-targeted therapy with novel pro-apoptotic FUS1-nanoparticles and Src kinase inhibitors for lung cancer," *Proceedings of the American Association for Cancer Research Annual Meeting*, 50:682, Abstract #2823, 2009.
Hoffman-Luca et al., "Significant differences in the development of acquired resistance to the MDM2 inhibitor SAR405838 between in vitro and in vivo drug treatment," *PLoS One*, 10(6):e0128807, 2015.

\* cited by examiner

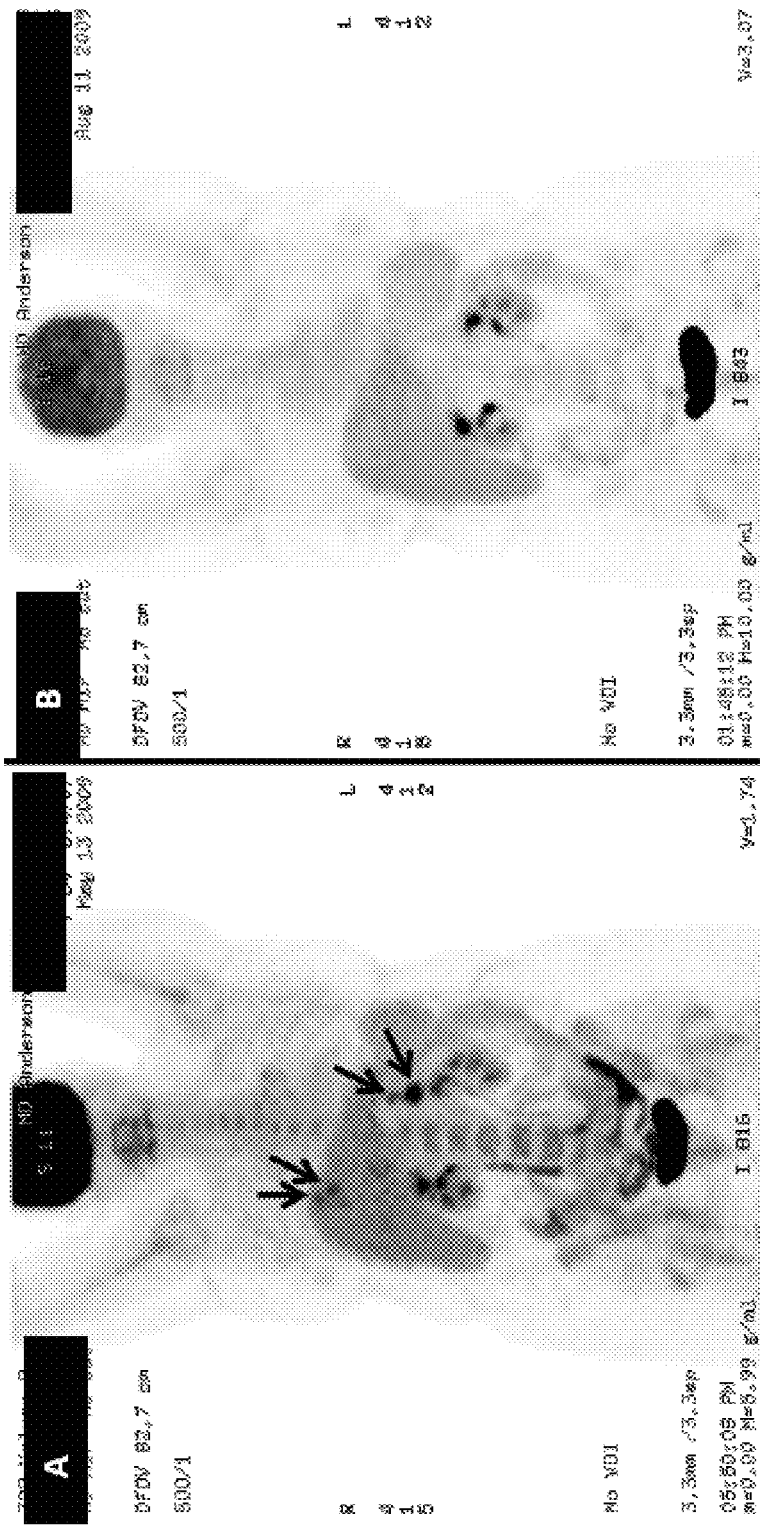
FIG. 3A-B

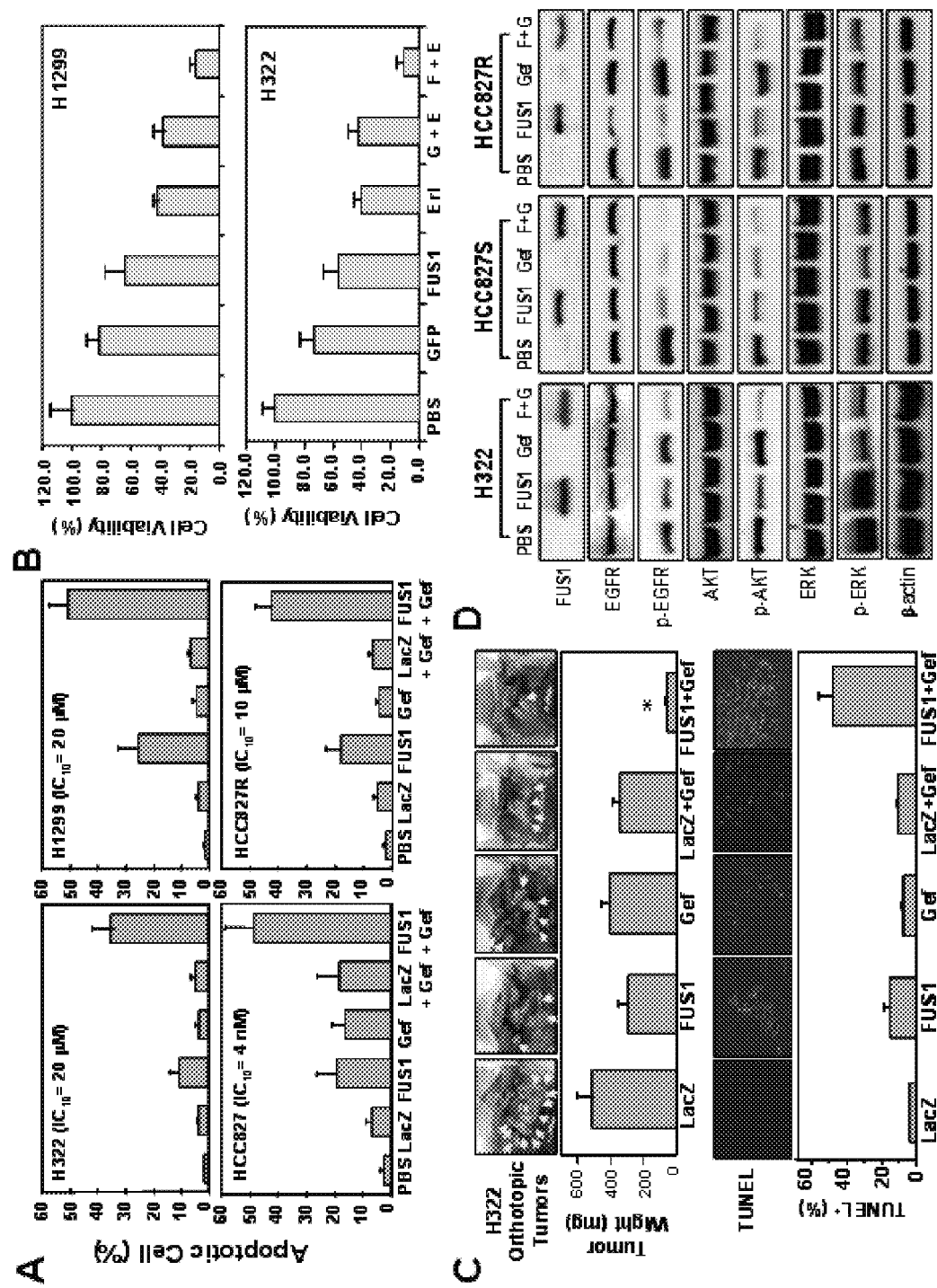
FIG. 12A-D

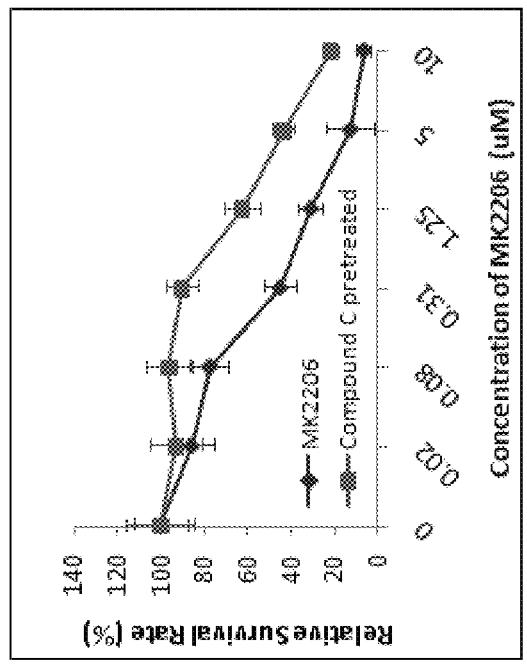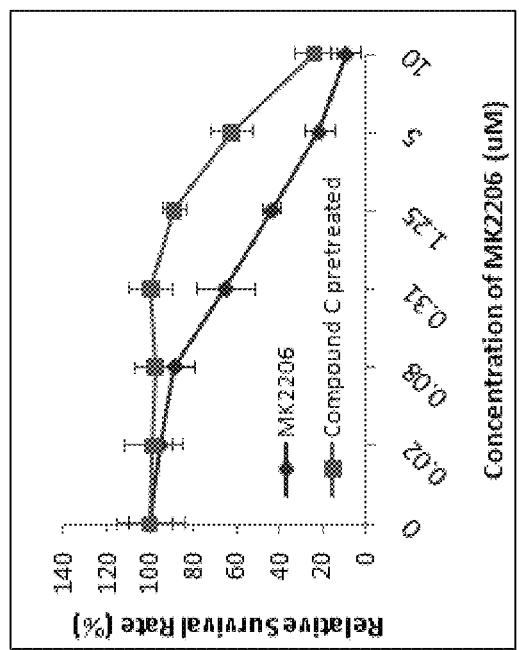
FIG. 23

TUSC2 THERAPIES

This application is a divisional of U.S. application Ser. No. 13/410,811, filed Mar. 2, 2012, which claims the benefit of U.S. Provisional Patent Application Nos. 61/448,463, filed Mar. 2, 2011; 61/472,530, filed Apr. 6, 2011; 61/513,244, filed Jul. 29, 2011; and 61/603,686, filed Feb. 27, 2012, each of which is incorporated herein by reference in its entirety.

This invention was made with Government support under grant nos. CA-016672, CA-070907 and CA-113450 awarded by the National Institutes of Health. The Government has certain rights in the invention.

BACKGROUND OF THE INVENTION

1. Field of the Invention

The present embodiments provided herein relate generally to the fields of molecular biology and cancer therapies.

2. Description of Related Art

As the molecular and genetic mechanisms of oncogenesis become better elucidated, the focus of cancer therapy has shifted from the tissue to the genetic level (Bishop, 1991). Mutations in two major classes of genes, oncogenes and tumor suppressor genes (TSGs), play central roles in the oncogenic process. TSGs appear to require homozygous deletion or mutation for inactivation, and restoration of TSG expression is feasible in human tumors (Lowe et al., 2004; Roth, 2006). Intratumoral injection of retroviral or adenoviral vectors expressing the wildtype TSG p53 have been performed in patients with locally advanced non-small cell lung cancer and head and neck cancer (Swisher et al., 1999; Roth et al., 1996; Clayman et al., 1998). These studies have demonstrated that viral vectors expressing the TSG p53 can be safely injected into tumors repetitively and can mediate tumor regression. However, because of the systemic immune response, current viral vectors are limited to intratumoral administration, which does not have an effect on tumor metastases, the primary cause of cancer-related death. Thus development of therapies for intravenous, systemic TSG replacement would represent a significant advance.

Homozygous deletions in the 3p21.3 region in lung cancer cell lines and primary lung tumors have lead to the identification of multiple genes with tumor suppressor activity from this region (Lerman et al., 2000).

SUMMARY OF THE INVENTION

In a first embodiment, there is provided a method for predicting a response to a TUSC2 (also known as FUST) therapy in a subject having a cancer, wherein the subject is being evaluated as a candidate for TUSC2 therapy, comprising assessing apoptosis in cancer cells of the subject, wherein if 10% or more of the cancer cells are apoptotic, then the subject is predicted to have a favorable response to TUSC2 therapy. For example, in certain aspects, the subject is predicted to have a favorable response to a TUSC2 therapy if at least 20%, 25%, 30%, 35%, 40%, 45%, 50%, 60% or more of the cancer cells are apoptotic. Conversely, in certain aspects, if fewer than 10% of the cancer cells the subject are apoptotic (e.g., 9%, 8%, 7%, 6%, 5%, 4%, 3%, 2%, 1%, or less), the subject is predicted to have a poor response to the TUSC2 therapy. For example, a favorable response to TUSC2 therapy can comprise a reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, or increased patient survival.

In a further embodiment there is provided a method of selecting a subject having a cancer for a TUSC2 therapy comprising assessing apoptosis in cancer cells of the subject, wherein if 10% or more of the cancer cells are apoptotic, then the subject is selected for the TUSC2 therapy. For example, in certain aspects, the subject is selected for a TUSC2 therapy if at least 20%, 25%, 30%, 35%, 40%, 45%, 50%, 60% or more of the cancer cells are apoptotic. On the other hand, if fewer than 10% of the cancer cells the subject are apoptotic (e.g., 9%, 8%, 7%, 6%, 5%, 4%, 3%, 2%, 1%, or less), the subject is not selected for the TUSC2 therapy.

In certain embodiments, assessing apoptosis in cancer cells or a sample of cancer cells comprises testing the cells for a marker of apoptosis. A variety of apoptotic markers are known in the art and can be used to assess apoptosis in cancer cells. For example, apoptosis can be assessed by testing for caspase activation, membrane blebbing, loss of mitochondrial membrane integrity, or DNA fragmentation. Various techniques may be used for testing cells to assess apoptosis and the testing method will depend upon the marker that is being used. For example, testing for apoptosis may comprise performing an ELISA, an immunoassay, a radioimmunoassay (RIA), an immunoradiometric assay, a fluoroimmunoassay, a chemiluminescent assay, a bioluminescent assay, a gel electrophoresis, a Western blot analysis, a southern blot, flow cytometry, in situ hybridization, positron emission tomography (PET), single photon emission computed tomography (SPECT) imaging or a microscopic assay. Thus, in certain aspects, cancer cells are tested for an apoptotic marker in vivo (e.g., by PET or SPECT imaging).

In certain embodiments, testing cells for a marker of apoptosis comprises contacting the cancer cells with a reagent that labels cells comprising a marker of apoptosis. Examples of reagents that can be used to label apoptotic cells include, but are not limited to, antibodies, small molecules, stains, enzymes nucleic acid probes and aptamers. For instance, in certain cases, apoptosis may be assessed by detecting DNA fragmentation, such as by terminal deoxynucleotidyl transferase (TdT)-mediated dUTP nick end labeling (TUNEL). In this case a subject would be predicted to have a favorable response to a TUSC2 therapy, if 10% or more of the cancer cells in a sample from the patient are TUNEL positive.

The types of cancer cell samples that are assessed for apoptosis will depend upon the type of cancer involved. For example, in the case of a cancer that presents as one or more solid tumor, the sample may be tumor biopsy sample from a primary cancer site or a metastatic site. Cancer cells may also be comprised in other body samples, such as, serum, stool, urine and sputum. In certain aspects, wherein a sample comprises a large number of non-cancer cells, assessing cancer cells for apoptosis may additionally comprise identifying the cancer cells and assessing the identified cancer cells for apoptosis.

In a further embodiment, there is provided a method for treating a subject having a cancer, wherein it was previously determined (or previously estimated) that at least 10% of the cells of said cancer are apoptotic, the method comprising administering a TUSC2 therapy to the subject. For example, in certain aspects, at least 20%, 25%, 30%, 35%, 40%, 45%, 50%, 60% or more of the cancer cells of the subject were previously determined to be apoptotic. As used herein a TUSC2 therapy can be any type of therapy that provides or causes expression of a TUSC2 polypeptide in a cancer cell (see, e.g., U.S. Pat. No. 7,902,441, incorporated herein by reference). For example, a TUSC2 therapy may comprise delivery of a TUSC2 polypeptide or TUSC2 expression vector to cancer cell. A therapy may, for instance, be delivered via nanoparticles, or in the case of nucleic acid expression vectors, through the use of a viral vector.

In certain embodiments, administration of a TUSC2 therapy comprises administration of a TUSC2 expression vector, such a DNA plasmid encoding TUSC2. An expression vector for use according to the embodiments provided herein will generally comprise control elements for the expression of the TUSC2 coding sequence. For example, a vector can comprise a promoter and enhancer element that are effective for expression in cancer cell of interest. In certain aspects, for instance, TUSC2 expression is provided by a CMV promoter or recombinant version thereof, such as the CMV promoter construct described in U.S. Patent Publn. No. 20070092968, incorporated herein by reference. In certain embodiments, a vector provided herein comprises a modified CMV promoter. In certain embodiments, a vector provided herein comprises a mini-CMV promoter. Additional expression control elements can be included such as, for example, an intron, a drug response element, a RNA stabilizing or destabilizing sequence, a cellular localization signal, a polyadenylation signal sequence and/or an optimized translation start codon. Plasmid DNA vectors may also comprise sequences that help facilitate DNA production, such as, a bacterial origin of replication and/or a drug resistance marker. In certain specific aspects, the TUSC2 expression vector is the pLJ143/KGB2/FUS1 plasmid (SEQ ID NO: 1).

Methods for delivery of an expression vector to cells (e.g., in vivo delivery) are well known in the art and include, without limitation, nanoparticles (e.g., liposome nanoparticles), lipid conjugates and viral vectors. In certain aspects, a TUSC2 expression vector is administered in a nanoparticle, such as N-[1-(2,3-dioleoyloxy)propyl]-N,N,N-trimethylammonium chloride (DOTAP):cholesterol liposome nanoparticle. A skilled artisan will recognize that various properties of liposomes can be adjusted to optimize vector delivery. For example, the liposomes may be adjusted to have a certain size range and/or a particular ratio of DNA to lipid; DNA to cholesterol; or lipid to cholesterol. For instance, in the case of a DOTAP:cholesterol liposome, the DOTAP:cholesterol ratio can be defined as between about 1.5:1 and 1:1.5, such as about 10:9. In further aspects, a TUSC2 expression vector is provided in a liposome nanoparticle, wherein the nanoparticles comprise an average particle size of between about 50 and about 500 nm (e.g., 200-500 nm). In still further aspects, a TUSC2-nanoparticle formulation can be defined by their optical density (OD), such as having $OD_{400}$ of between about 0.65 and 0.95.

In still further embodiments a TUSC2 therapy can comprise administration of a TUSC2 polypeptide. Methods for administration of TUSC2 polypeptide are described for example in U.S. Publn. Nos. 20060251726 and 20090023207, incorporated herein by reference. A TUSC2 polypeptide may be modified to enhance its activity and/or ability to enter cancer cells. For instance, the polypeptide can be modified with a lipid moiety (e.g., myristoylated). In certain aspects a TUSC2 in provided as a nanoparticle (e.g., a lipid-based nanoparticle) such as, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube.

A TUSC2 therapy according to the embodiments provided herein is typically formulated in a pharmaceutically acceptable carrier. Such a therapy may be delivered, for example, intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, via inhalation (e.g. aerosol inhalation), by injection or by infusion, and the route of delivery can depend upon the type of cancer to be treated. For example, a TUSC2 expression vector complexed with DOTAP:cholesterol liposome can be administer via intravenous infusion. In certain specific aspects, a TUSC2 therapy is administered intravenously in a dose of from about 0.01 mg/kg to about 0.10 mg/kg, such as a dose of about 0.02, 0.03, 0.04, 0.05, 0.06, 0.07, 0.08 0.09 or 0.10 mg/kg. In further aspects, a TUSC2 therapy, can be administer two or more times (e.g., 3, 4, 5, 6, 7, 8, 9 or 10 times). The timing between doses of such a therapy can be varied and can include, without limitation, about 1, 2 or 3 days, about 1, 2, or 3 weeks or 1 month or more between doses.

In yet a further embodiment, there is provided a method for treating a subject having a cancer, comprising administering a TUSC2 therapy to the subject in conjunction with one or more anti-inflammatory agent. For example, the anti-inflammatory agent may be administered before, after or during a TUSC2 therapy. In a further aspects, more than one anti-inflammatory agent is administered, such as administration of an antihistamine and a corticosteroid. Thus, in certain specific aspects the anti-inflammatory for use in conjunction with a TUSC2 therapy is diphenhydramine and/or dexamethasone.

In certain embodiments, a cancer for treatment or assessment may present as a tumor, such as primary or metastatic tumor. A cancer may be an early stage cancer, or may be a metastatic or late stage cancer. In certain aspects, the cancer is an oral cancer, oropharyngeal cancer, nasopharyngeal cancer, respiratory cancer, a urogenital cancer, a gastrointestinal cancer, a central or peripheral nervous system tissue cancer, an endocrine or neuroendocrine cancer, a hematopoietic cancer, a glioma, a sarcoma, a carcinoma, a lymphoma, a melanoma, a fibroma, a meningioma, brain cancer, oropharyngeal cancer, nasopharyngeal cancer, renal cancer, biliary cancer, prostatic cancer, pheochromocytoma, pancreatic islet cell cancer, a Li-Fraumeni tumor, thyroid cancer, parathyroid cancer, pituitary tumors, adrenal gland tumors, osteogenic sarcoma tumors, multiple neuroendrcine type I and type II tumors, breast cancer, lung cancer (e.g., a non-small cell lung cancer (NSCLC) or small cell lung cancer (SCLC)), head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In further aspects a cancer may be defined as a cancer that is resistant to one or more anticancer therapy, such a chemotherapy resistant cancer. For example, the cancer may be a cancer that is resistant to a platinum-based chemotherapeutic, such as cisplatin.

In further embodiments, a method provided herein further comprises administering at least a second anticancer therapy. For example, a method can comprise treating a subject having a cancer, wherein it was previously determined that at least 10% of the cells of said cancer are apoptotic, comprising administering a TUSC2 therapy and at least a second anticancer agent to the subject. The second anticancer therapy may be, without limitation, a surgical therapy, chemotherapy (e.g., administration of a protein kinase inhibitor or a EGFR-targeted therapy), radiation therapy, cryotherapy, hyperthermia treatment, phototherapy, radioablation therapy, hormonal therapy, immunotherapy, small molecule therapy, receptor kinase inhibitor therapy, anti-angiogenic therapy, cytokine therapy or a biological therapies such as monoclonal antibodies, siRNA, antisense oligonucleotides, ribozymes or gene therapy. Without limitation the biological therapy may be a gene therapy, such as tumor suppressor gene therapy, a cell death protein gene therapy, a cell cycle regulator gene therapy, a cytokine gene therapy, a toxin gene therapy, an immunogene therapy, a suicide gene therapy, a prodrug gene therapy, an anti-cellular proliferation gene therapy, an enzyme gene therapy, or an anti-angiogenic factor gene therapy.

In still a further embodiments provided herein is a kit comprising a TUSC2 therapeutic. For example, in some aspects, a kit provided herein comprises a TUSC2 therapeutic and a reagent for testing cells for a marker of apoptosis, such as a TUNEL reagent. In further aspects, a kit comprises a TUSC2 therapeutic and one or more anti-inflammatory agents. In still further aspects the kit may comprise one more additional components including, but not limited to, a reagent for assessing apoptosis in a cell sample, an anti-inflammatory agent, pharmaceutically acceptable dilution agent, a syringe, an infusion bag, an infusion line, and/or a set of instruction for use of the kit.

In yet a further embodiment provided herein are compositions, therapies, and methods for treating a subject having a cancer, comprising administering to the subject a TUSC2 therapy (e.g., a TUSC2 polypeptide or a TUSC2 expression vector) in conjunction with a second anticancer agent, such as a chemotherapeutic. For example, the chemotherapeutic can be a protein kinase inhibitor, such as a Src or Akt kinase inhibitor. In some aspects, the chemotherapeutic is a epidermal growth factor receptor (EGFR) inhibitor.

In certain embodiments, a method is provided for treating a subject having a cancer, comprising administering to the subject a TUSC2 therapy in conjunction with a protein kinase inhibitor. For instance, the TUSC2 therapy can be administered, before, after or essentially concomitantly with the protein kinase inhibitor. Thus, in some embodiments, a composition is provided comprising a TUSC2 therapeutic and a protein kinase inhibitor in a therapeutically effective amount to treat a cancer. Protein kinase inhibitors for use according to the embodiments include, without limitation, EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. For example, the protein kinase inhibitor can be Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016, or a mixture thereof. In certain aspects, the protein kinase inhibitor is an AKT inhibitor (e.g., MK-2206, GSK690693, A-443654, VQD-002, Miltefosine or Perifosine).

EGFR-targeted therapies for use in accordance with the embodiments include, but are not limited to, inhibitors of EGFR/ErbB1/HER, ErbB2/Neu/HER2, ErbB3/HER3, and/or ErbB4/HER4. A wide range of such inhibitors are known and include, without limitation, tyrosine kinase inhibitors active against the receptor(s) and EGFR-binding antibodies or aptamers. For instance, the EGFR inhibitor can be gefitinib, erlotinib, cetuximab, matuzumab, panitumumab, AEE788; CI-1033, HKI-272, HKI-357 or EKB-569. In certain embodiments, the compositions and therapies provided herein are administered systemically or locally. In one embodiment, the compositions and therapies provided herein are administered systemically. In certain aspects, an EGFR inhibitor is administered to a patient before, after or essentially concomitantly with a TUSC2 therapy. For example, the therapies may be co-administered, such as by co-administration in an intravenous infusion. In certain embodiments, TUSC2 and EGFR inhibitors can be administered in any amount effective to treat cancers. In certain embodiments, the compositions, therapies, and methods provided herein comprise administering TUSC2 and EGFR inhibitors in lower doses than either composition administered alone. In certain embodiments, the compositions, therapies, and methods comprise administering TUSC2 and EGFR inhibitors in lower doses that reduce side effects. In certain embodiments, the compositions, therapies, and methods comprise administering TUSC2 and EGFR inhibitors in doses effective to provide additive, cooperative, or synergistic effect than that provided by either composition administered alone. In certain aspects, cancers for treatment with such therapies can be any of those described herein, such as lung cancers (e.g., non-small cell lung cancer). In certain preferred aspects, a cancer for treatment with a combination therapy is an EGFR-expressing cancer. In certain embodiments, the EGFR-expressing cancer comprises at least 1%, 5%, 10%, 15%, 20%, 25%, 30%, 35%, 40%, 45%, 50%, 55%, 65%, 70%, 75%, 80%, 85%, 90%, 95%, 96%, 97%, 98%, or 99% tumor cells expressing EGFR.

In yet still a further embodiment provided herein is a method for treating a subject having a cancer, wherein it was previously determined that the cancer expresses an EGFR, the method comprising administering to the subject a TUSC2 therapy in conjunction with a EGFR inhibitor. In certain embodiments, provided herein is a method for treating a subject having a cancer comprising the step of determining whether the cancer expresses an EGFR, and administering to the subject a TUSC2 and an EGFR inhibitor. Methods for assessing the EGFR-expression status of a cancer have been described, for example in U.S. Patent Publn. No. 20110052570, incorporated herein by reference. In certain aspects, the EGFR-expressing cancer can be a cancer that expresses a mutant EGFR, such as a cancer expressing an EGFR having a L858R and/or T790M mutation. In certain embodiments, the compositions and therapies provided herein are administered to the patient that have an EGFR-expressing cancer that comprises at least 1%, 5%, 10%, 15%, 20%, 25%, 30%, 35%, 40%, 45%, 50%, 55%, 65%, 70%, 75%, 80%, 85%, 90%, 95%, 96%, 97%, 98%, or 99% tumor cells expressing EGFR. In still further aspects, the subject for treatment has a cancer that was previously determined to express an EGFR and in which at least 10% of the cells of the cancer are apoptotic. In certain embodiments, the methods provided herein further comprise determining whether at least 10%, 15%, 20%, 25%, 30%, 35%, 40%, 45%, 50%, 55%, 65%, 70%, 75%, 80%, 85%, 90%, 95%, 96%, 97%, 98%, or 99% of the cells of the EGFR-expressing cancer are apoptotic.

It is contemplated that any method or composition described herein can be implemented with respect to any other method or composition described herein. Likewise, aspects of the present embodiments discussed in the context of a method for treating a subject are equally applicable to a method of predicting response in a subject and vise versa.

The use of the word "a" or "an" when used in conjunction with the term "comprising" in the claims and/or the specification may mean "one," but it is also consistent with the meaning of "one or more," "at least one," and "one or more than one."

Certain aspects of the embodiments concern selecting a subject having a cancer for a TUSC2 therapy or for predicting a response to a TUSC2 therapy in a subject. In this context, "a poor response" to a TUSC2 therapy means that administration of a TUSC2 therapy, either alone or in combination with a further anticancer agent, is predicted to result in no significant treatment of a cancer (e.g., as measured by reduction of tumor mass, number of metastases, or rate of cancer cell proliferation) or symptoms of a cancer. On the other hand, "a favorable response" means that administration of a TUSC2 therapy, either alone or in combination with a further anticancer agent, is predicted to result in significant treatment of a cancer (e.g., as measured by reduction of tumor mass, number of metastases, or rate of cancer cell proliferation) or cancer symptoms. For example, a favorable response can be a significantly increased period of relapse-free remission in a subject.

Other objects, features and advantages of the present embodiments will become apparent from the following detailed description. It should be understood, however, that the detailed description and the specific examples, while indicating specific embodiments provided herein, are given by way of illustration only, since various changes and modifications within the spirit and scope of the present embodiments will become apparent to those skilled in the art from this detailed description.

BRIEF DESCRIPTION OF THE DRAWINGS

The following drawings form part of the present specification and are included to further demonstrate certain aspects of the present embodiments. The present embodiments may be better understood by reference to one or more of these drawings in combination with the detailed description of specific embodiments presented herein.

FIG. 1A, A schematic representation of a the TUSC2 expression vector pLJ143/KGB2/FUS1 (SEQ ID NO: 1). FIG. 1B, Change in apoptosis pathway mRNAs analyzed in pre- and post-treatment biopsy specimens from patient 31 using SA Apoptosis Signaling Nano-scale PCR Array. Genes in post-treatment samples that differed from pretreatment controls by >3 fold are shown as a scatter plot of log 10 post-treatment values vs log 10 pretreatment values. Factors for which mRNA expression increased >3-fold post treatment appear above the line, while those that decreased by >3 fold appear below the line. Exogenous TUSC2 mRNA expression was detected in the post-treatment biopsy from this patient. FIG. 1C, Canonical apoptosis pathway gene expression pertubations following TUSC2-nanoparticle treatment as detected by SA PRC Array and IPA Analysis. Molecules are represented as nodes, and the biological relationship between two nodes is represented as an edge (Line). The asterisks indicate up-(single asterisk) or down-(double asterisk) regulation. Nodes are displayed using various shapes that represent the functional class of the gene products. Edges are displayed with various labels that describe the nature of the relationship between the nodes (e.g., P for phosphorylation, T for transcription). The identified nodes indicate perturbation of elements of the intrinsic and extrinsic apoptotic pathways following treatment with DOTAP:chol-TUSC2.

FIG. 2A, In situ Proximity Ligation Assay (PLA) for TUSC2 protein in tumor biopsies. A synthetic oligopeptide (GASGSKARGLWPFASAA; SEQ ID NO: 2) derived from the N-terminal amino-acid sequence of the TUSC2 protein was used to develop the anti-TUSC2 polyclonal antibody in rabbits used in this study. Red denotes TUSC2 positivity. DAPI nuclear staining is blue. All panels represent overlays of TUSC2 antibody and DAPI staining Detailed methods are provided in the Supplementary Methods. Pre- and post-treatment biopsies from patients 13, 26, and 31 were tested. Magnification is ×40. Panels: (1) anti-TUSC2 antibody; (2) anti-TUSC2 antibody pre-absorbed with non-specific control peptide (NSP); (3) anti-TUSC2 antibody pre-absorbed with TUSC2 peptide (FP); (4) non-specific control antibody; (5) hematoxylin and eosin. FIG. 2B, Quantitation of PLA signals for pre- and post-treatment samples from patients 13, 26, and 31. The anti-TUSC2 antibody was tested under the conditions described in A). The upper panels show PLA signals from the respective patient biopsies as detected by the anti-TUSC2 antibody with 400× magnification. The lower panel presents quantitative comparisons of six independent fields from each biopsy treated under the specified conditions. TUSC2 expression was significantly increased in post-treatment samples compared to pretreatment samples. TUSC2 expression was not significantly altered by anti-TUSC2 antibody pre-absorption with non-specific control peptide (NSP), but was significantly decreased by pre-absorption with TUSC2 peptide (FP). * $p<0.05$ compared to corresponding pretreatment sample; ■ $p<0.05$ compared to post-treatment samples unabsorbed or pre-absorbed with NSP. All comparisons are by two-tailed unpaired Student's t-test assuming equal variances as determined by F test.

FIG. 3A-B: DOTAP:chol-TUSC2 metabolic tumor response in a metastatic lung cancer patient. The patient is a 54 year old female with a large cell neuroendocrine carcinoma. She had received six prior chemotherapy regimens. Prior to entry in the protocol, two hepatic metastases were progressing on gemcitabine. The patient also had a metastasis in the head of the pancreas and a peripancreatic lymph node (indicated by arrows). FIG. 3A, Pretreatment PET scan. The dose of Fluorodeoxyglucose ($^{18}$F) was 8.8 mCi. FIG. 3B, Post-treatment PET scan performed 20 days following the fourth dose of DOTAP:chol-TUSC2. The dose of Fluorodeoxyglucose ($^{18}$F) was 9.0 mCi. All scans were performed within a 60 to 90 minute window after injection.

FIG. 11A, are results from peripheral blood monocytes (Mo). FIG. 11B, are results from peripheral blood lymphocytes (Ly).

FIG. 12A-D: Effects of combination treatment of FUS1 and gefitinib ("Gef" or "G") and erlotinib ("Erl" or "E") on tumor cell growth and PTK activities in NSCLC cells in vitro and in vivo. FIG. 12A, Effects on induction of apoptosis using TUNEL reaction by FACS. FIG. 12B, Effects of FUS1 and erlotinib on tumor cell growth in resistant H322, H1299. FIG. 12C, Evaluation of therapeutic efficacy and induction of apoptosis by systemic injection of FUS1 nanoparticles and oral administration of gefitinib in human H322 orthotopic lung tumors in nude mice. Fresh frozen tumors were stained for apoptosis by in situ TUNEL staining FIG. 12D, Effects on EGFR, AKT, and ERK activities by western blot analysis.

FIG. 14C, Protein profiles of CMs on ProteinChip Array by SELDI-MS.

FIG. 23: The effect of AMPK inhibitor on FUS1/MK2206-induced cell death. Cell survival was assessed in HCC366 and H322 cells treated with FUS1 nanoparticles and various concentrations of MK2206 in the presence or absence of AMPK inhibitor Compound C. Graphs show relative cell survival (y-axis) at various concentrations of MK2206 (x-axis) with and without AMPK inhibitor as indicated.

DESCRIPTION OF ILLUSTRATIVE EMBODIMENTS

The development of cancer involves the deregulation of number of cellular pathways that control normal cell growth. Crucially, healthy cells express a number of tumor suppressor genes, which act as molecular gatekeepers and prevent uncontrolled cell division. A necessary step in the development of a cancer cells, therefore, is disruption of tumor suppressor signaling pathways. In view of this, one promising avenue for cancer therapy involves expression of tumor suppressor genes in cancer cells to restore normal cellular growth controls. Such therapies may prove less toxic than standard radiation and chemotherapeutic regimes, as normal, noncancerous cells, naturally express the suppressor genes.

Figure 1A:
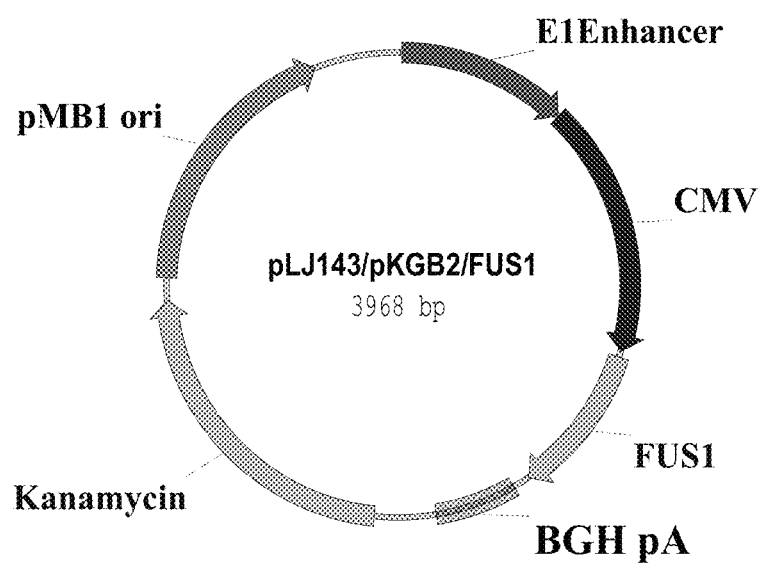
FIG. 1A-C.

The studies detailed herein demonstrate the therapeutic delivery of TUSC2 was safe, resulted in disease stabilization in a number of the study patients and shows promise for clinical effect. In the study, thirty-one human patients were treated at 6 dose levels ranging from 0.01 to 0.09 milligrams per kilogram or DOTAP:chol-TUSC2. The therapy resulted increased expression of TUSC2 in post-treatment tumor specimens but not in pretreatment specimens or peripheral blood lymphocyte controls. Likewise, TUSC2 protein expression was effectively detected in post-treatment tissues and expression was shown to alter the regulation of a number of genes involved in both the intrinsic and extrinsic apoptotic pathways (see, FIG. 1C). Five patients achieved achieving stable disease (2.6-10.8 months, including 2 minor responses). One patient with stable disease had a metabolic response on positron emission tomography (PET) imaging (FIG. 3). Thus, the studies demonstrate the safety of TUSC2 therapy and indicate that the therapy may be effective to improve patient outcome.

Owing to the fact that all cancer cells develop differently, one crucial impediment to anticancer therapy is that certain cancers respond to a given therapy while others prove recalcitrant. Therefore, in order to provide effective therapy, methods are needed to identify subjects that will favorably respond to a given therapy. The studies detailed here demonstrate for the first time effective methods to identify cancer patients who are responders to a TUSC2 therapy regime. Counter intuitively, it has been demonstrated that cancers exhibiting a high proportion of apoptotic cells are more susceptible to therapy. Specifically, patients that respond favorably to the TUSC2 therapy had cancers, wherein about 10% or more of the cells were identified as apoptotic by a TUNEL assay to detect DNA fragmentation (see, e.g., FIG. 5). Accordingly, provided herein is a method for predicting whether a subject will have a favorable response to a TUSC2 therapy by testing the cancer cells of the subject to determine the proportion of the cells that are apoptotic. Likewise, methods for treating subjects who are previously determined to have a cancer with a high proportion (e.g., 10% or greater) of apoptotic cells are provided. These methods will allow for identification and treatment of populations of cancer patients who will likely response to TUSC2 therapies thereby improving the efficacy of the therapy.

Despite the relatively low toxicity exhibited by TUSC2 therapeutics, minor adverse responses were initially noted in the clinical studies described here. It was found, however, that such adverse reactions could be nearly completely ablated by the use of an anti-inflammatory regime in conjunction with the TUSC2 therapy. Specifically, the administration of an antihistamine (diphenhydramine) and a corticosteroid (dexamethasone) immediately preceding and immediately following the TUSC2 administration protected patients from adverse reactions and allowed for higher doses of the TUSC2 therapeutic to be administered. This is an important finding given the possible need to provide higher doses of the therapy for effective clinical benefit. Thus, a methods is provided for treating a patient with a TUSC2 therapeutic comprising administering the therapy in conjunction with one or more anti-inflammatory agent. Accordingly, the two therapies can be included in combined therapeutic regime to increase anti-cancer efficacy. Likewise, when combined the dose of one or both therapies could be reduced while still maintaining effectiveness, thereby potentially reducing the side effects of the combined therapy. Such combined regimes may also show particular effect in specific patient populations, such as those having cancers that are EGFR positive, demonstrate increased apoptotic activity and/or exhibit increased kinase (e.g., AKT) activity.

Figure 26A:
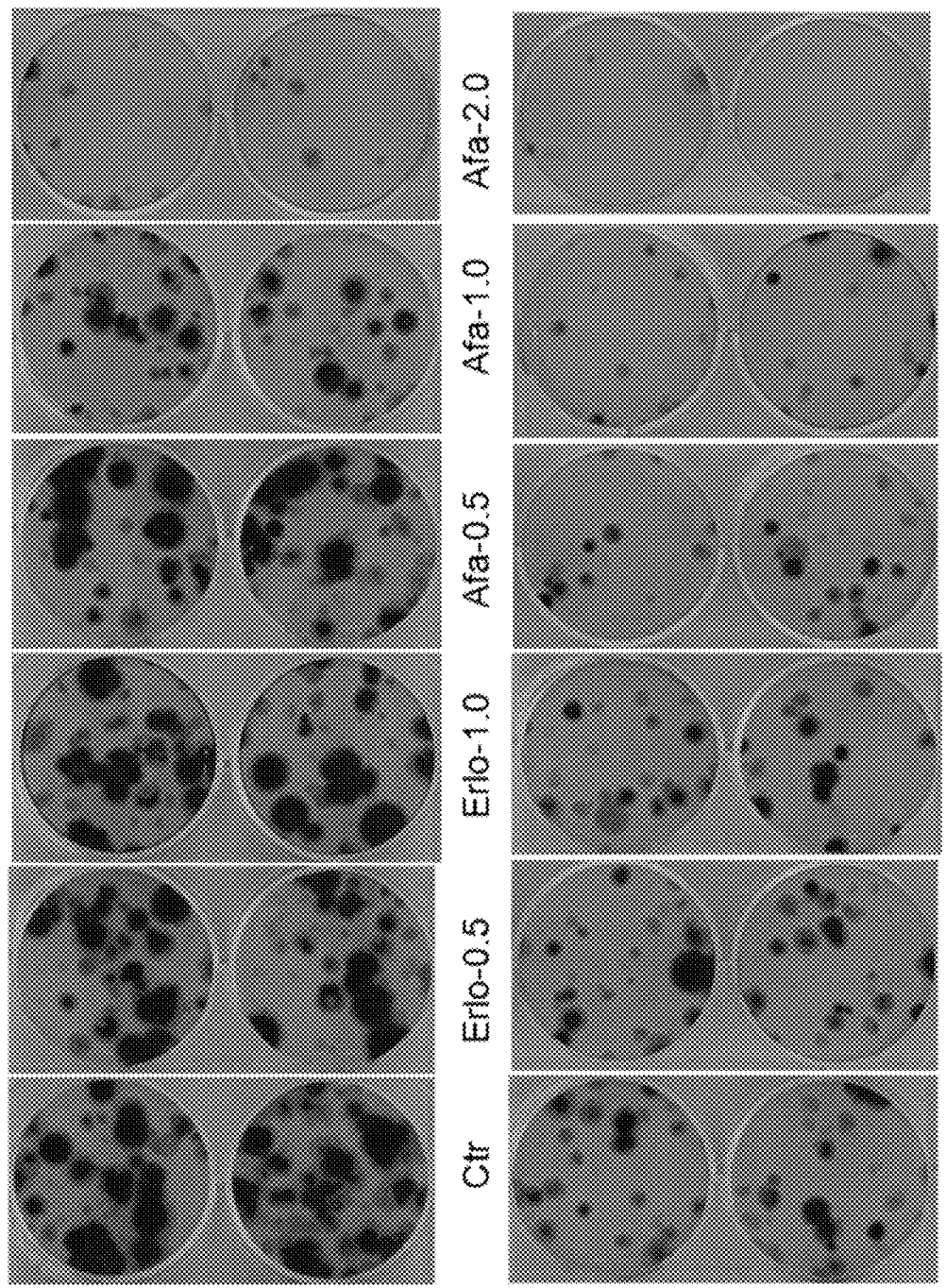
FIG. 26A-B: Afatinib synergistically inhibits colony formation when used in conjunction with TUSC2 nanopraticles. Results are shown for colony formation assays in H1299 (FIG. 26A) or H322 (FIG. 26B) cells. TUSC2 nanoparticle treatment is indicated by "FUS1" versus control treatment "301." These treatments were applied in conjunction with control treatment "CTR"; 0.5 or 1.0 µg of Erlotinib ("Erlo-0.5" or "Erlo-1.0"); or 0.5, 1.0 or 2.0 µg of Afatinib ("Afa-0.5", "Afa-1.0" or "Afa-2.0") as indicated.
Figure 26B:
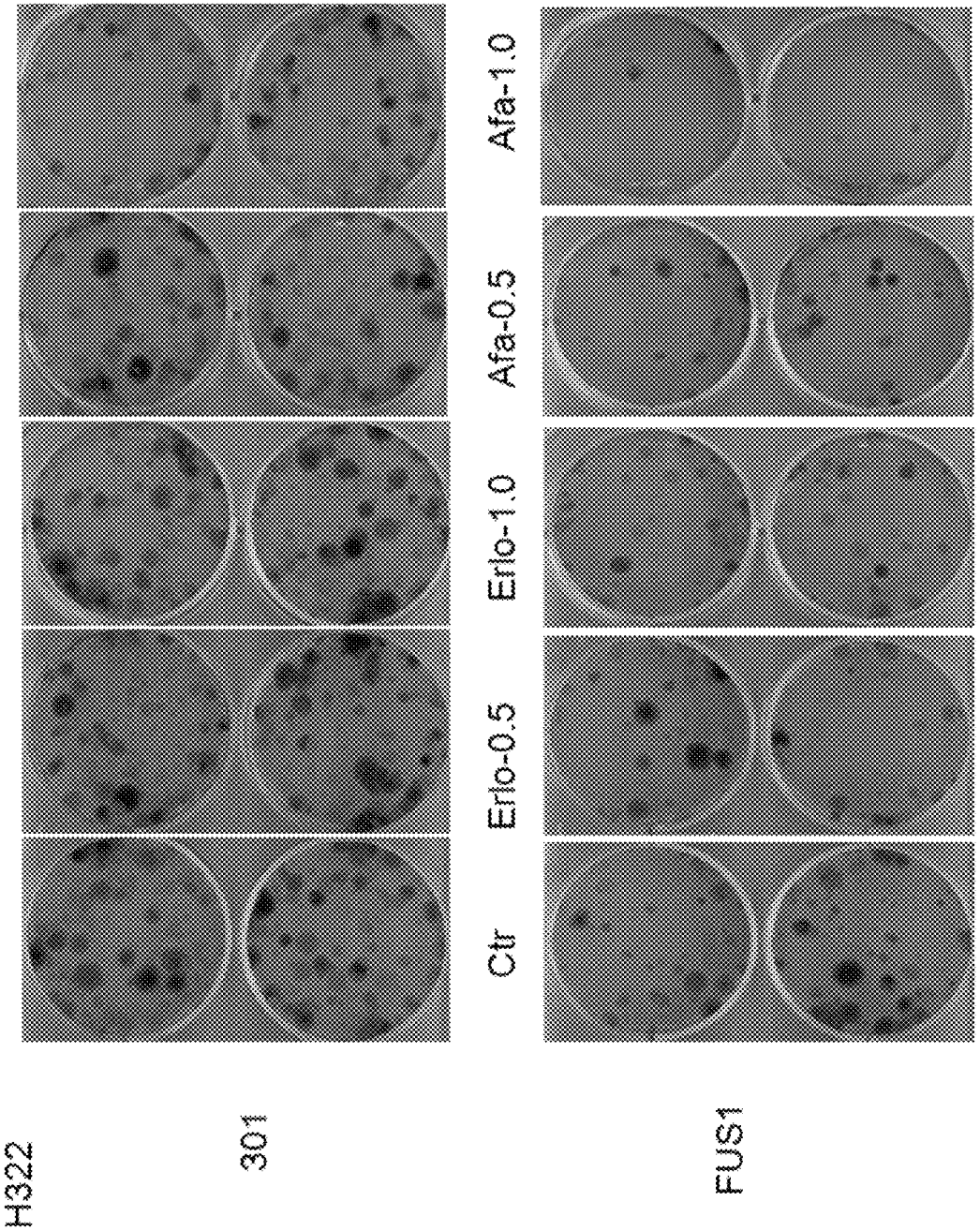

The embodiments and working examples provided herein demonstrate for the first time that TUSC2 therapies show increased effectiveness when combined with EGFR-targeted therapies. Specifically, studies presented here show that erlotinib, an EGFR tyrosine kinase inhibitor, is significantly more effective in reducing cancer cell growth (as measured by colony formation) when applied in conjunction with a TUSC2 therapeutic (see, e.g., FIGS. 6-10 and Tables 5-8). In all five cancer cell lines that were tested application of TUSC2 nanoparticles was able to sensitize the cancer cell to the effects of Erlotinib. The combined treatment was able to achieve a similar level of inhibition of colony formation while using less than half of the amount of a erlotinib (1.0 µg versus 2.3 µg) treatment when provided alone. Moreover, at the higher erlotinib treatment levels (2.3 µg) the combination treatment far exceeded the amount of inhibition that was achievable with either agent alone. These results were confirmed using an in vivo murine tumor explants model. Results shown in FIG. 13 demonstrate that the combination of TUSC2 therapy and erlotinib significantly reduced the number of tumor nodules in the lungs of treated animals as compared to either treatment alone. Further studies in four different cancer cell lines confirmed that TUSC2 therapy likewise was able to sensitize cells to killing by a second EGFR-targeted agent, gefitinib (FIG. 12). Moreover, the tyrosine kinase inhibitor afatinib, which likewise acts to inhibit EGFR signaling, synergistically inhibited cancer cell colony formation when combined with TUSC2 treatment (FIG. 26A-B). Thus, TUSC2 therapy can be used to sensitize cancer cells to the effects of EGFR-targeted therapies (such as erlotinib, afatinib or gefitinib) and thereby reduce the effective amount of the EGFR-targeted therapy required for effective treatment of a cancer.

Figure 18:
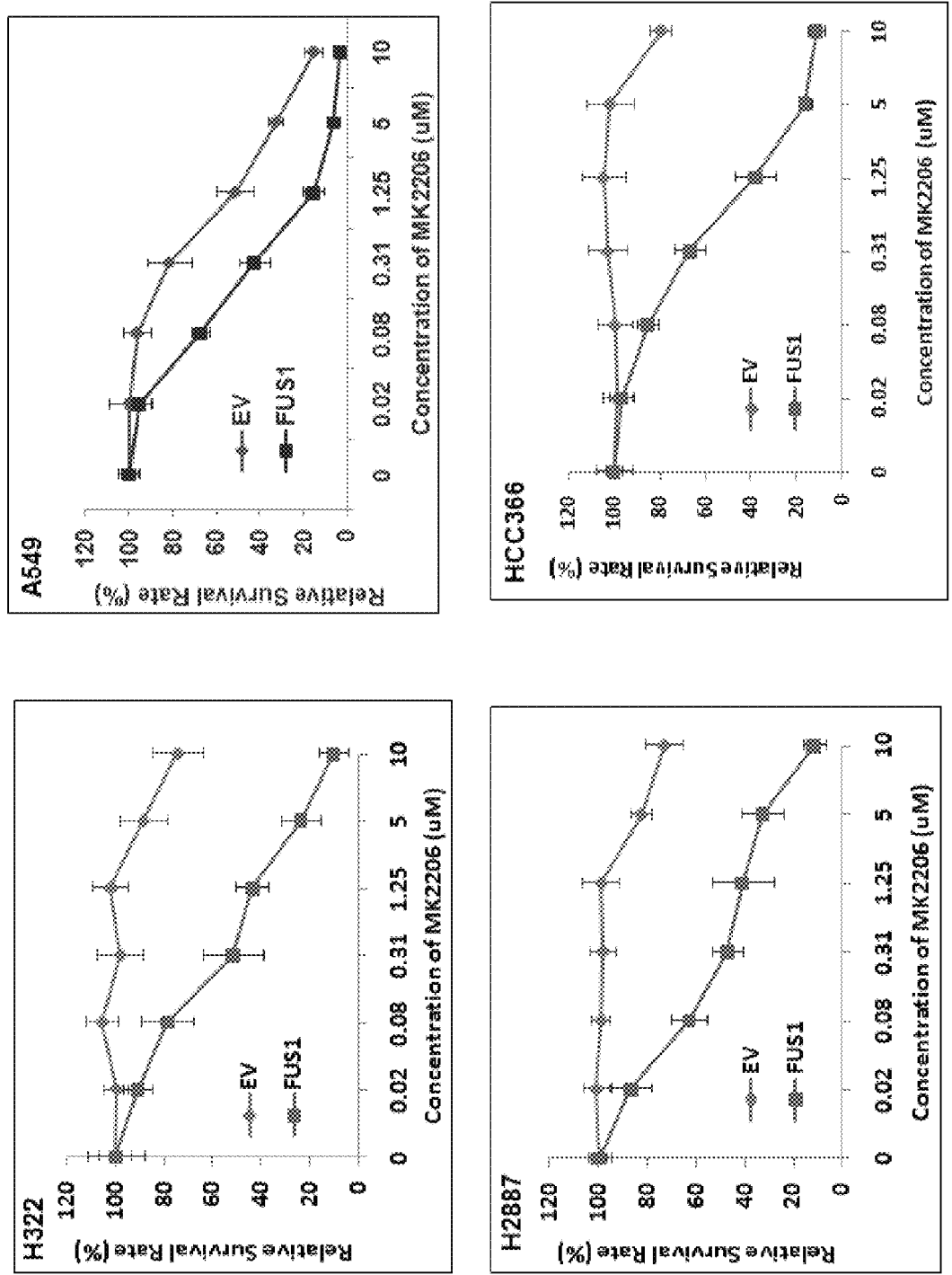
FIG. 18: FUS1/MK2206-induced cell death in lung cancer cell lines. Graphs show the relative survival rates for the indicated cancer cells (y-axis) when contacted with empty vector (EV) or FUS1 nanoparticles in the presence of increasing concentrations of MK2206 (x-axis).
Figure 19:
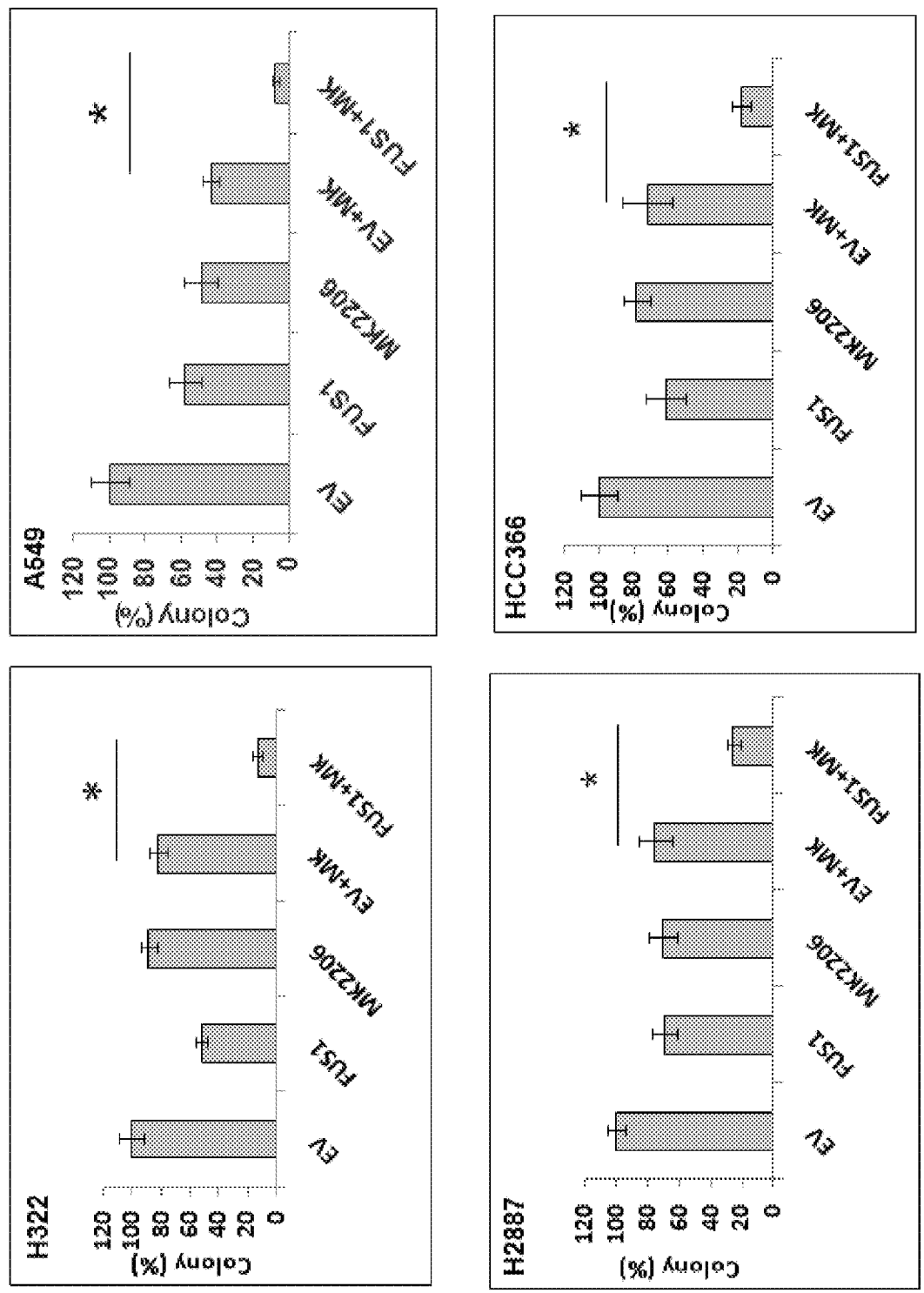
FIG. 19: FUS1/MK2206 inhibit colony formation in lung cancer cell lines. Graphs show the relative percent of colony formation by the indicated cells upon treatment with empty vector (EV); FUS1 nanoparticles (FUS1); MK2206; empty vector+MK2206 (EV+MK); or FUS1 nanoparticles+MK2206 (FUS1+MK). * indicates a statistically significant difference in the amount of colony formation between the two treatments.
Figure 20:
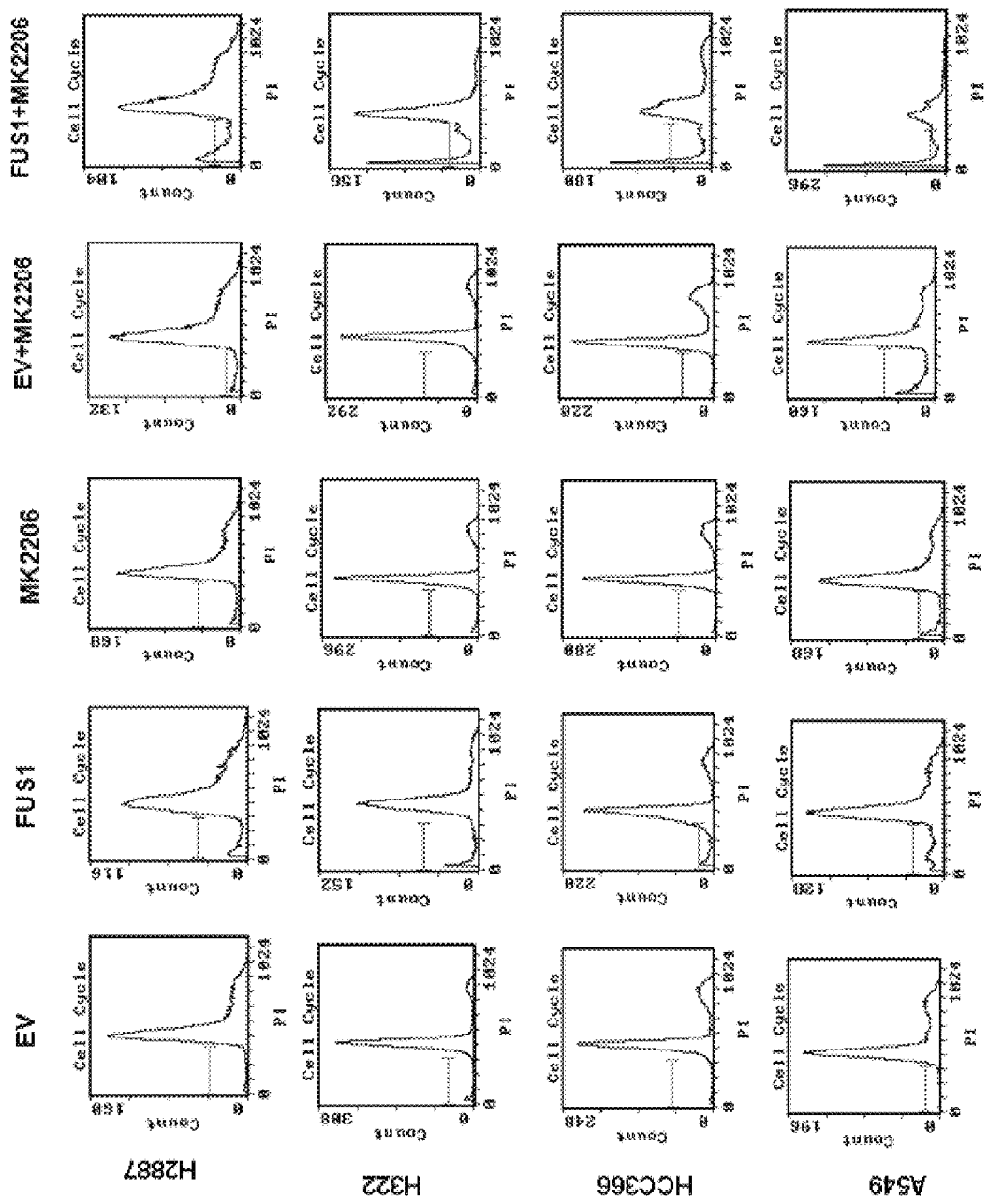
FIG. 20: FUS1/MK2206 induced apoptosis in lung cancer cell lines. The effects of empty vector (EV); FUS1 nanoparticles (FUS1); MK2206; empty vector+MK2206 (EV+MK2206); or FUS1 nanoparticles+MK2206 (FUS1+MK2206) on the cell cycle were examined in the four indicated cancer cell line. Treated cells were stained by propidium iodide (PI) and analyzed by flow cytometry. Histograms show cell count (y-axis) versus PI intensity as a measure of DNA content. The horizontal bar in each histogram indicates apoptotic cells as assessed by PI staining of DNA.
Figure 24:
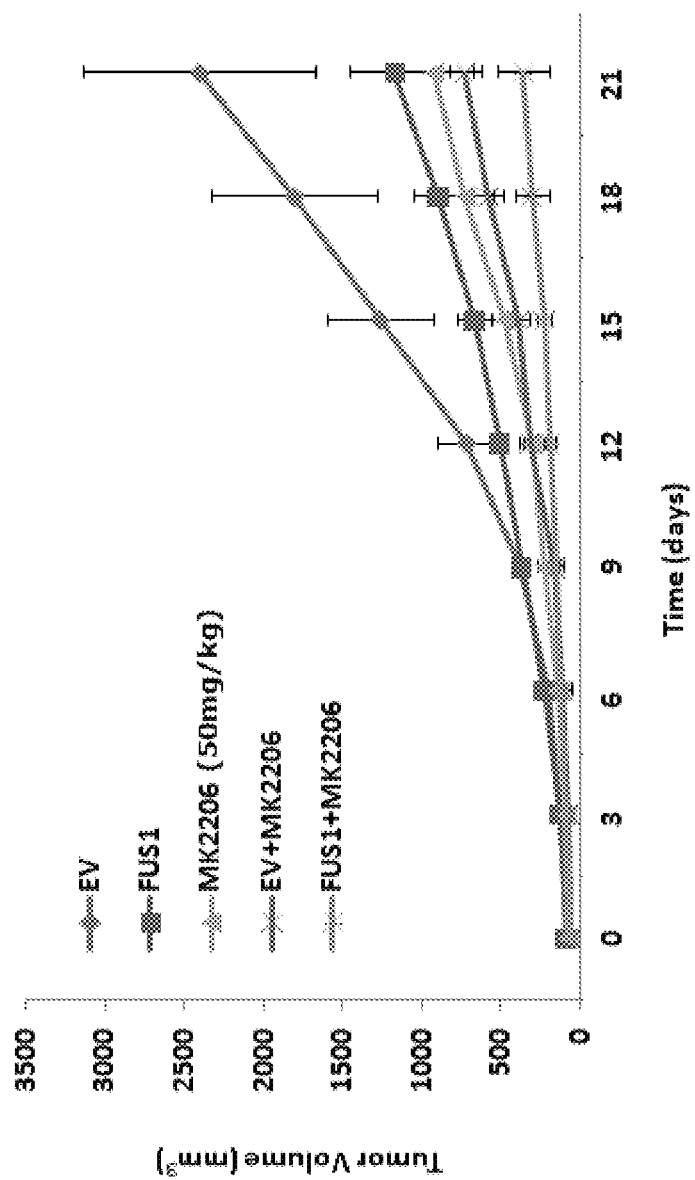
FIG. 24: Combination effects of FUS1 and MK2206 in H322 xenograft mouse model. The chart shows the effects of empty vector (EV); FUS1 nanoparticles (FUS1); MK2206; empty vector+MK2206 (EV+MK2206); or FUS1 nanoparticles+MK2206 (FUS1+MK2206) on H322 tumor growth in vivo. Total tumor volume (y-axis) is plotted as function of time (x-axis). Expression of FUS1 and activity of MK2206 (as evidenced by reduced p-AKT expression) was histologically confirmed in samples from the mice.

Yet further studies presented here demonstrate that TUSC2 therapeutics are also able to sensitized cancer cells to the effects of protein kinase inhibitors. For example, as shown in FIG. 18, the cancer cell killing effect of AKT kinase inhibitor MK2206 were greatly increased when the inhibitor was used in conjunction with TUSC2 nanoparticles. Interestingly, TUSC2 treatment was able to render cells that were otherwise highly resistant to the AKT inhibitor (such as HCC366 cells) susceptible to MK2206 treatment. Combination treatment was also found to be significantly more effective than either treatment alone at reducing colony formation in cancer cells (FIG. 19) and in inducing apoptosis in these cells (FIG. 20). The ability of TUSC2 therapy to sensitize cells to AKT protein kinase therapy was specifically quantified in Table 13, which shows that TUSC2 treatment reduced the effective $IC_{50}$ of MK2206 at least 5-fold and, it some cases, by as much as 16-fold. Furthermore the combined effectiveness of the therapies was confirmed in vivo using a murine tumor explants model. As shown in FIG. 24, the combined administration of TUSC2 nanoparticles and MK2206 was far more effective than each therapy in isolation at preventing tumor growth and tumor growth in co-treated animals was infect very minimal. Thus, the TUSC2 therapies described here can be combined with protein kinase inhibitor therapies to further increase the effectiveness of these inhibitors and even to reverse resistance to such agents in cancers.

I. Assessing Apoptosis

As detailed above, methods for determining the proportion of apoptotic cancer cells in a subject can be useful predicting a response to TUSC2 therapy. Assessment of apoptosis may be performed on a sample of cancer cells from the subject or in vivo assessment may be performed (e.g., by imaging). For example, methods for in vivo assessment of apoptosis were recently review by Blankenberg 2008 and Zhao 2009 (both of which are incorporated herein by reference). A wide range of methods may be employed to identify apoptotic cells, ranging from simple light microscopy to molecular assays that detect changes in cellular membrane integrity, changes in cellular gene expression, activation proteases and DNA fragmentation.

In certain aspects, the proportion (i.e., percentage) of cells in a sample that are apoptotic. However, it will be recognized that not all methods for determining apoptosis provide an assessment on a cell-by-cell basis. Thus, in certain aspects, a level of apoptosis is determined for a sample, wherein the level correlates with a particular portion of apoptotic cells (e.g., at least about 10% apoptotic cells). For example, level of apoptosis may be determine for the cancer cells of patient (e.g., the intensity of in vivo Annexin V staining) and the level correlated to a percentage of apoptotic cells to determine whether the subject will response favorably to a TUSC2 therapy.

a. DNA Fragmentation

During apoptosis nuclear DNA is fragmented and these changes can be detected to assess apoptosis in a sample. Fragmented DNA may be detected, for example, by light microscopy, which can reveal condensation and margination of chromatin. Fragmentation of DNA can also be directly assessed using a separative method, e.g., chromatography or electrophoresis, to size fractionate the sample. For example, DNA fragmentation, characteristic of apoptosis, will be visualized as "ladders" containing a wide range of fragments. Use of such methods, however, may not provide the best quantitative assessment of apoptosis.

Apoptotic cells can also be detected by end labeling of fragmented DNA. For instance, apoptosis can be assayed using terminal deoxytransferase-mediated (TdT) dUTP biotin nick end-labeling (TUNEL; Gavriel et al., J. Cell Biol. 119:493 (1992); Gorczyca et al., Int. J. Oncol. 1:639 (1992). TUNEL labeling is effected by incorporation of labeled nucleotides into the 3' hydroxyl termini of the DNA breaks characteristic of apoptosis using the enzyme terminal transferase. The incorporated nucleotide may be labeled by a wide variety of techniques. A typical approach is to incorporate a ligand such as fluorescein, biotin or digoxigenin into the nucleotide. If the ligand itself is not capable of yielding a signal, typically fluorescence, it can be reacted with a second moiety such as an appropriate antibody or other receptor which does carry a signal generator after incorporation of the nucleotide into the DNA terminal. Typical of such an approach is the use of a digoxigenin carrying nucleotide with the later reaction with an anti-digoxigenin antibody carrying Rhodamine, or a bromolated nucleotide with the later reaction with an appropriate antibody carrying fluorescein.

A similar labeling method is know as in situ end-labeling (INSEL). For INSEL, labeling is effected in a similar manner to TUNEL labeling except that the labeled nucleotide is incorporated using the enzyme DNA polymerase I or its Klenow fragment. It is general this method may be somewhat less sensitive and specific than TUNEL labeling.

Both TUNEL and INSEL labeling require that certain steps be taken in order to have the labeled nucleotides access the nuclear DNA of the cells being analyzed. These steps are well known and included in the instructions accompanying the commercial kits. In general they involve rendering the cell walls of the cells being analyzed permeable to the labeled nucleotide and incorporating enzyme and removing any protein masking by appropriate protein digestion such as with pepsin.

b. Lose of Membrane Integrity

During apoptosis membrane integrity of the plasma membrane and mitochondrial membrane is altered and these alterations can be detected to identify apoptotic cells. For example, light microscopy may be used to determine the presence of one or more morphological characteristics of apoptosis such as condensed or rounded morphology, shrinking and blebbing of the cytoplasm. Likewise, certain membrane constituents can become exposed to the exterior of the cell and detected as an indicator of apoptosis.

Detection of phosphatidylserine on the exterior of cells can be indicative of apoptosis. For example, commercial kits are available for the detection of phosphatidylserine via Annexin V binding (see, e.g., the FITC Annexin V Apoptosis Kit available from BD Pharmingen™) Labeled Annexin V, such as radiolabeled Annexin V, may also be used for in vivo imaging of cancer cells to assess apoptosis (see, e.g., Blankenberg 2008).

Permeablization of the mitochondrial membrane is also an indicator of apoptosis. Once, mitochondrial membrane integrity is lost certain proteins are released to the cytoplasm and detection of such proteins may be use to assess apoptosis. For example, detection of cytochrome c (Cyt c) release is a commonly used apoptotic indicator.

c. Caspase Activation

Members of the caspase family of proteins are major effectors of cellular apoptosis. Caspases are cysteine proteases that exist within the cell as inactive pro-forms or so-called "zymogens." The zymogens are cleaved to form active enzymes following the induction of apoptosis either via the death receptor-mediated pathway or the mitochondrial pathway of apoptosis. Depending upon the apoptotic pathway, different caspases initiate the apoptotic process, with Caspase-8 and -10 initiating the death receptor pathway, and Caspase-9 initiating the mitochondrial pathway. Active initiator caspases then activate (i.e., cleave) effector caspases, for example, Caspase-3, -6, and -7, to induce apoptosis. These effector caspases cleave key cellular proteins that lead to the typical morphological changes observed in cells undergoing apoptosis. Thus, in certain aspects, apoptosis can be detected by directly detecting caspase activity (e.g., by use of fluorescently labeled peptides with a caspase cleavage site) or indirectly detecting the activated enzymes by detecting a cleaved target polypeptide.

One protein often used to indirectly detect caspase activity is poly(ADP-ribose) polymerase (PARP-1). PARD-1 is a DNA-binding protein that is specifically cleaved during apoptosis. Active PARP-1 catalyzes the addition of poly (ADP-ribose) chains to some nuclear proteins and is thought to play a critical role in DNA damage repair. PARP-1 is rapidly activated during cellular stresses, such as heat shock, ionizing radiation, exposure to carcinogens, and treatment with chemotherapy agents. During apoptosis, activated (i.e., cleaved) caspase-3 in turn cleaves PARP-1. Thus, the presence and indeed the level of cleaved PARP-1 can be used to assess apoptosis in a sample.

d. Changes in Gene Expression

A variety of additional changes in cellular gene expression occur during apoptosis and can be detected as indicators of apoptosis. For example, the expression of pro-apoptotic proteins such as Bid, Bim, Bik, Bmf, Bad, Hrk, BNIP3, Bax, Bak, and Bok may be used as an apoptotic marker.

II. Nucleic Acid and Polypeptide Complexes

In certain aspects, concerns compositions and methods for delivering a nucleic acid or a polypeptide to a cell. In particular, provided herein are nanoparticle-nucleic acid or nanoparticle-polypeptide complexes and methods of administering such complexes to a subject. The complexes comprise a TUSC2 polypeptide and/or nucleic acid in association with a nanoparticle. As used herein, "association" means a physical association, a chemical association or both. For example, an association can involve a covalent bond, a hydrophobic interaction, encapsulation, surface adsorption, or the like.

Polypeptides and nucleic acids typically have difficulty crossing cellular membranes. Both types of molecules include charged residues, which hinder membrane binding and membrane transport into cells. The present embodiments overcome this difficulty by, providing nanoparticle complexes that facilitate cellular uptake.

In accordance with the present embodiments, a polypeptide and/or nucleic acid may be associated with a nanoparticle to form nanoparticle complex. In some embodiments, the nanoparticle is a liposomes or other lipid-based nanoparticle such as a lipid-based vesicle (e.g., a DOTAP:cholesterol vesicle). As used in cancer therapy, liposomes take advantage of the increased fenestrations in the cancer neovasculature to enhance liposome concentration at tumor sites.

In other embodiments, the nanoparticle is a non-lipid nanoparticle, such as an iron-oxide based superparamagnetic nanoparticles. Superparamagnetic nanoparticles ranging in diameter from about 10 to 100 nm are small enough to avoid sequestering by the spleen, but large enough to avoid clearance by the liver. Particles this size can penetrate very small capillaries and can be effectively distributed in body tissues. Superparamagnetic nanoparticles complexes can be used as MRI contrast agents to identify and follow those cells that take up the therapeutic complexes. In certain embodiments, the nanoparticle is a semiconductor nanocrystal or a semiconductor quantum dot, both of which can be used in optical imaging. In further embodiments, the nanoparticle can be a nanoshell, which comprises a gold layer over a core of silica. One advantage of nanoshells is that a polypeptideor nucleic acid can be conjugated to the gold layer using standard chemistry. In other embodiments, the nanoparticle can be a fullerene or a nanotube (Gupta et al., 2005).

In accordance with the present embodiments, nanoparticle complexes can be targeted to specific tissues and cells. This can be accomplished by conjugating a cell targeting moiety to the nanoparticle. The targeting moiety can be, but is not limited to, a protein, peptide, lipid, steroid, sugar, carbohydrate or synthetic compound. Cell targeting moieties such as ligands recognize and bind to their cognate receptors on the surface of cells. Similarly, antibody can act as cell targeting moieties by recognizing their cognate antigens on the cell surface. In certain embodiments, targeted nanoparticle complexes provided herein can enhance the specificity of disease treatment and increase the amount of therapeutic agent entering a targeted cell.

a. Nanoparticles

As used herein, the term "nanoparticle" refers to any material having dimensions in the 1-1,000 nm range. In some embodiments, nanoparticles have dimensions in the 50-500 nm range. Nanoparticles used in the present embodiments include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube (Ferrari, 2005). The conjugation of polypeptide or nucleic acids to nanoparticles provides structures with potential application for targeted delivery, controlled release, enhanced cellular uptake and intracellular trafficking, and molecular imaging of therapeutic peptides in vitro and in vivo (West, 2004; Stayton et al., 2000; Ballou et al., 2004; Frangioni, 2003; Dubertret et al., 2002; Michalet et al., 2005; Dwarakanath et al., 2004.

1. Lipid-Based Nanoparticles

Lipid-based nanoparticles include liposomes, lipid preparations and lipid-based vesicles (e.g., DOTAP:cholesterol vesicles). Lipid-based nanoparticles may be positively charged, negatively charged or neutral. In certain embodiments, the lipid-based nanoparticle is neutrally charged (e.g., a DOPC liposome).

A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Liposomes provided herein include unilamellar liposomes, multilamellar liposomes and multivesicular liposomes. Liposomes provided herein may be positively charged, negatively charged or neutrally charged. In certain embodiments, the liposomes are neutral in charge.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In specific aspects, a polypeptide or nucleic acids may be, for example, encapsulated in the aqueous interior of a liposome, interspersed within the lipid bilayer of a liposome, attached to a liposome via a linking molecule that is associated with both the liposome and the polypeptide/nucleic acid, entrapped in a liposome, complexed with a liposome, or the like.

A liposome used according to the present embodiments can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with a polypeptide, nucleic acid, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

The dried lipids or lyophilized liposomes prepared as described above may be dehydrated and reconstituted in a solution of a protein or peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

In other alternative methods, liposomes can be prepared in accordance with other known laboratory procedures (e.g., see Bangham et al., 1965; Gregoriadis, 1979; Deamer and Uster, 1983; Szoka and Papahadjopoulos, 1978, each incorporated herein by reference in relevant part). Additional liposomes which may be useful with the present embodiments include cationic liposomes, for example, as described in WO02/100435A1, U.S. Pat. No. 5,962,016, U.S. Application 2004/0208921, WO03/015757A1, WO04029213A2, U.S. Pat. No. 5,030,453, and U.S. Pat. No. 6,680,068, all of which are hereby incorporated by reference in their entirety without disclaimer. A process of making liposomes is also described in WO04/002453A1. Neutral lipids can be incorporated into cationic liposomes (e.g., Farhood et al., 1995). Various neutral liposomes which may be used in certain embodiments are disclosed in U.S. Pat. No. 5,855,911, which is incorporated herein by reference. These methods differ in their respective abilities to entrap aqueous material and their respective aqueous space-to-lipid ratios.

The size of a liposome varies depending on the method of synthesis. Liposomes in the present embodiments can be a variety of sizes. In certain embodiments, the liposomes are small, e.g., less than about 100 nm, about 90 nm, about 80 nm, about 70 nm, about 60 nm, or less than about 50 nm in external diameter. For example, in general, prior to the incorporation of nucleic acid, a DOTAP:cholesterol liposome for use according to the present embodiments comprises a size of about 50 to 500 nm. Such liposome formulations may also be defined by particle charge (zeta potential) and/or optical density (OD). For instance, a DOTAP:cholesterol liposome formulation will typically comprise an $OD_{400}$ of less than 0.45 prior to nucleic acid incorporation. Likewise, the overall charge of such particles in solution can be defined by a zeta potential of about 50-80 mV.

In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

In certain embodiments, the lipid based nanoparticle is a neutral liposome (e.g., a DOPC liposome). "Neutral liposomes" or "non-charged liposomes", as used herein, are defined as liposomes having one or more lipid components that yield an essentially-neutral, net charge (substantially non-charged). By "essentially neutral" or "essentially non-charged", it is meant that few, if any, lipid components within a given population (e.g., a population of liposomes) include a charge that is not canceled by an opposite charge of another component (i.e., fewer than 10% of components include a non-canceled charge, more preferably fewer than 5%, and most preferably fewer than 1%). In certain embodiments, neutral liposomes may include mostly lipids and/or phospholipids that are themselves neutral under physiological conditions (i.e., at about pH 7).

Liposomes and/or lipid-based nanoparticles of the present embodiments may comprise a phospholipid. In certain embodiments, a single kind of phospholipid may be used in the creation of liposomes (e.g., a neutral phospholipid, such as DOPC, may be used to generate neutral liposomes). In other embodiments, more than one kind of phospholipid may be used to create liposomes.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes. In certain embodiments, a lipid that is not a phospholipid (e.g., a cholesterol) may be used Phospholipids include glycerophospholipids and certain sphingolipids. Phospholipids include, but are not limited to, dioleoylphosphatidylcholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used, in certain embodiments, as the primary phosphatide (i.e., constituting 50% or more of the total phosphatide composition) because this may result in instability and leakiness of the resulting liposomes.

2. DOTAP:Cholesterol Nanoparticle

In certain embodiments, the lipid-based vesicle is a DOTAP:cholesterol nanoparticle. DOTAP:cholesterol nanoparticles are prepared by mixing the cationic lipid DOTAP (1,2-bis(oleoyloxy)-3-(trimethylammonio)-propane) with cholesterol. Vesicles prepared with DNA can form a structure (called a "sandwich") where the DNA appears to be condensed between two lipid bilayers (U.S. Pat. Nos. 6,770,291 and 6,413,544).

A DOTAP:cholesterol-nucleic acid complex can be prepared as in the following non-limiting example. The DOTAP:cholesterol (DC) nanoparticles (sized 50 to 500 nm) are synthesized as described previously (U.S. Pat. Nos. 6,770,291 and 6,413,544; Templeton, 1997). Briefly, 420 mg of DOTAP and 208 mg of cholesterol are measure and mixed together with 30 ml of chloroform. Mixture is then allowed to dry on a rotary evaporator for 30 minutes and freeze dry for 15 minutes. The dried mixture is reconstituted in 30 ml of D5W by swirling at 50° C. for 45 minutes and 37° C. for 10 minutes. The mixture is ten subjected to low frequency sonication for five minutes to form liposomes. DOTAP:cholesterol liposome are then heated to 50° C. and sequentially filtered through 1.0, 0.45, 0.2 and 0.1 μm sterile Whatman filters. The synthesized nanoparticles are stored at 4° C. and used for preparing nanoparticle complexes. The formulated DOTAP:cholesterol liposome should be evenly dispersed with a particle size of 50-250 nm, an $OD_{400}$ of less than 0.45 and zeta potential of 50-80 mV. Residual $CHCl_3$ levels should be less than 60 ppm.

To prepare DOTAP:cholesterol-nucleic acid nanoparticles, 240 μl of liposomes (see above) are diluted in 360 μl D5W at room temperature. DNA (~5 mg/ml) is added to the mixture to a total volume of 600 μl. The mixture is moved up and down in a pipet to mix. Once settled the mixture should have a an $OD_{400}$ of between 0.65 and 0.95, a particle size of 200-500 nm and be confirmed gram stain negative. The liposome complexes are stored at between 3° C. and 28° C. and agitated as little as possible.

b. Targeting of Nanoparticles

Targeted delivery is achieved by the addition of ligands without compromising the ability of nanoparticles to deliver their payloads. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-α, nerve growth factor, albumin, HIV Tat peptide, RGD peptide, and insulin, as well as others (Gupta et al., 2005; Ferrari, 2005).

III. TUSC2 Expression Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

In certain embodiments, provided herein is the use of nucleic acids TUSC2 coding sequence. For example, such vector can be used for recombinant production of a TUSC2 polypeptide and/or for the expression of TUSC2 in vivo in a subject. The sequences may be modified, given the ability of several different codons to encode a single amino acid, while still encoding for the same protein or polypeptide. Optimization of codon selection can also be undertaken in light of the particular organism used for recombinant expression or may be optimized for maximal expression in human cell (e.g., a cancer cell). Vector for use in accordance with the present embodiments additionally comprise elements that control gene expression and/or aid in vector production and purification.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the coding nucleic acid segment under the control of a recombinant, exogenous or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include viral promoter and enhancers such as the CMV promoter.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

b. Translation Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference). Inclusion of such splice sites also can enhance expression by averting non-sense mediated decay of resulting RNA transcripts.

e. Termination Signals

The vectors or constructs of the present embodiments will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

Terminators contemplated for use in the present embodiments include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the present embodiments, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments, cells containing a nucleic acid construct provided herein may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of 2-24 hr, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Viruses may thus be utilized that encode and express TUSC2. Non-limiting examples of virus vectors that may be used to deliver a TUSC2 nucleic acid are described below.

Adenoviral Vectors.

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

AAV Vectors.

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors.

Retroviruses have the ability to integrate their genes into the host genome, transferring a large amount of foreign genetic material, infecting a broad spectrum of species and cell types and of being packaged in special cell-lines (Miller, 1992). In order to construct a retroviral vector, a nucleic acid (e.g., one encoding a protein of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Other Viral Vectors.

Other viral vectors may be employed as vaccine constructs in the present embodiments. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Modified Viruses.

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

IV. Pharmaceutical Formulations

Pharmaceutical compositions provided herein comprise an effective amount of one or more TUSC2 therapeutic and, optionally, an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least TUSC2 nucleic acid, peptide or a nanoparticle complex or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

In certain embodiments, the pharmaceutical composition may comprise different types of carriers depending on whether it is to be administered in solid, liquid or aerosol form, and whether it need to be sterile for such routes of administration as injection. In certain embodiments, pharmaceutical compositions provided herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

In certain embodiments, the pharmaceutical composition is administered intraperitoneally. In further embodiments, the pharmaceutical composition is administered intraperitoneally to treat a cancer (e.g., a cancerous tumor). For example, the pharmaceutical composition may be administered intraperitoneally to treat gastrointestinal cancer. In certain embodiments it may be disirable to administer the pharmaceutical composition into or near a tumor.

In certain preferred embodiments, the pharmaceutical composition is administered orally to treat a cancer (e.g., a gastrointestinal cancer).

In certain embodiments, the actual dosage amount of a composition administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 15 microgram/kg/body weight, about 20 microgram/kg/body weight, about 25 microgram/kg/body weight, about 30 microgram/kg/body weight, about 35 microgram/kg/body weight, about 0.04 milligram/kg/body weight, about 0.05 milligram/kg/body weight, about 0.06 milligram/kg/body weight, about 0.07 milligram/kg/body weight, about 0.08 milligram/kg/body weight, about 0.09 milligram/kg/body weight, about 0.1 milligram/kg/body weight, about 0.2 milligram/kg/body weight, to about 0.5 mg/kg/body weight or more per administration, and any range derivable therein. In non-limiting examples of a derivable range from the numbers listed herein, a range of about 0.01 mg/kg/body weight to about 0.1 mg/kg/body weight, about 0.04 microgram/kg/body weight to about 0.08 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The one or more peptides, nanoparticle complexes or additional agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present embodiments. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the one or more polypeptide, nucleic acid or nanoparticle complexes are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

V. Combination Therapies

In order to increase the effectiveness of a nucleic acid, polypeptide or nanoparticle complex of the present embodiments, it may be desirable to combine these compositions with other agents effective in the treatment of the disease of interest.

As a non-limiting example, the treatment of cancer may be implemented with TUSC2 therapeutic of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the anti-cancer peptide or nanoparticle complex and the other includes the second agent(s). In particular embodiments, an anti-cancer peptide can be one agent, and an anti-cancer nanoparticle complex can be the other agent.

Treatment with the anti-cancer peptide or nanoparticle-complex may precede or follow the other agent treatment by intervals ranging from minutes to weeks. In embodiments where the other agent and the anti-cancer peptide or nanoparticle complex are applied separately to the cell, one would generally ensure that a significant period of time did not expire between the time of each delivery, such that the agent and the anti-cancer peptide or nanoparticle complex would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Likewise, in certain aspects a TUSC2 therapy is administered in conjunction with an anti-inflammatory agent. For example, a TUSC2 therapy may precede or follow the anti-inflammatory agent treatment by intervals ranging from minutes to weeks. In certain aspects, the anti-inflammatory agent is administered immediately before the TUSC2 therapy and immediately after the TUSC2 therapy. For example, the anti-inflammatory agent may be given less than a day before and less than a day after the therapy. In still further aspects more than one anti-inflammatory is administered, such administration of a antihistamine (e.g., diphenhydramine) and a corticosteroid (e.g., dexamethasone).

Various combinations may be employed, where the TUSC2 therapy is "A" and the secondary agent, such as radiotherapy, chemotherapy or anti-inflammatory agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In certain embodiments, administration of the TUSC2 therapy of the present embodiments to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

a. Chemotherapy

Cancer therapies also include a variety of combination therapies. In some aspects a TUSC2 therapeutic of the embodiments is administered (or formulated) in conjunction with a chemotherapeutic agent. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a TUSC2 therapy of the present embodiments. The general approach for combined therapy is discussed below. Generally, the tumor cell must bear some marker that is amenable to targeting, i.e., is not present on the majority of other cells. Many tumor markers exist and any of these may be suitable for targeting in the context of the present embodiments. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these method are well known in the art (see, e.g. Sambrook et al., 1989; Ausubel et al., 1998; Ausubel, 1996).

Delivery of a vector encoding one of the following gene products will have a combined anti-hyperproliferative effect on target tissues. A variety of proteins are encompassed within the present embodiments, some of which are described below.

i. Inhibitors of Cellular Proliferation

As noted above, the tumor suppressor oncogenes function to inhibit excessive cellular proliferation. The inactivation of these genes destroys their inhibitory activity, resulting in unregulated proliferation.

Genes that may be employed as secondary treatment in accordance with the present embodiments include p53, p16, Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors), MCC and other genes listed in Table IV.

ii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, *Proc. Nat'l. Acad. Sci. USA,* 82(21):7439-43, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Anti-Inflammatory Agents

In certain aspects TUSC2 therapies are administered in conjuction with an anti-inflammatory agent. An anti-inflammatory agent is defined herein to refer to an agent that is known or suspected to be of benefit in the treatment or prevention of inflammation in a subject. Corticosteroids are a major class of anti-inflammatory agent. The corticosteroids may be short, medium, or long acting, and may be delivered in a variety of methods. A non-limiting list of corticosteroids contemplated in the present embodiments include the oral corticosteroids such as: cortisone, hydrocortisone, prednisone, and dexamethasone.

Another major class of anti-inflammatory agents are non-steroidal anti-inflammatory agents. Non-steroidal anti-inflammatory agents include a class of drugs used in the treatment of inflammation and pain. The exact mode of action of this class of drugs is unknown. Examples of members of this class of agents include, but are not limited to, ibuprofen, ketoprofen, flurbiprofen, nabumetone, piroxicam, naproxen, diclofenac, indomethacin, sulindac, tolmetin, etodolac, flufenamic acid, diflunisal, oxaprozin, rofecoxib, and celecoxib. One of ordinary skill in the art would be familiar with these agents. Included in this category are salicylates and derivates of salicylates, such as acetyl salicylic acid, sodium salicylate, choline salicylate, choline magnesium salicylate and diflunisal.

Other anti-inflammatory agents include anti-rheumatic agents, such as gold salts (e.g., gold sodium thiomalate, aurothioglucose, and auranofin), anti-rheumatic agents (e.g., chloroquine, hydroxychloroquine, and penicillamine), antihistamines (e.g., diphenhydramine, chlorpheniramine, clemastine, hydroxyzine, and triprolidine), and immunosuppressive agents (e.g., methotrexate, mechlorethamine, cyclophosphamide, chlorambucil, cyclosporine, and azathioprine). Other immunosuppressive agent contemplated by the present embodiments is tacrolimus and everolimus. Tacrolimus suppresses interleukin-2 production associated with T-cell activation, inhibits differentiation and proliferation of cytotoxic T cells. Today, it is recognized worldwide as the cornerstone of immunosuppressant therapy. One of ordinary skill in the art would be familiar with these agents, and other members of this class of agents, as well as the mechanism of actions of these agents and indications for use of these agents.

g. Other Agents

It is contemplated that other agents may be used in combination with the compositions provided herein to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the compositions provided herein by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the compositions provided herein to improve the anti-hyerproliferative efficacy of the treatments Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the compositions provided herein to improve the treatment efficacy.

In certain embodiments, hormonal therapy may also be used in conjunction with the present embodiments or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

EXAMPLES

The following examples are included to demonstrate preferred embodiments provided herein. It should be appreciated by those of skill in the art that the techniques disclosed in the examples which follow represent techniques discovered by the inventors to function well in the practice of the present embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present embodiments.

Example 1 Clinical Study Design

Eligible patients were required to have histologically documented non-small cell lung cancer (NSCLC) or small cell lung cancer (SCLC) not curable by standard therapies and previously treated with platinum-based chemotherapy. The primary end point was assessment of DOTAP:chol-TUSC2 toxicity during cycle 1 and determination of the maximum tolerated dose (MTD). Cycles consisted of a single intravenous infusion every 21 days. Secondary end points included TUSC2 plasmid expression in pretreatment and 24 hour post treatment tumor specimens from subjects consenting to tumor biopsies and tumor response. The presence of viable cancer cells in the biopsied lesion was confirmed in all cases by histopathological examination. Mandatory biopsies were explicitly precluded by regulatory committees at the local and federal level. Tumor response assessed by computed tomography (CT) scans was determined in accordance with standard World Health Organization (WHO) criteria (Miller et al., 1981). This study was approved by the University of Texas MD Anderson Institutional Review Board, the NIH Recombinant DNA Advisory Committee, and the FDA. All patients provided written informed consent prior to entry into the study.

Other eligibility criteria included: Eastern Cooperative Oncology Group (ECOG) performance status ≤1; adequate hematologic, hepatic, and renal function; prothrombin time and partial thromboplastin time ≤1.25 times the upper limit of normal; left ventricular ejection fraction >50%; forced expiratory volume in 1 second (FEV1) and diffusing capacity of the lung for carbon monoxide (DLCO)≥40% of predicted; and negative human immunodeficiency virus serology test. Exclusion criteria included: prior gene therapy; brain metastases, unless treated, asymptomatic, and not requiring steroid therapy; chemotherapy within 21 days before enrollment; radiation therapy within 30 days before enrollment; investigational therapies within 30 days before enrollment; active infection requiring antibiotic therapy; myocardial infarction or angina within 6 months before enrollment; and pregnancy or lactation.

A history and physical examination were performed before every cycle. Adverse events were assessed and laboratory tests performed prior to each cycle and on days 2, 3, and 8. Laboratory tests included a complete blood count with differential, sodium, potassium, chloride, calcium, albumin, total protein, blood urea nitrogen, creatinine, alanine aminotransferase, aspartate aminotransferase, alkaline phosphatase, lactate dehydrogenase, and total bilirubin. Urinalysis and electrocardiograms were obtained prior to each cycle.

The primary end point was assessment of DOTAP:chol-TUSC2 toxicity during cycle 1 and determination of the maximum tolerated dose (MTD). Secondary end points included tumor response and TUSC2 plasmid expression in pretreatment and 24 hour posttreatment tumor specimens from subjects consenting to tumor biopsies. DOTAP:chol-TUSC2 was administered at escalating doses as a 30 minute infusion in a peripheral vein in a total volume of 100 mL of 5% dextrose solution. Patients received DOTAP:chol-TUSC2 every 21 days for up to 6 treatments. After the ninth patient was enrolled, the protocol was amended to require diphenhydramine 50 mg orally or intravenously 30 minutes prior to treatment and dexamethasone 8 mg orally 24 and 12 hours before treatment, 20 mg intravenously 30 minutes prior to treatment, and 8 mg orally 12, 24, and 36 hours after treatment.

The initial starting dose (0.02 mg/kg) was selected based on toxicology studies in non-human primates. This dose was one tenth the dose which resulted in no deaths in non-human primates. After the sixth patient was enrolled, the starting dose was amended to 0.01 mg/kg. Dose escalation was based on a continuous reassessment method (CRM) which allows the MTD to be periodically re-estimated (O'Quigley et al., 1990). The MTD was defined as the highest dose level in which no more than 10% of patients develop dose-limiting toxicity (DLT), defined as grade 3 non-hematologic or hematologic toxicity during cycle 1 judged by the investigator to be related to DOTAP:chol-TUSC2. Patients entered at a given dose level were not eligible for dose escalation or dose reduction. A cohort of 3 patients was treated at each dose level. After treating 3 patients at a given dose level, the information of whether the patients developed DLT was used to compute the posterior probability of toxicity. Only toxicity during cycle 1 was used to determine the next dose level. If no DOTAP:chol-TUSC2-related toxicities were observed in any prior patient, the subsequent dose level was increased by 100%. If only grade 1 or 2 toxicities were observed, the subsequent dose level was increased by 50%. If any DLT was observed, the CRM could lead to either escalation or reduction of dose levels. If DLT occurred and the CRM resulted in a dose escalation, the subsequent dose level was increased by 25%. Toxicity was graded according to the National Cancer Institute Common Toxicity Criteria, version 2.0. Tumor status was assessed at baseline and after every two cycles of therapy with computed tomography (CT) scans and/or positron emission tomography (PET)/CT scans. Tumor response assessed by computed tomography (CT) scans was determined in accordance with standard World Health Organization (WHO) criteria. 10 Additional details on patient selection and assessment are provided in the Supplementary Methods. Dr. J. Jack Lee designed the clinical trial and analyzed the data. This study was approved by the University of Texas MD Anderson Institutional Review Board, the NIH Recombinant DNA Advisory Committee, and the FDA. All patients provided written informed consent prior to entry into the study.

Example 2 FUS1/TUSC2 Expression Vector

This pLJ143/KGB2/FUS1 plasmid vector (FIG. 1A) includes a mammalian gene-expression cassette driven by a CMV minimum promoter with an E1 enhancer at the 3' end and a BGH-poly A signal sequence at the 5' end to ensure the efficient expression of the transgene in vivo. The kanamycin-resistance gene was chosen as the selectable marker to avoid development of antibiotic-resistance in patients. A minimum pMB1 origin of replication (ori) sequence is used to drive high-copy replication and production of the plasmid in the bacterial host strain DH5a. The plasmid backbone is minimal to ensure a higher yield of plasmid DNA production and a higher concentration of recombinant plasmid DNA per plasmid DNA preparation. The entire DNA sequence of the plasmid vector was determined by automated DNA sequencing using the DNA Sequencing Core Facility at the M.D. Anderson Cancer Center. The complete DNA sequence of pLJ143/KGB2/FUS1 plasmid vector is provided as SEQ ID NO: 1. Specific elements of the vector are detailed below.

E1 Enhancer (bases 4-473): The E1 enhancer is a transcriptional enhancer for adenoviral gene E1 protein and is derived from the adenoviral shuttle vector constructed by Grahm et al. E1 enhancer is used to enhance transcription of gene of interest under the control of CMV promoter in mammalian cells.

CMV Promoter (Bases 474-1171):

The CMV promoter is derived from the adenoviral shuttle vector constructed by Grahm et al. The CMV promoter is covered under U.S. Pat. Nos. 5,168,062 and 5,385,839, owned and licensed by the University of Iowa Research Foundation (Iowa City, Iowa 52242). The human cytomegalovirus (CMV) promoter has been cloned, sequenced, and used to construct a series of mammalian cell expression plasmid (Chapman et al., 1991). A high level of gene expression can be achieved under the control of CMV promoter in mammalian cells.

BGH Polyadenylation Signal (Bases 1652-1877):

BGH polyadenylation signal sequence is derived from the adenoviral shuttle vector constructed by Grahm et al. The BGH polyadenylation sequence is covered under U.S. Pat. No. 5,122,458 and licensed by Research Corporation Technologies (Tucson, Ariz.). Transcriptional termination by RNA polymerase III at the 3' end of eukyrotic genes requires two distinct cis-active elements, a functional poly (A) signal and a downstream transcription pause site. The BGH poly A signal has been widely used as a transcription termination signal for mammalian gene expression in vitro and in vivo (Eggermont et al., 1993; Goodwin et al., 1992)

Kanamycin Resistance Gene (Bases 2049-2934):

The antibiotics Kanamycin resistance gene is derived from the pVAX1 plasmid vector from Invitrogen (Carlsbad, Calif.). The kanamycin resistance gene is used as selective marker for plasmid production in bacterial $E.$ $coli.$ in the presence of antibiotics Kanamycin.

pMB1 Origin (Bases 2995-3734):

The high copy number plasmid pMB1 replication origin sequence is derived from the pMG plasmid vector from Invivogen (San Diego, Calif.). The minimal pMB 1 origin is used to reduce plasmid size and drive a high copy number replication of plasmid DNA in $E.$ $coli.$ Example 3 Plasmid Preparation The pLJ143/KGB2/FUS1 plasmid vector was produced under GMP conditions at the Baylor College of Medicine Center for Cell and Gene Therapy (Houston, Tex.) and the Beckman Research Institute of the City of Hope (Duarte, Calif.).

A 1 mL vial of the pLJ143 master cell bank stock was aseptically inoculated into 500 mL sterile Terrific Broth with 1.6% Glycerol (Teknova: 1.2% Tryptone, 2.4% yeast extract, 1.6% glycerol. 1× phosphate buffer) supplemented with Kanamycin (Sigma) and grown overnight (15-18 hours) at 37° C. This was then used to inoculate 20 L of Terrific Broth in a New Brunswick scientific BioFlo IV 4500 fermentor, operating at 37° C., 250-300 rpm, 20-30% $CO_2$. Cells are harvested by centrifugation, washed once (1 mL buffer per g wet cell paste) with Alkaline Lysis Solution I (Teknova: 50 mM Glucose, 25 mM Tris-HCl, pH 8.0, 10 mM EDTA, pH 8.0, sterile solution) and frozen at −80° C.

The cell pastes were removed from −80° C. storage and thawed in a 4° C. refrigerator overnight. The cell paste was mixed with Alkaline Lysis Solution I at 8 ml per gram of wet cell paste. The pLJ143 suspension was then mixed 1:1 (v/v) with Alkaline Lysis Solution II (Teknova: 200 mM NaOH, 1.0% SDS, sterile solution). After mixing, the material was allowed to lyse at room temperature between 8 and 10 minutes. Two volumes of Alkaline Lysis Solution III (Teknova: 3M potassium acetate, 1.18M formic acid, pH 5.5, sterile solution) were then added with the lysate, and mixed on ice to ensure complete neutralization and precipitation of host cell proteins, genomic host cell DNA and SDS. The neutralized cell lysate was clarified using a bucket centrifuge at 4000 rpm for 30 minutes at 4° C. The supernatant was decanted and clarified through a 1.2 mM PP2 filter.

This four step purification process does not require RNase enzyme, organic solvents, detergents, precipitants or animal derived components. The entire process is controlled with an Aekta Purifier (Amersham Bioscience) and Unicorn Software (Amersham Bioscience). All columns and packing material are from Amersham Bioscience. All column preparation and storage is as follows:

CIP: 0.5 M NaOH, 25° C. for 1 hour contact time
Depyrogenation: 100 ppm sodium hypochlorite pH 10, then 0.1-0.5N NaOH, pH13
Storage: 20% ethanol (aqueous solution)
Preparation for Use (Sanitization): Cell Culture Grade Water (US Pharmacopia), then Primed with Applicable Buffer Step 1: Concentration Using Hollow Fiber Filter (HFF)

The clarified lysate was first concentrated approximately 10-fold and equilibrated with using a 300,000 kDa nominal molecular weight cut-off (NMWCO) A/G Technology hollow fiber filter (HFF). The HFF was flushed with 4-L of Alkaline Lysis Solution III (3M potassium acetate, 1.18M formic acid, pH 5.5, sterile solution) and pooled with the concentrated lysate. A final volume of approximately 2-L is recovered, filtered with a 0.45 μm filter, and stored at 4° C. until the next step.

Step 2: Size Exclusion

RNA removal and buffer exchange by group separation using Sepharose 6 Fast Flow with BPG size exclusion column. UF Concentrate is applied to the column in batches of 0.3 column volumes (CV) to change the buffer to Buffer A (2M $(NH_4)SO_4$, 10 mM EDTA, 100 mM Tris-HCl, pH 7.0). Simultaneously this procedure also removes RNA and other contaminants. The void fractions are stored at 4° C. and then pooled for the next step.

Step 3: Selective Capture of Supercoiled Plasmid DNA by Thiophilic Aromatic Adsorption Chromatography.

Supercoiled plasmid DNA is separated from open circular plasmid DNA and remaining contaminants such as residual genomic DNA and RNA. The pooled void fraction (from Step 2) is subsequently applied on the XK50 Affinity column packed with PlasmidSelect and equilibrated in the same Buffer A. The column is washed and supercoiled plasmid DNA is eluted with Buffer B (1.4M NaCl, 2.0 M $(NH_4)SO_4$, 10 mM EDTA, 100 mM Tris-HCl, pH7.0.). Fractions are stored at 4° C. prior to next step. Fractions are pooled for step 4. then diluted with four volumes of water for the next step.

Step 4: Polishing and Concentration with SOURCE 30Q

Endotoxins are further removed and at the same time, the supercoiled plasmid DNA preparation is concentrated by ion exchange chromatography. The fraction (from step 3) containing supercoiled plasmid DNA is diluted with 4 volumes of pharmaceutical grade water and loaded on a XK26 ion exchange column packed with SOURCE 30Q. The column is equilibrated Buffer C (0.4 M NaCl, 10 mM EDTA, 100 mM Tris-HCl, pH 7.0) and eluted with a linear gradient, Buffer D (1.0 M NaCl, 10 mM EDTA, 100 mM Tris-HCl, pH 7.0). The fractions are then pooled and filtered through a 0.22 μm filter.

PlasmidSelect is the key protocol component since it interacts differentially with nucleic acids by thiophilic aromatic adsorption in the presence of water structuring salts. This enables the topoisomere-selective purification of native supercoiled plasmid DNA and removal of damaged, nicked or open circular DNA by simple adjustment of chromatographic conditions. A group separation for removal of RNA prior to application on the column optimizes the capacity of PlasmidSelect for binding of the supercoiled form of plasmids. Furthermore, group separation with Sepharose 6 Fast Flow greatly reduces the risk of precipitation during addition of ammonium sulfate and limits the variation in initial salt concentration that can influence selectivity, thus giving the process considerable robustness.

Ethanol precipitation was used to concentrate the pLJ143 to 5 mg/ml. A 3.0 M sterile NaCl solution was used to increase the NaCl concentration of the pLJ143 solution to 0.15M. Ethanol was added into the pLJ143 solution in a 2:1 ratio to give a final ethanol concentration of 67%. The pLJ143 suspension was stored at −20° C. overnight to allow for complete precipitation. The next morning, the pLJ143 was recovered by centrifugation. The pLJ143 pellets were further washed with 70% ethanol and allowed to air dry aseptically in a laminar flow hood for approximately one hour. Dried pellets were frozen at −80° C. until purification of wet paste from all fermentation runs was complete. The pLJ143 was then reconstituted at 5 mg/ml in sterile endotoxin, RNAse, DNAse free water. All work is performed in a class 100 biosafety cabinet.

Product was filled into 1.2 ml crimp cap glass vials with semi-automated dispensing pipette in a class 100 biosafety cabinet. The fill volume is either 0.3 ml, 0.5 ml, or 1.0 ml. The target plasmid DNA concentration was 5 mg/mL. The final product is stored at −80° C. Plamid purity tests and quality control standards are shown in Table 1 below.

TABLE 1

Plasmid quality control specifications.

| Characteristics | TEST | Specifications |
|---|---|---|
| Appearance | | Clear, Colorless |
| pH | pH meter | 5.5 ≤ pH ≥ 8.0 |
| DNA Identity | DNA Homogeneity | ≥90% Appropriate form DNA |
| | Supercoiled DNA | ≥95% |
| | Restriction Map | Restriction Digestion pattern Identical to the reference |
| | Bio-activity by cell transfection and Western-blotting | Positive for Transgene Expression |
| Purity | A260/280 Ratio | 1.7-2.0 |
| | A260/230 Ratio | 2.0-2.2 |
| | Protein Contamination | <10 μg/mg DNA |
| | Host E. coli Genomic DNA Contamination | <1% (w/w) of total detectable nucleic acid by qPCR |
| | Residual RNA Contamination | <5% (w/w) of total detectable nucleic acid (0.5 φg load) by gel |
| | Residual Isopropanol and ethanol | by GC analysis |
| | Residual Antibiotics (kanamycin) | Undetectable (<3.0 φg/ml) |
| | Ammonia | ≤1 mg/mL of final formulated plasmid DNA |
| | Sulfate | ≤1 mg/mL of Final Formulated Plasmid DNA |
| | Endotoxin | <5 EU/mg DNA by LAL Assay |
| Sterility | Bacterial (CFR) | Negative |
| | Fungal | Negative |
| | In vitro Adventitious Virus | Negative |
| Concentration | O.D. At 260 nm | 1 to 5 mg/mL/vial ± 0.5% per vial |
| Biologic Activity | Transfection in H1299 cells | Protein expression by Western Blot |

Example 4 Nanoparticle Preparation

DOTAP GMP grade was purchased from Avanti Polar Lipids, Inc. (Alabaster, Ala.) and cholesterol GMP grade was purchased from Sigma-Aldrich (St. Louis, Mo.). A ratio of 20 mM DOTAP:18 mM cholesterol was used for preparation of the nanoparticles. The reagents were mixed and the dry lipids dissolved in purified GMP grade chloroform. A Buchi rotary evaporator was used to form a dry lipid film. Further drying was performed under a vacuum in a Labconco Freeze dry system. The film was resuspended in sterile 5% dextrose in water. After sonication the following day under aseptic conditions the lipids are sequentially extruded through a series of sterile Whatman filters from 1 µm to 0.1 µm in pore size.

The diluted plasmid DNA and diluted nanoparticle stock were mixed in equal volumes to a final concentration of 4 mM DOTAP and 0.5 mg/ml of DNA. Prior to treatment the assigned dose was diluted in 100 ml D5W. A negative gram stain was required prior to treatment.

Example 5 Therapy Protocol and Results

Thirty-one patients were enrolled in the study at a single institution. Patient characteristics are described in Table 2.

TABLE 2

Baseline Characteristics of Patients

| Characteristic | No. of Patients (%) (n = 31) |
|---|---|
| Median age, years (range) | 60 (43-76) |
| Sex | |
| Male | 16 (51.6%) |
| Female | 15 (48.4%) |
| ECOG performance status | |
| 0 | 4 (12.9%) |
| 1 | 27 (87.1%) |
| Histology | |
| Adenocarcinoma | 11 (35.5%) |
| Bronchioalveolar carcinoma | 1 (3.2%) |
| Squamous cell carcinoma | 3 (9.7%) |
| Non-small cell carcinoma, NOS | 11 (35.5%) |
| Small cell carcinoma | 5 (16.1%) |
| Prior Therapy | |
| Chemotherapy | 31 (100%) |
| Radiotherapy | 14 (45.2%) |
| Surgery | 11 (35.5%) |
| Prior Chemotherapy regimens | |
| 1 | 9 (29%) |
| 2 | 9 (29%) |
| >2 | 13 (41.9%) |
| Number of doses received | |
| 1 | 8 (26%) |
| 2 | 19 (61%) |
| >3 | 4 (13%) |

Abbreviations: ECOG, Eastern Cooperative Oncology Group; NOS, not otherwise specified A total of 74 cycles of DOTAP:chol-TUSC2 were administered, with a median of 2 cycles (range, 1 to 12 cycles) per patient. Patients were treated at 6 dose levels ranging from 0.01 to 0.09 mg/kg. The dose escalation scheme, including number of patients, number of cycles, DLTs, and grade 2 toxicities judged to be related to DOTAP:chol-TUSC2 are listed in Table 3.

TABLE 3

Dose-Escalation Scheme

| Cohort No. | Dose level (mg/kg) | No. of Patients | No. of cycles | No. patients with DLT | Grade 2 toxicity (No. patients) |
|---|---|---|---|---|---|
| 1 | 0.02 | 3 | 9 | 0 | Fever (1) |
| 2 | 0.03 | 3 | 6 | 0 | 0 |
| 3[1] | 0.01 | 3 | 4 | 2; G3 fever (n = 2), G3 hypotension (n = 1) | Fever (1) |
| 4* | 0.01 | 3 | 9 | 0 | 0 |
| 5* | 0.02 | 3 | 6 | 0 | 0 |
| 6* | 0.04 | 3 | 6 | 0 | 0 |
| 7* | 0.06 | 3 | 6 | 0 | ALT (1), neuropathy (n = 1) |
| 8* | 0.09 | 3 | 5 | 1; G3 hypophosphatemia | Fever (1) |
| 9* | 0.06 | 3 | 16 | 0 | Hypophosphatemia (1), nausea (1), myalgia (1) |
| 10* | 0.06 | 3 | 5 | 1; G3 hypophosphatemia | Fever (1), myalgia (1), hypophosphatemia (1), |
| 11 | 0.06 | 1 | 2 | 0 | 0 |

Abbreviations: G3, grade 3; ALT, alanine aminotransferase elevation
[1]This cohort did not receive dexamethasone or diphenhydramine premedications
*Cohorts used to determine maximum tolerated dose (MTD)

The first patient in cohort 1 (receiving 0.02 mg/kg) developed grade 2 fever within 3 hours of the DOTAP:chol-TUSC2 infusion. The subsequent patients in cohorts 1 and 2 were given dexamethasone and diphenhydramine prior to receiving DOTAP:chol-TUSC2, and no grade 1 or higher toxicites were observed. However, after discussions with the FDA, it was mandated that the next patient cohort receive DOTAP:chol-TUSC2 at a lower dose level of 0.01 mg/kg without dexamethasone or diphenhydramine premedication. All three patients developed grade 2 or 3 fever and one patient developed grade 3 hypotension. The FDA then allowed the protocol to be amended to require dexamethasone and diphenhydramine premedications beginning with the next cohort (patient 10), starting at a dose level of 0.01 mg/kg. Due to this amendment, it was decided not to use the toxicity data from the first nine patients for MTD determination, and a subgroup of 21 patients enrolled between Sep. 28, 2006 and Oct. 29, 2009 were used to determine the final MTD.

The only subsequent DLTs observed were grade 3 hypophosphatemia in two patients with one at 0.06 mg/kg and another at 0.09 mg/kg. In both cases the patients had either grade 1 or 2 fevers and the hypophosphatemia was an incidental laboratory finding. The MTD was determined to be 0.06 mg/kg. As listed in Table 2, grade 2 toxicities included myalgias, hypophosphatemia, fever, nausea, and transaminase elevation.

Peripheral Blood Mononuclear Cell (PBMC) Cryo-Preservation and Fluorescent Activated Cell Sorter Analysis (FACS)

Patient blood samples were collected in capped glass tubes containing ficoll at room temperature (RT). Blood samples were centrifuged at 3500 rpm at RT for 30 minutes in a swing-out rotor. Separated plasma and lymphocytes were collected separately in a centrifuge tubes. An equal volume of PBS was added to the lymphocyte-containing tube and centrifuged at 900×g at RT for 10 min. After centrifugation, the supernatant was removed. The cell pellets were washed again with the same volume of PBS as the first wash. The cell suspension was centrifuged at 700×g for 10 minutes, and the supernatant was removed. Cell concentrations were determined and adjusted to a final concentration of 5×106 cells/mL with cell-freezing medium containing 10% of DMSO and 90% fetal bovine serum. Eight hundred uL aliquots of 5×106/mL lymphocytes were transferred into cryogenic vials. The PBMC-containing cryogenic vials were stored in a −80° C. freezer for 48 h and then transferred to a liquid nitrogen freezer.

Frozen PBMC were thawed immediately in a 37° C. water bath, then washed with 10 ml of RPMI1640 with 10% FBS. The cells were then lysed with 1×BD FACS Lysing Solution (BD Biosciences, San Jose Calif.) for 10 minutes at room temperature. The cells were centrifuged at 400×g for 10 minutes, followed by treatment with 1×FACS Permeabilizing Solution 2 (BD Biosciences, San Jose, Calif.) for 10 minutes at room temperature. The cells were then rinsed with PBS containing 1% FBS and centrifuged for 10 minutes at 400×g and re-suspended in 400 µL of PBS with 1% FBS. Aliquots were made in the required number of BD Falcon 5 mL polystyrene tubes. Antibodies (BD, Franklin Lakes, N.J.) were then added to each tube according to the table listed below under the fluorescent dye in bold letters:

| FITC | PE | PerCP | APC |
|---|---|---|---|
| IgG1 | IgG1 | CD14 | IgG1 |
| TNF-a | IL-6 | CD14 | IL-15 |
| IL-1b | IFN-g | CD14 | |
| IL-8 | | CD14 | |

The cells were incubated with antibodies for 30 minutes at room temperature protected from light, washed with PBS containing 1% FBS, re-suspended in 250 uL of PBS with 1% paraformaldehyde, and analyzed by 6-color flow cytometry (LSR11, BD). The cytokine data was analyzed using FlowJo software (Tree Star, Inc., Ashland, Oreg.).

Figure 11A:
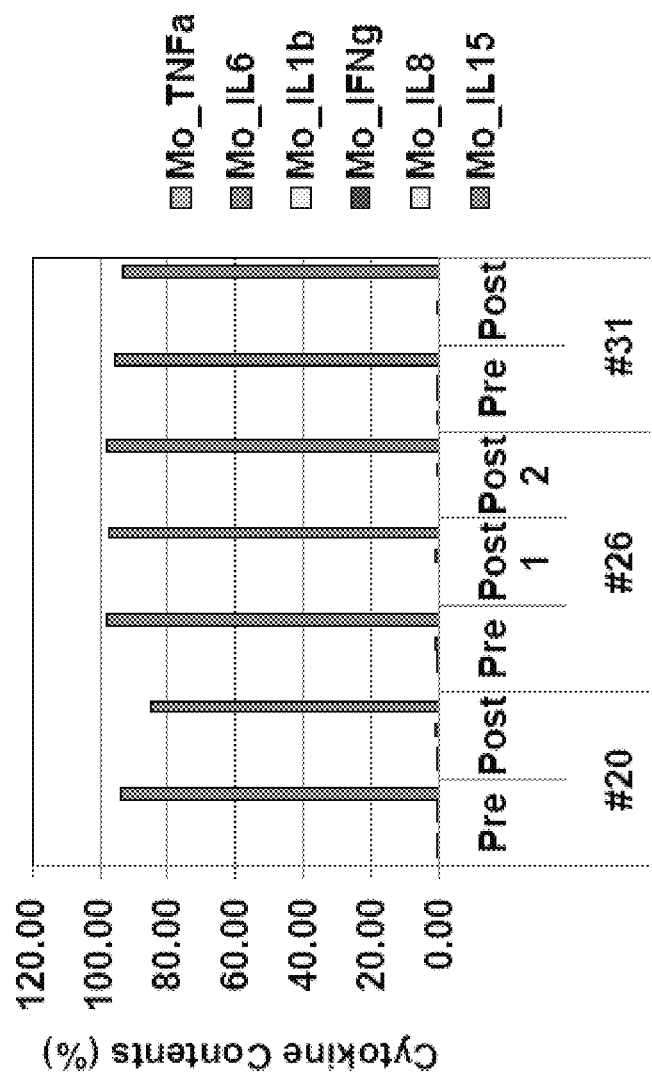
FIG. 11A-B: FACS analysis was used to measure intracellular levels of TNF-a, IL-15, IL-6, IL1b, IFNg, and IL-8 in peripheral blood monocytes and lymphocytes in pretreatment and posttreatment samples 24 hours after administration of the DOTAP:chol-TUSC2. For one patient peripheral blood mononuclear cells (PBMC) were obtained 14 months following 12 treatments (Post 2). Only IL-15 showed detectable levels in lymphocytes and monocytes. No statistically significant increases in the post-treatment samples were observed for any cytokine All comparisons are by two-tailed paired Student's t-test.
Figure 11B:
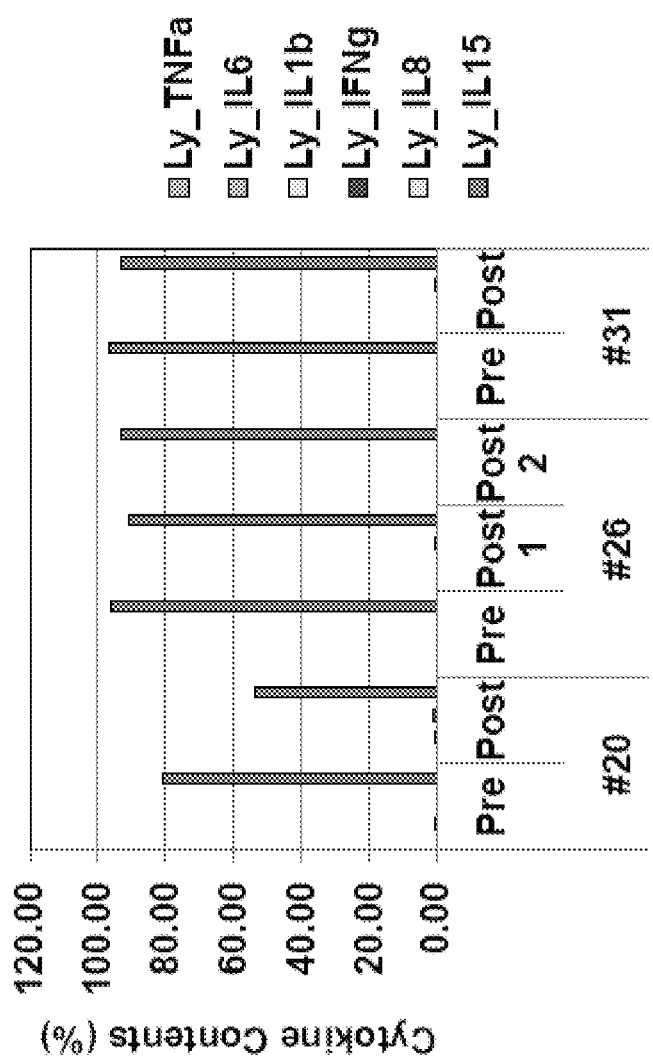

Results of these studies showed that intracellular levels of TNF-a, IL-15, IL-6, IL1b, IFNg, and IL-8 in peripheral blood monocytes and lymphocytes remained unchanged 24 hours after treatment (FIG. 11A-B).

Antibodies to Single and Double Stranded DNA

Serum antibodies to single and double stranded DNA were determined by an ELISA assay performed at the Mayo Clinic Department of Laboratory Medicine and Pathology, Rochester, Minn. For single stranded DNA antibodies a value of <69 U/ml is considered negative for antibody detection. For double stranded DNA antibodies a value of <1 is considered negative for antibody detection.

Results showed that antibodies to single and double stranded DNA were not detected 14 months after completion of 12 cycles of therapy in patient 26.

Example 6 TUSC2 RNA Expression

All specimens were blinded for patient identity, for clinical information and for specimen timing (pre- vs post-treatment) during all studies. Ectopic expression of the TUSC2 gene in patient biopsy samples was analyzed using a TaqMan™ based quantitative real time reverse transcriptase-polymerase chain reaction (RT-PCR) (Applied Biosystems, Foster City, Calif.) that enables quantification of gene expression from a limited amount of starting material as detailed below.

RNA was isolated using RNeasy™ minikit from Qiagen (Valencia, Calif.) following the manufacturer's instructions. The fine-needle biopsy tissues that were immediately fixed in RNAlater (Ambion, Austin, Tex.) were washed once with cold PBS and then the total RNAs were isolated with (reagent and methods). The quality of the purified RNA was analyzed using an Agilent 2100 Nano Bioanalyzer (Agilent Technologies, Santa Clara Calif.). Reverse transcription was done using a High Capacity cDNA Reverse Transcription Kit (Applied Biosystems, Foster City, Calif.) with Multi-Scribe Reverse Transcriptase for two hours at 37° C. in a thermal cycler according to the manufacturer's instructions. The PCR reaction was setup with 10 ml of 2×TaqMan™ gene expression master mix containing the polymerase, buffer and dNTPs, 1 ml of 20×TaqMan™ gene expression assay solution containing primers, probe, and 5 ml of cDNA template, and 4 ml of sterile distilled water. The primers and probes used were specific to the exogenous TUSC2 transcripts expressed through the plasmid gene expression cassette (Forward primer: 5' GGA CCT GCA GCC CAA GCT 3' (SEQ ID NO: 3) and Reverse primer: 5' GCC CAT GTC AAG CCG AAT T 3' (SEQ ID NO: 4), and TaqMan™ probe: 6-FAM-CGA GCT CGG ATC CAC TAG TCC AGT GTG-TAMRA; SEQ ID NO: 5) to avoid detection of endogenous TUSC2 mRNA. PCR analysis was performed using a 7500 Real-Time PCR System (Applied Biosystems, Foster City, Calif.) and run with an absolute quantification mode with a standard curve. The DNA amount values were then used for the calculation of TUSC2 copy numbers using the University of Rhode Island's website available on the world wide web at uri.edu/research/gsc/resources/cndna.html (URI Genomics & Sequencing Center Calculator for determining the number of copies of a template).

TUSC2 transgene RNA expression by RT-PCR was not detected in pre-treatment biopsies (Table 4). Five of six post-treatment biopsies showed expression of the TUSC2 transgene. In a seventh patient (Patient No. 31), TUSC2 mRNA was detected by RT-PCR transgene specific primers included in the qRT Profiler Apoptosis PCR Array and was detected only in the post-treatment sample (see below). Expression was not detected in pre- and post-treatment peripheral blood lymphocytes collected at the time of the biopsies.

TABLE 4

Real Time RT-PCR detection of TUSC2 gene expression in patients.

| Patient Number | Dose (mg/kg) | Site of Tumor Biopsy | Treatment | Tumor TUSC2 Gene Expression (pg/ug tissue) | Tumor TUSC2 Copy Number (copies/ug tissue) | Lymphocyte TUSC2 Gene Expression (pg/µl) |
|---|---|---|---|---|---|---|
| 1 | 0.02 | Lung | Pre-treatment | 0 | 0 | NA[1] |
| | | Lung | Post-treatment | $2.0 \times 10^{-5} \pm 2.20 \times 10^{-10}$ | 4.44 | NA |
| 7 | 0.01 | Lung | Pre-treatment | 0 | 0 | NA |

TABLE 4-continued

Real Time RT-PCR detection of TUSC2 gene expression in patients.

| Patient Number | Dose (mg/kg) | Site of Tumor Biopsy | Treatment | Tumor TUSC2 Gene Expression (pg/ug tissue) | Tumor TUSC2 Copy Number (copies/ug tissue) | Lymphocyte TUSC2 Gene Expression (pg/μl) |
|---|---|---|---|---|---|---|
|  |  | Lung | Post-treatment | $3.6 \times 10^{-6} \pm 9.1 \times 10^{-7}$ | 0.89 | NA |
| 13 | 0.02 | Lung | Pre-treatment | 0 | 0 | NA |
|  |  | Lung | Post-treatment | $3.0 \times 10^{-5} \pm 1.71 \times 10^{-8}$ | 6.22 | NA |
| 20 | 0.06 | Liver | Pre-treatment | 0 | 0 | 0 |
|  |  | Liver | Post-treatment | 0 | 0 | 0 |
| 24 | 0.09 | Subcutaneous nodule | Pre-treatment | 0 | 0 | 0 |
|  |  | Subcutaneous nodule | Post-treatment | $8.0 \times 10^{-6} \pm 2.33 \times 10^{-8}$ | 1.90 | 0 |
| 25 | 0.06 | Lung | Pre-treatment | 0 | 0 | 0 |
|  |  | Lung | Post-treatment | $4.0 \times 10^{-5} \pm 1.66 \times 10^{-9}$ | 8.76 | 0 |

[1]Specimens not available

Example 7 TUSC2 Protein Expression

Figure 2A:
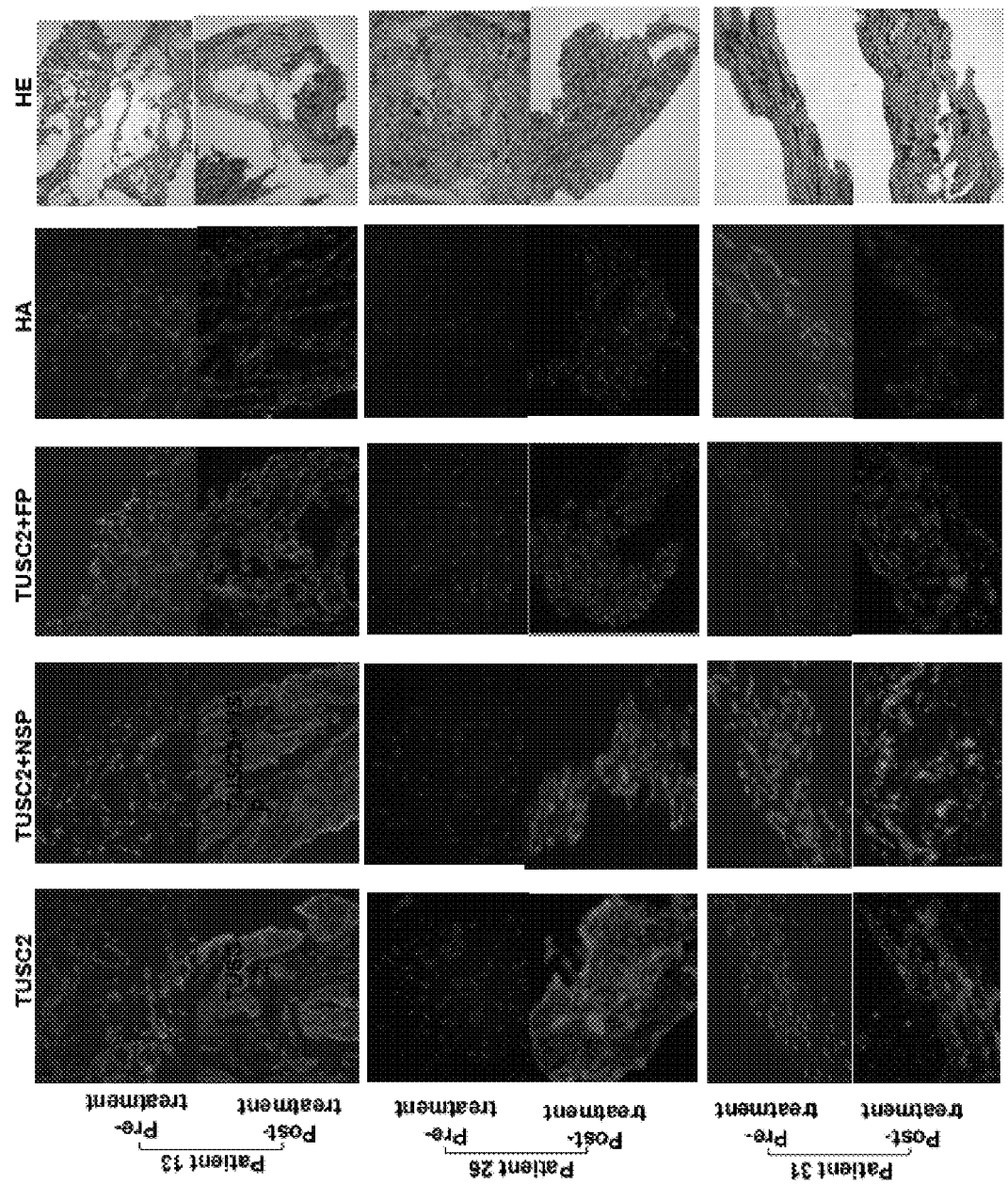
FIG. 2A-B.
Figure 2B:
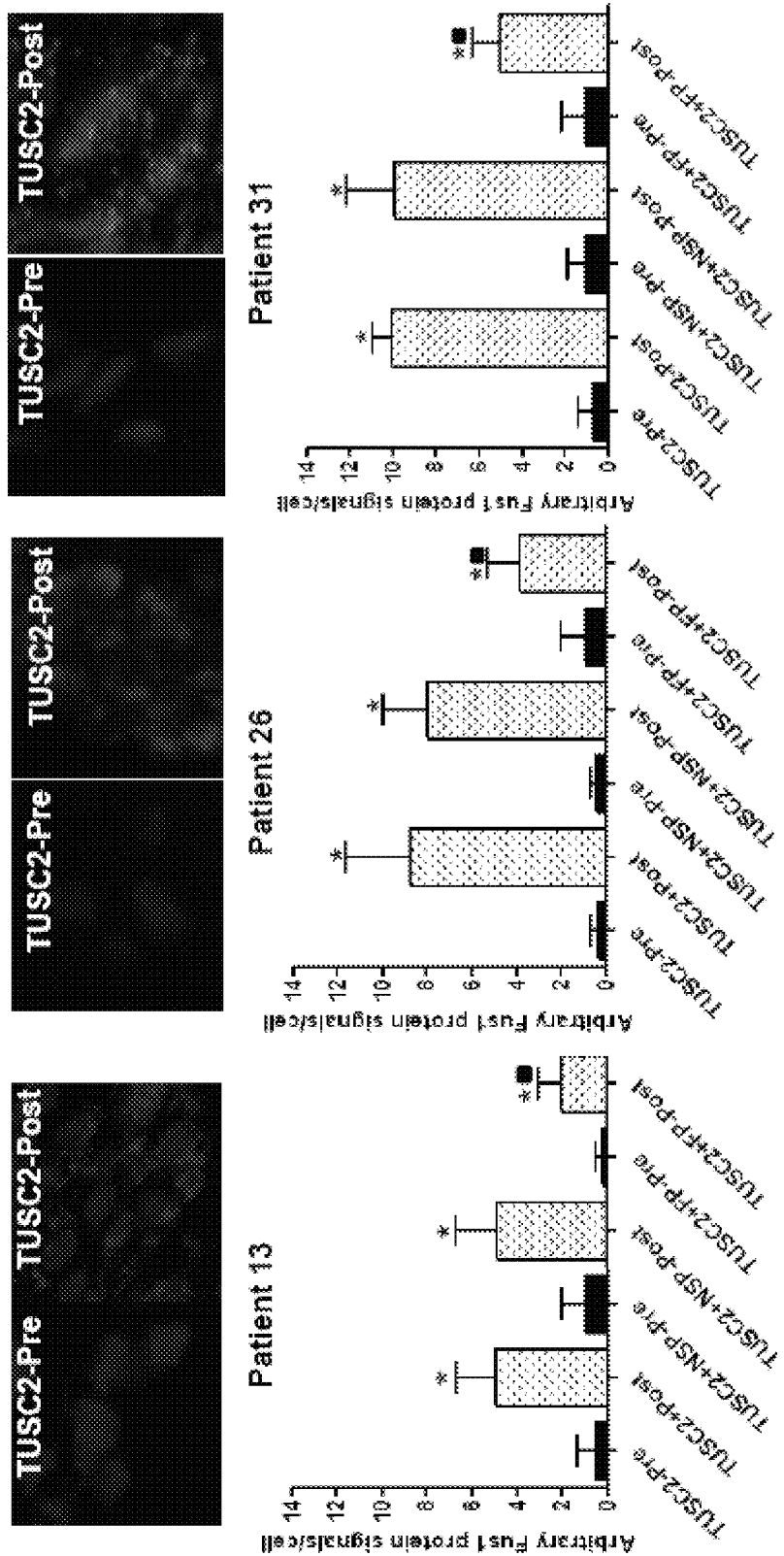

Anti-TUSC2 antibody was used to detect TUSC2 protein expression in pre- and post-treatment lung tumor biopsies from patients 13, 26 and 31 (FIG. 2B). Specifically, Duolink kits from Olink Biosciences (Uppsala, Sweden) were used. These kits are based on PLA technology and the rolling circle amplification (RCA) reaction wherein a pair of oligonucleotide labeled secondary antibodies (PLA probes) generates a signal only when the two PLA probes have bound in close proximity, either to the same primary antibody or two primary antibodies that have bound to the sample in close proximity. The signal from each detected pair of PLA probes is visualized as an individual fluorescent spot. Signals can be quantified (counted) and assigned to a specific subcellular location based on microscopy images.

The samples were incubated with primary antibodies that bind to the protein(s) to be detected. Secondary antibodies conjugated with oligonucleotides (PLA probe MINUS and PLA probe PLUS) were then added to the reaction and incubated. The ligation solution, consisting of two oligonucleotides and ligase, is added and the oligonucleotides hybridize to the two PLA probes and join to form a closed circle if they are in close proximity. The amplification solution, consisting of nucleotides and fluorescently labeled oligonucleotides, was added together with polymerase. The oligonucleotide arm of one of the PLA probes acts as a primer for a rolling-circle amplification (RCA) reaction using the ligated circle as a template, generating a concatemeric (repeated sequence) product. The fluorescently labeled oligonucleotides then hybridizes to the RCA product. The signal was visible as a distinct fluorescent spot that can be analyzed by fluorescence microscopy. In order to detect posttreatment TUSC2 protein expression, a single antibody (TUSC2) raised in rabbits and oligo probes (plus and Minus) with rabbit secondary antibodies were used. In situ PLA was performed as per the recommendations of the manufacturer with minor modifications and also including appropriate controls. The experiments were carried out in a blinded setting. Patient biopsy tissues preserved in RNAlater™ were washed in 50 ml of cold PBS for 30 minutes at 4° C. before using OCT to prepare frozen blocks to cut slides. The slides with were then fixed with 4% paraformaldehyde and permeabilized with methanol for 20 minutes each. The tissues were blocked for 30 min at 37° C. in a humidified chamber with the blocking buffer provided in the kit and later incubated with anti-rabbit TUSC2 primary antibody overnight at 4° C. The following day, the primary antibodies were washed and tissues incubated with oligo-linked secondary antibodies (anti-rabbit PLA probes plus and minus). Hybridization, ligation, amplification and detection were then performed according to the manufacturer's instructions. For non-specific control, rabbit HA tag antibodies were used in the place of TUSC2 antibody. For competition experiments, the synthetic oligopeptide (GASGSKARGLWPFASAA; SEQ ID NO: 2) derived from the N-terminal amino-acid sequence of the TUSC2 protein that was used to develop anti-TUSC2 polyclonal antibody in rabbits was used (Ito et al., 2004).

The number of in situ proximity ligation signals was counted using the freeware software Blobfinder (available on the world wide web at cb.uu.se/~amin/BlobFinder). Nuclei were visualized by DAPI staining and used for cell count. The protein expression level was quantified by counting all signals (fluorescent spots) obtained from one image divided by the number of cells in the image, to derive the average signals/cell. Background subtraction was them applied with the pre-treatment samples.

Results of these studies are shown in FIG. 2A-B and demonstrated that both post-treatment biopsies showed a high level of TUSC2 protein with absence of TUSC2 protein on the paired pre-treatment biopsies. A non-specific control antibody showed only background staining. Pre-incubation of the TUSC2 antibody with the specific TUSC2 peptide used to immunize for antibody production, but not a non-specific peptide, was able to significantly reduce TUSC2 fluorescence in the post-treatment biopsies

Example 8 Effects on the Apoptosis Pathway

The expression of major genes in apoptosis signaling pathways in pretreatment and posttreatment needle biopsy specimens were quantified using a qRT Profiler Apoptosis PCR Array with RT Nano PreAmp-mediated cDNA synthesis (SA Biosciences, Frederick, Md.). The quantitative apoptotic gene expression data were analyzed as detailed below and through the use of Ingenuity Pathway Analysis (IPA) Ingenuity Systems, (available on the world wide web at ingenuity.com).

For gene expression profiling experiments, the total RNAs were isolated from patient fine needle biopsies using Trizol (Invitrogen, Carlsbad, Calif.) reagent and purified using a RT2 qPCR-Grade RNA isolation kit from SA Biosciences (Frederick, Md.) according to the manufacturer's instructions. The purified RNA was then used to synthesize cDNA using RT2 Nano PreAmp cDNA Synthesis Kit from SA Biosciences (Frederick, Md.). This cDNA kit also involved pre-amplification of the cDNA target templates. The preamplified cDNA was applied onto a RT2 Profiler Apoptosis PCR array (SA Biosciences) for qPCR analysis using an ABI 7500 real-time PCR instrument (Applied Biosystems, Foster City, Calif.) according to the manufacturers' instructions. The expression level of the mRNA of each gene in the patient after treatment with DOTAP:chol-TUSC2 was normalized using the expression levels of housekeeping genes B2M, HPRT1, RPL13A, GAPDH, and ACTB. For data analysis, the comparative Ct method was used wherein the relative changes in gene expression were calculated using the $\Delta\Delta Ct$ (threshold cycle) method. This method first subtracts the ct (threshold cycle number) of the gene-average ct of the five housekeeping genes on the array (B2M HPRT1, RPL13A, GAPDH and ACTB) to normalize to the RNA amount. Finally, the $\Delta\Delta Ct$ was calculated as the difference between the normalized average ct of each gene on the array after DOTAP:chol-TUSC2 treatment and the normalized average ct of the pre-treatment control sample. This $\Delta\Delta Ct$ was then raised to the power of 2 to calculate the relative fold-change of gene expression after-treatment compared to pre-treatment. Genes that differed from pretreatment controls by more than two fold were considered significant and changes of gene expression levels larger than three-fold were shown as a scatter plot.

The expression of major genes in apoptosis signaling pathway in tumor fine needle biopsies from human lung cancer patients before and after systemic treatment with DOTAP:chol-TUSC2 nanoparticles were quantified using a qRT Profiler Apoptosis PCR Array with RT Nano PreAmp-mediated cDNA synthesis (SA Biosciences, Frederick, Md.). The quantitative apoptotic gene expression data were analyzed through the use of Ingenuity Pathway Analysis (IPA) Ingenuity Systems, (see, e.g., the world wide web at ingenuity.com). For the network and canonical pathway analysis, the quantitative PCR data set containing gene identifiers and corresponding expression fold change values was uploaded into the application. Each identifier was mapped to its corresponding object in Ingenuity's Knowledge Base (IKB). An expression fold change (posttreatment/pretreatment) cut-off of 3 was set to identify molecules whose expression was significantly differentially regulated. These molecules, called Network Eligible molecules, were overlaid onto a global molecular network developed from information contained in IKB. Networks of Network Eligible Molecules were then algorithmically generated based on their direct or indirect connectivity. The Network molecules associated with biological functions in IKB were considered for analysis. Right-tailed Fisher's exact test was used to calculate a p-value determining the probability that each biological function assigned to a given network is due to chance alone. Molecules from the data set that met the above gene expression fold changes cutoff were also considered for the canonical pathway analysis. The significance of the association between the data set and the canonical pathway was measured by a ratio of the total number of molecules from the data set that map to the pathway to the total number of molecules that map to the canonical pathway in IKB. A Fisher's exact test was used to calculate a p-value determining the probability that the association between the genes in the dataset and the canonical pathway is explained by chance alone.

Figure 1B:
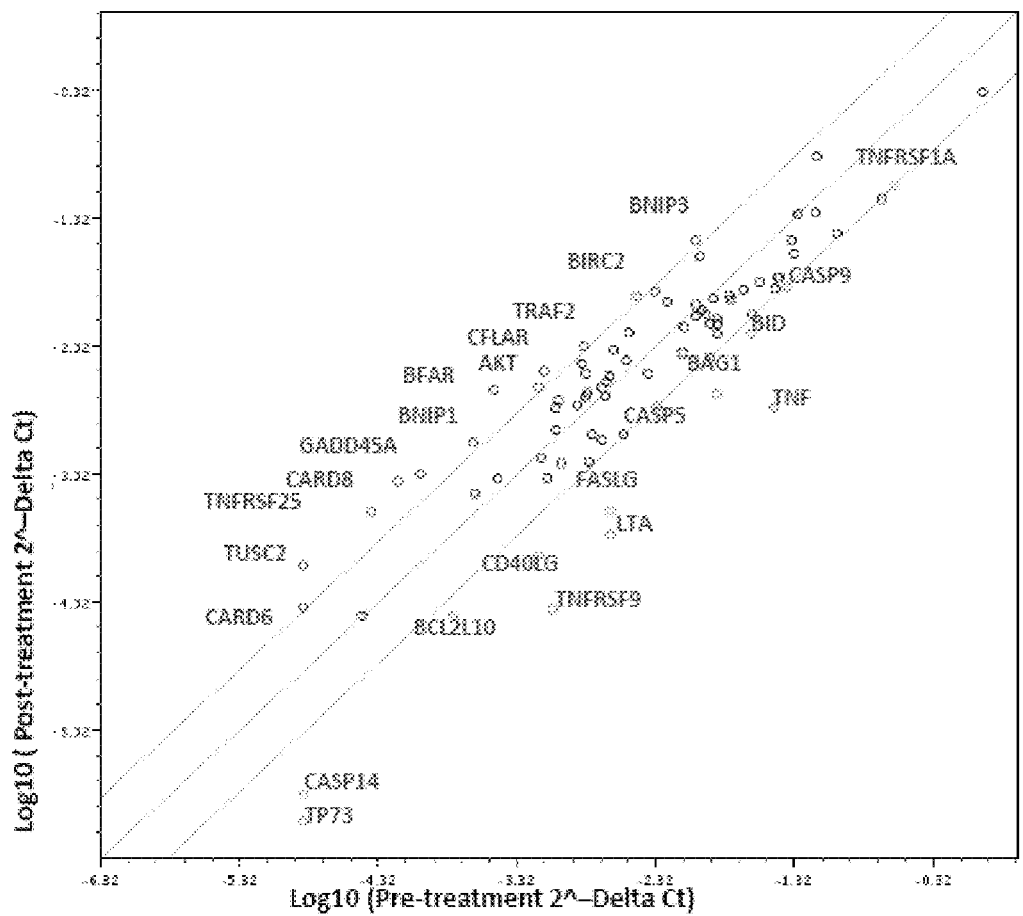
Figure 1C:
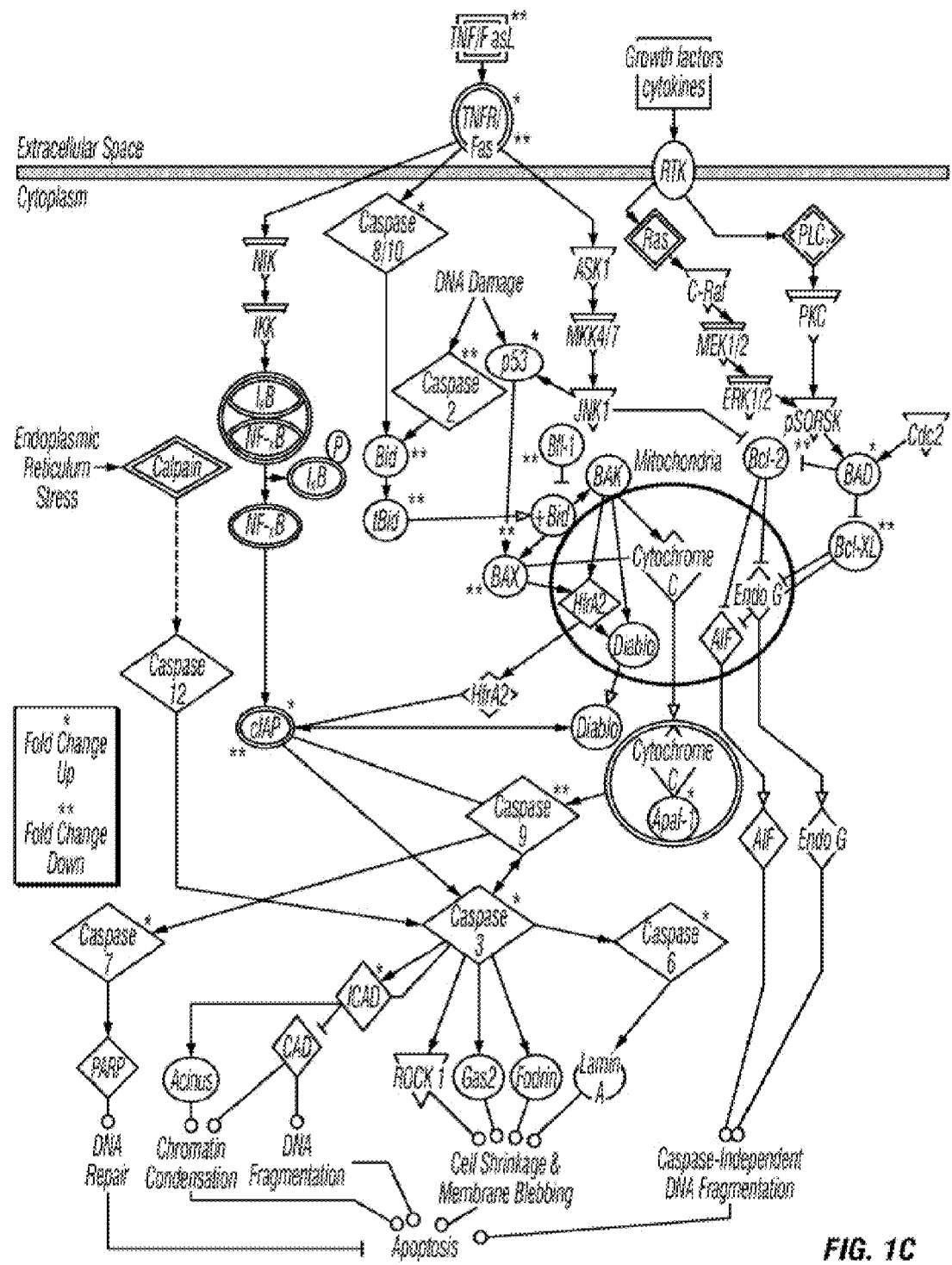

Significant differences in gene expression were detected by an apoptosis multiplex array between a pre and post-treatment biopsy from patient No. 31 whose tumor biopsies showed high levels of TUSC2 mRNA and protein post-treatment (FIG. 1B). The changes in gene expression and canonical apoptosis pathways in TUSC2-mediated apoptosis are graphically represented by FIG. 1C. Analysis methods are detailed below.

Example 9 Response and Survival

Twenty-three patients received two or more doses. Five patients achieved stable disease (range 2.6 to 10.8 months, median 5.0, 95% CI 2.0-7.6) and all other patients progressed. Two patients had reductions in primary tumor size of 14% and 26%. One patient with stable disease (patient 26) had evidence of a durable metabolic response on positron emission tomography (PET) imaging (FIG. 3) and received 12 cycles of therapy. The response was documented with PET scans performed after the second, fourth (FIG. 2), and sixth doses, all showing decreased metabolic activity with no changes in size or number of metastases by CT imaging. This patient remains alive on subsequent therapy 14 months after the final treatment with DOTAP:chol-TUSC2. Median survival for all patients was 8.3 months (95% CI 6.0-10.5 months,) and mean survival time was 13.2 months (95% CI 8.9-7.5 months) with a range of 2 to 21+ months).

Example 10 Predicting Clinical Benefit

Formalin fixed paraffin embedded (FFPE) pretreatment tumor samples obtained at initial diagnosis were available from 10 patients for assessment of baseline TUSC2 protein expression and AI. Only FFPE tissue could be used for this assay. All pre and posttreatment biopsies obtained specifically for this protocol were preserved in RNAlater (e.g., Patients 13 and 31) and could not be used for IHC.

TUSC2 Protein Expression

Formalin-fixed and paraffin-embedded (FFPE) tissue histology sections (5 µm thick) were baked overnight at 56°, deparaffinized, hydrated. Heat-induced epitope retrieval was performed in a DAKO antigen retrieval bath (10 mmol/L of sodium citrate, pH 6.0) at 121° C. for 30 seconds and 90° C. for 10 seconds in a decloaking chamber (Biocare, Concord, Calif.), followed by a 30-min cool down. Peroxide blocking was done with 3% $H_2O_2$ in methanol at room temperature for 15 min, followed by 10% bovine serum albumin in TBS-t for 30 min. The slides were incubated with primary antibody at 1:400 dilution for 65 min at room temperature. After washing with TBS-t, incubation with biotin-labeled secondary antibody for 30 min followed. The samples were incubated with a 1:40 solution of streptavidin-peroxidase for 30 min. The staining was then developed with 0.05% 3',3-diaminobenzidine tetrahydrochloride prepared in 0.05 mol/L of Tris buffer at pH 7.6 containing 0.024% $H_2O_2$ and then counterstained with hematoxylin. Formalin-fixed and paraffin-embedded lung tissues with normal bronchial epithelia were used as a positive control. For a negative control, the same specimens used for the positive controls were used, replacing the primary antibody with TBS-t. TUSC2 immunostaining was detected in the cytoplasm of normal epithelium and tumor cells. Immunohistochemical expression was quantified by two independent pathologists (M. I. Nunez and I. I. Wistuba) using a four-value intensity score (0, 1+, 2+, and 3+) and the percentage of the reactivity extent. A consensus value on both intensity and extension was reached by the two independent observers. A final consensual score was obtained by multiplying both intensity and extension values (range, 0-300).

TdT-Mediated dUTP Nick End Labeling (TUNEL) Assay and Apoptotic Index

FFPE tissue sections were stained using the DeadEnd™ Colorimetric TUNEL System (Cat G7130, Promega, Madison, Wis.) according to technical manufacture recommendation. The negative controls were performed omitting the rTdT enzyme in the TUNEL reaction mixture. The positive controls were performed treating the tissues with DNase I enzyme (Cat #M6101, Promega, Madison, Wis.) prior to the reaction mixture. 10 high-powered fields (×400) per case were assessed (at least 1000 cells). The apoptotic index (AI) was the total number of TUNEL positive cells per 1000 cells counted.

Figure 4:
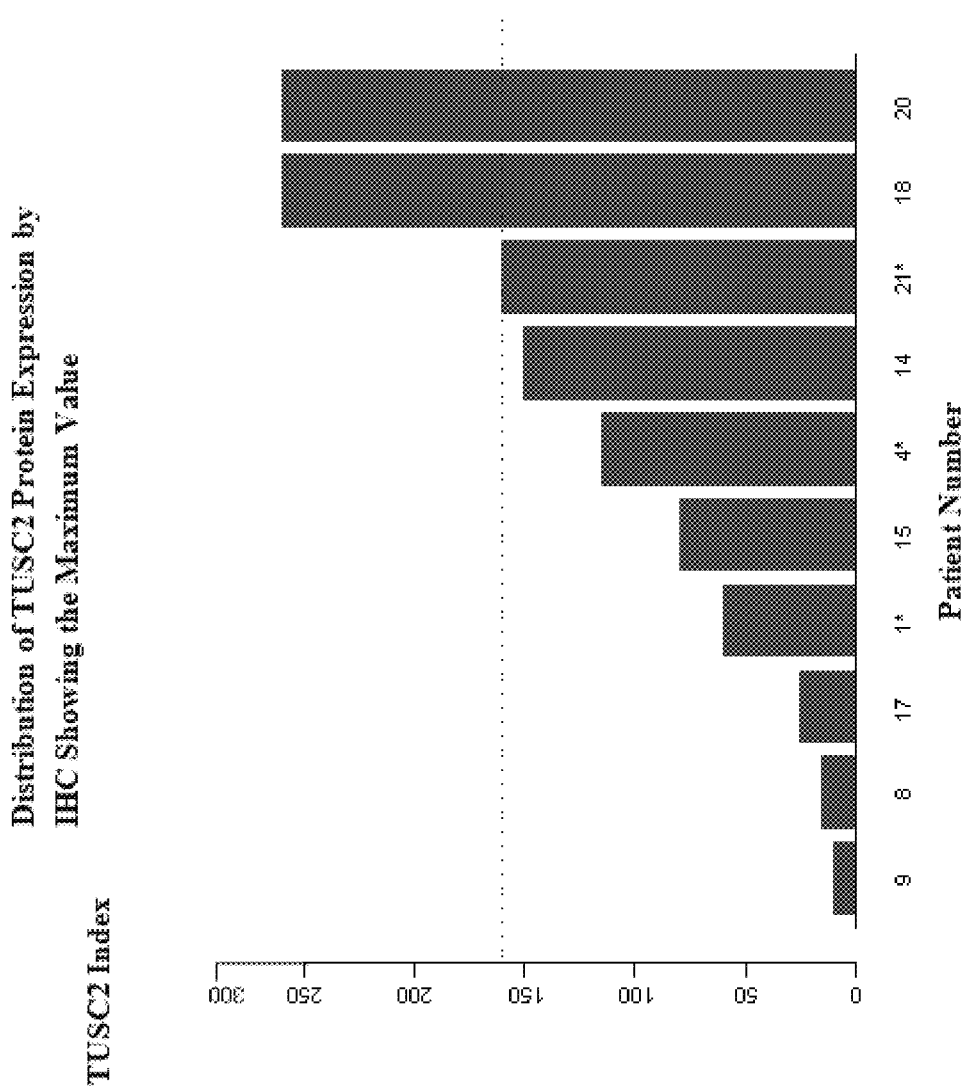
FIG. 4: TUSC2 expression was determined by immunohistochemistry. The dashed line indicates the level of TUSC2 expression in a biopsy of normal bronchial epithelium from one patient. The asterisks indicate patients who showed stable disease or minor response following treatment with DOTAP:chol-TUSC2 nanoparticles. No associations between the IHC marker with treatment outcome was observed.
Figure 5:
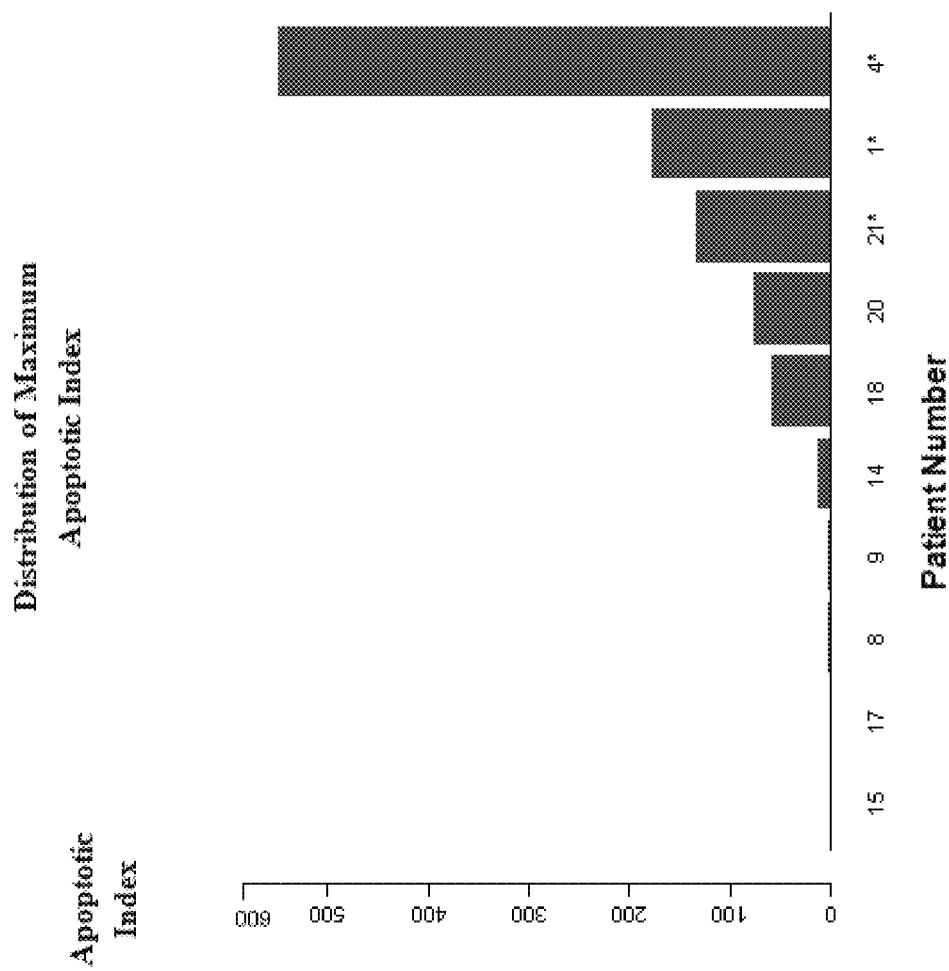
FIG. 5: Apoptotic index was determined by TUNEL staining. The asterisks indicate patients who showed stable disease or minor response following treatment with DOTAP: chol-TUSC2 nanoparticles. A maximum pretreatment apoptotic index of greater than 10% was associated with stable disease or minor response following treatment with DOTAP: chol-TUSC2 nanoparticles.

Results of these studies showed that TUSC2 protein expression in pretreatment FFPE tumor biopsies was low in most of the pretreatment biopsies with only two samples exceeding the level noted in normal bronchial epithelium (FIG. 4). The level of pretreatment TUSC2 protein expression did not correlate with clinical benefit. TUNEL staining was also performed in 10 pretreatment biopsies and an apoptotic index (AI) was calculated as detailed above. High levels of AI (>10%) were associated with achieving a minor response or stable disease while those with an AI of ≤10% all had progressive disease (FIG. 5).

Example 11 TSC2 Therapy in Combination with EGFR-Targeted Therapy

To assess cooperative effects of tumor growth data between FUS-1 (FUST) and Erlotinib (Erlo) a Bayesian Bootstrapping analysis approach was used. The $Pr(min(\mu_F, \mu_E)<\mu_C|(data)$ was calculated i.e., the posterior probability that the minimum of the two posterior mean colony formation for FUS-1 alone, $\mu_F$, or Erlotinib alone, $\mu_E$, is less than the mean posterior colony formation for the combination $\mu_C$. This probability calculates the likelihood that average colony formation in the combination arm will be less than the minimum of the two single agent arms. Cooperative effects are shown if this posterior probability is large. Thus, the probability of cooperative effect ranges from 0.0 to 1.0 where 0 means no chance of a true cooperative effect given the data observed while 1 means 100% certainty of a cooperative effect given the data observed. The Statistical software S-PLUS 8.0 were used for all the analyses.

Figure 6:
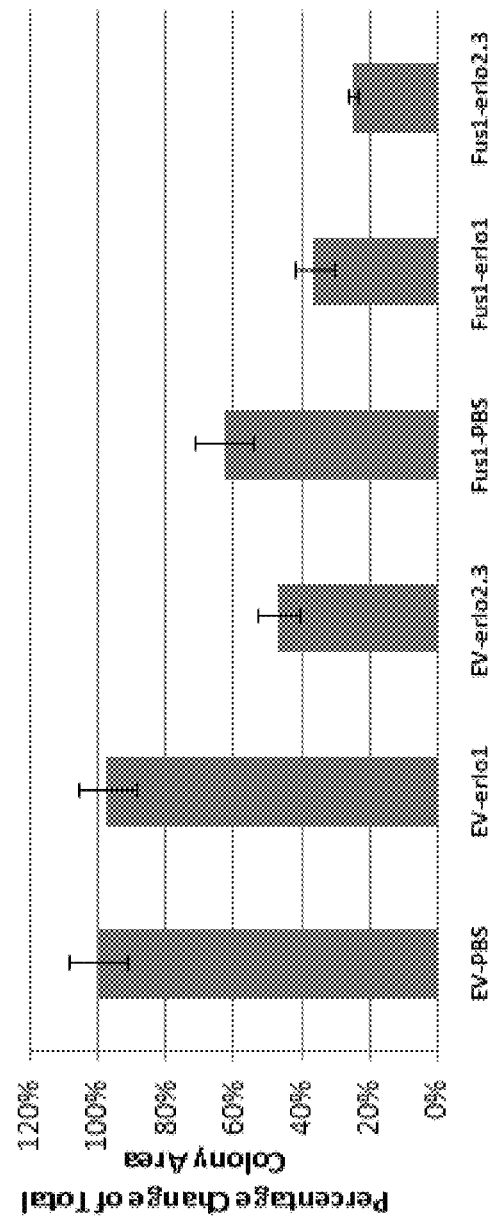
FIG. 6: Fus1 and Erlotinib combined treatment effect on colony formation of H1299 cells. Graph shows the results of colony formation assays as change in total colony area relative to control for each treatment condition. "EV" indicates empty vector; Fus1 indicates a vector containing Fus1; numerical values following "erlo" indicate µg of Erlotinib; PBS indicates Phosphate-Buffer Saline control.

In the studies presented here all cell lines, including H1975 cells, which have two EGFR mutations (L858R/T790M), and doses of erlotinib showed almost near certainty of a cooperative effect (See, FIGS. 6-10 and Tables 5-8). The probability of cooperative effectiveness calculated from the results of each of the studies is provided below:

For 1299 cells: FUS1+Erlotinib (1.0 μg) (Probability of Cooperative Effect=1.00); FUS1+Erlotinib (2.3 μg) (Probability of Cooperative Effect=1.00). See Table 5; FIG. 6.

Figure 7:
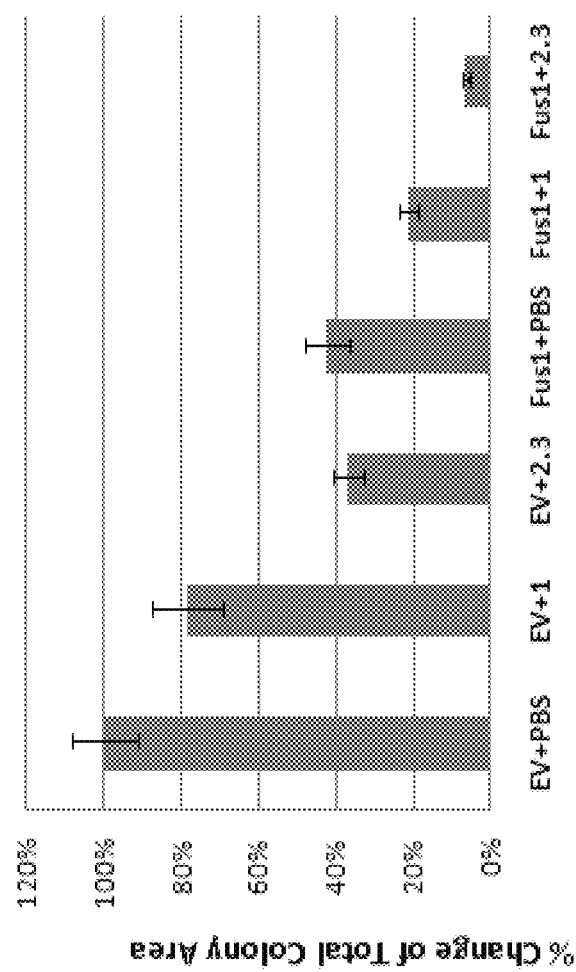
FIG. 7: Fus1 and Erlotinib combined treatment effect on colony formation of H322 cells. Graph shows the results of colony formation assays as change in total colony area relative to control for each treatment condition. "EV" indicates empty vector; Fus1 indicates a vector containing Fus1; numerical values following "+" indicate µg of Erlotinib; PBS indicates Phosphate-Buffer Saline control.

For H322 cells: FUS1+Erlotinib (1.0 μg) (Probability of Cooperative Effect=1.0); FUS1+Erlotinib (2.3 μg) (Probability of Cooperative Effect=1.0). See Table 6; FIG. 7.

Figure 8:
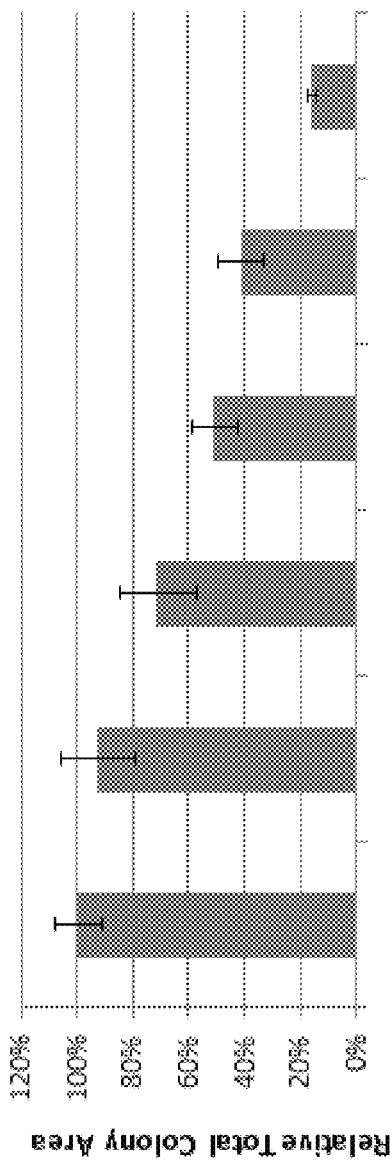
FIG. 8: Fus1 and Erlotinib combined treatment effect on colony formation of A549 cells. Graph shows the results of colony formation assays as change in total colony area relative to control for each treatment condition. "EV" indicates empty vector; Fus1 indicates a vector containing Fus1; numerical values following "+" indicate µg of Erlotinib; PBS indicates Phosphate-Buffer Saline control.

For A549 cells: FUS1+Erlotinib (1.0 μg) (Probability of Cooperative Effect=0.9981); FUS1+Erlotinib (2.3 μg) (Probability of Cooperative Effect=1.00). See Table 7; FIG. 8.

Figure 9:
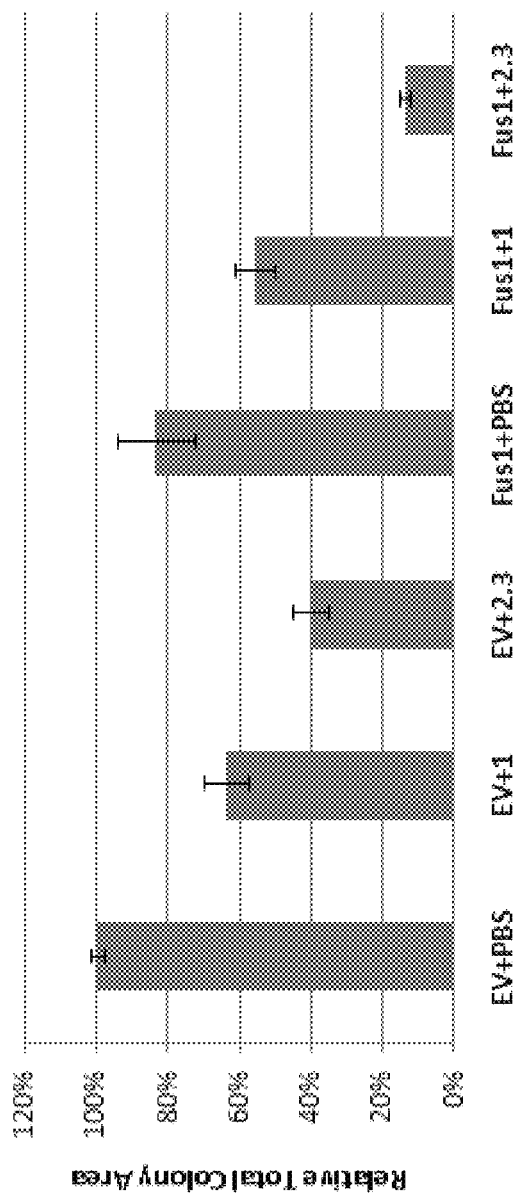
FIG. 9: Fus1 and Erlotinib combined treatment effect on colony formation of H460 cells. Graph shows the results of colony formation assays as change in total colony area relative to control for each treatment condition. "EV" indicates empty vector; Fus1 indicates a vector containing Fus1; numerical values following "+" indicate µg of Erlotinib; PBS indicates Phosphate-Buffer Saline control.
Figure 10:
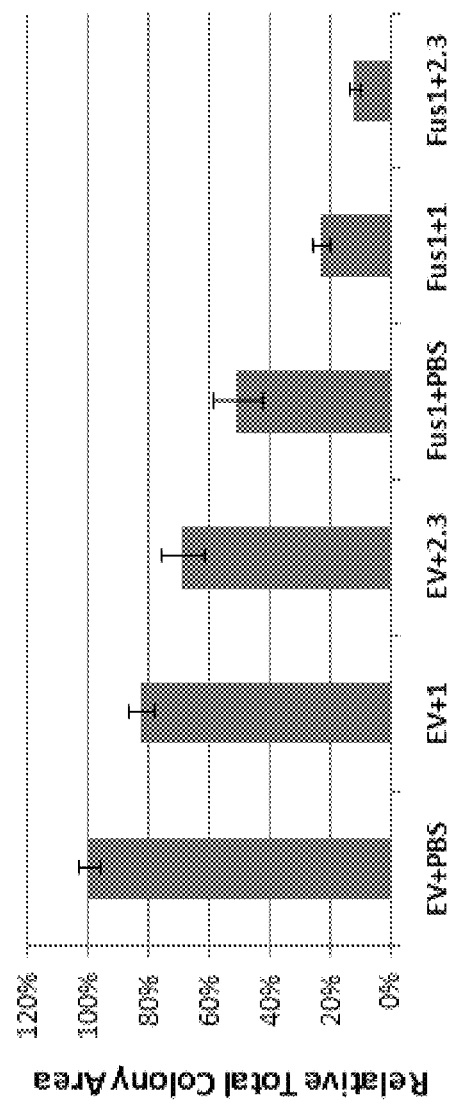
FIG. 10: Fus1 and Erlotinib combined treatment effect on colony formation of H1975 cells (H1975 cells have two EGFR mutations, L858R/T790M). Graph shows the results of colony formation assays as change in total colony area relative to control for each treatment condition. "EV" indicates empty vector; Fus1 indicates a vector containing Fus1; numerical values following "+" indicate µg of Erlotinib; PBS indicates Phosphate-Buffer Saline control.

For H460 cells: FUS1+Erlotinib (1.0 μg) (Probability of Cooperative Effect=0.9874); FUS1+Erlotinib (2.3 μg) (Probability of Cooperative Effect=1.0). See Table 8; FIG. 9.

For H1975 cells: FUS1+Erlotinib (1.0 μg) (Probability of Cooperative Effect=1.0); FUS1+Erlotinib (2.3 μg) (Probability of Cooperative Effect=1). See FIG. 10.

TABLE 5

Fus1 and Erlotinib Combine Treatment Effect on Colony Formation of H1299 Cells.

| Group | pc301PBS | pc301 + 1 | pc301 + 2.3 | EV + PBS | EV + 1 | EV + 2.3 | Fus1 + PBS | Fus1 + 1 | Fus1 + 2.3 |
|---|---|---|---|---|---|---|---|---|---|
| 1 | 40355.0 | 31957.0 | 24425.0 | 15796.0 | 18287.0 | 9216.0 | 12651.0 | 6212.0 | 4315.0 |
| 2 | 39639.0 | 25107.0 | 18192.0 | 18653.0 | 15301.0 | 8082.0 | 10095.0 | 5307.0 | 4633.0 |
| 3 | 47131.0 | 32817.0 | 21246.0 | 17517.0 | 17010.0 | 7128.0 | 9988.0 | 7396.0 | 4070.0 |
| average | 42375 | 29960 | 21288 | 17322 | 16866 | 8142 | 10911 | 6305 | 4339 |
| SD | 4134 | 4225 | 3117 | 1438 | 1498 | 1045 | 1508 | 1048 | 282 |
| CV % | 9.8% | 14.1% | 14.6% | 8.3% | 8.9% | 12.8% | 13.8% | 16.6% | 6.5% |
| P value of Ttest erlo diffent dose | | 0.013 | 0.009 | | 0.406 | 0.010 | | 0.027 | 0.009 |
| | | | 0.014 | | | 0.004 | | | 0.062 |
| EV vs FUS1 or Erlo | | | | | 0.7231 | 0.0009 | 0.0060 | | |
| Fus1 + 1 vs Fus1 or Erlo | | | | | 0.0006 | | 0.0122 | | |
| Fus1 + 2.3 vs Fus1 or Erlo | | | | | | 0.0037 | 0.0018 | | |
| normalized on pc301 | 100% | 71% | 50% | 41% | 40% | 19% | 26% | 15% | 10% |
| normalized on EV | | | | 100% | 97% | 47% | 63% | 36% | 25% |
| normalized % SD | | | | 8.3% | 8.6% | 6.0% | 8.7% | 6.0% | 1.6% |

TABLE 6

Fus1 and Erlotinib Combine Treatment Effect on Colony Formation of H322 Cells

| Group | pc301PBS | pc301 + 1 | pc301 + 2.3 | EV + PBS | EV + 1 | EV + 2.3 | Fus1 + PBS | Fus1 + 1 | Fus1 + 2.3 |
|---|---|---|---|---|---|---|---|---|---|
| 1 | 57216 | 44761 | 28610 | 46711 | 43621 | 20293 | 23947 | 11162 | 3203 |
| 2 | 65399 | 37701 | 28943 | 46887 | 36971 | 16469 | 19851 | 11259 | 3653 |
| 3 | 55676 | 35079 | 27080 | 53930 | 35119 | 17511 | 18660 | 8947 | 2782 |
| average | 59430 | 39180 | 28211 | 49176 | 38570 | 18091 | 20819 | 10456 | 3213 |
| SD | 5226 | 5008 | 994 | 4118 | 4471 | 1977 | 2773 | 1308 | 436 |
| CV % | 8.8% | 12.8% | 3.5% | 8.4% | 11.6% | 10.9% | 13.3% | 12.5% | 13.6% |
| P value of Ttest erlo diffent dose | | 0.022 | 0.003 | | 0.073 | 0.004 | | 0.007 | 0.004 |
| | | | 0.026 | | | 0.003 | | | 0.003 |
| EV vs FUS1 or Erlo | | | | | 0.0391 | 0.0003 | 0.0006 | | |
| Fus1 + 1 vs Fus1 or Erlo | | | | | 0.0005 | | 0.0042 | | |
| Fus1 + 2.3 vs Fus1 or Erlo | | | | | | 0.0002 | 0.0004 | | |
| normalized on pc301 | 100% | 66% | 47% | 83% | 65% | 30% | 35% | 18% | 5% |
| normalized on EV | | | | 100% | 78% | 37% | 42% | 21% | 7% |
| normalized % SD | | | | 8.4% | 9.1% | 4.0% | 5.6% | 2.7% | 0.9% |

TABLE 7

Fus1 and Erlotinib Combine Treatment Effect on Colony Formation of A549 Cells.

| Group | pc301PBS | pc301 + 1 | pc301 + 2.3 | EV + PBS | EV + 1 | EV + 2.3 | Fus1 + PBS | Fus1 + 1 | Fus1 + 2.3 |
|---|---|---|---|---|---|---|---|---|---|
| 1 | 4147 | 3779 | 1625 | 2714 | 3083 | 2484 | 1358 | 932 | 511 |
| 2 | 6208 | 2436 | 1803 | 3147 | 2538 | 1910 | 1732 | 1279 | 435 |
| 3 | 6586 | 3393 | 1651 | 2716 | 2334 | 1738 | 1308 | 1358 | 460 |
| average | 5647 | 3203 | 1693 | 2859 | 2652 | 2044 | 1466 | 1190 | 469 |
| SD | 1313 | 691 | 96 | 249 | 387 | 391 | 232 | 227 | 39 |
| CV % | 23.2% | 21.6% | 5.7% | 8.7% | 14.6% | 19.1% | 15.8% | 19.0% | 8.3% |
| P value of Ttest erlo diffent dose | | 0.073 | 0.016 | | 0.278 | 0.057 | | 0.116 | 0.011 |
| | | | 0.040 | | | 0.000 | | | 0.021 |
| EV vs FUS1 or Erlo | | | | | 0.4791 | 0.0382 | 0.0021 | | |
| Fus1 + 1 vs Fus1 or Erlo | | | | | 0.0049 | | 0.2138 | | |
| Fus1 + 2.3 vs Fus1 or Erlo | | | | | | 0.0023 | 0.0018 | | |
| normalized on pc301 | 100% | 57% | 30% | 51% | 47% | 36% | 26% | 21% | 8% |
| normalized on EV | | | | 100% | 93% | 71% | 51% | 42% | 16% |
| normalized % SD | | | | 8.7% | 13.5% | 13.7% | 8.1% | 7.9% | 1.4% |

TABLE 8

Fus1 and Erlotinib Combine Treatment Effect on Colony Formation of H460 Cells.

| Group | EV + PBS | EV + 1 | EV + 2.3 | Fus1 + PBS | Fus1 + 1 | Fus1 + 2.3 |
|---|---|---|---|---|---|---|
| 1 | 2117 | 1216 | 750 | 1564 | 1158 | 330 |
| 2 | 2179 | 1393 | 968 | 1751 | 1322 | 261 |
| 3 | 2106 | 1470 | 858 | 2018 | 1094 | 289 |
| average | 2134 | 1360 | 859 | 1778 | 1191 | 293 |
| SD | 39 | 130 | 109 | 228 | 118 | 35 |
| CV% | 1.8% | 9.6% | 12.7% | 12.8% | 9.9% | 11.8% |
| P value of T-test on erlo | | 0.005 | 0.001 | | 0.037 | 0.005 |

TABLE 8-continued

Fus1 and Erlotinib Combine Treatment Effect on Colony Formation of H460 Cells.

| Group | EV + PBS | EV + 1 | EV + 2.3 | Fus1 + PBS | Fus1 + 1 | Fus1 + 2.3 |
|---|---|---|---|---|---|---|
| diffent dose | | | 0.006 | | | 0.004 |
| EV vs FUS1 or Erlo | | 0.0006 | 0.00004 | 0.056 | | |
| Fus1 + 1 vs Fus1 or Erlo | | 0.1719 | | 0.0167 | | |
| Fus1 + 2.3 vs Fus1 or Erlo | | | 0.0010 | 0.0004 | | |
| normalized on EV | 100% | 64% | 40% | 83% | 56% | 14% |
| normalized % SD | 1.8% | 6.1% | 5.1% | 10.7% | 5.5% | 1.6% |

The use of FUS1 expression to enhance the effectiveness of gefitinib and overcome gefitinib resistance was also explored in human NSCLC. Re-expression of wild-type FUS1 by FUS1-nanoparticle-mediated gene transfer into FUS1-deficient and gefitinib-resistant NSCLC cell lines H1299, H322, H358, and H460 cells that have a wild-type EGFR significantly (P<0.001) sensitized their response to gefitinib treatment and synergistically induced apoptosis in vitro and in an H322 orthotopic lung cancer mouse model (FIG. 12, Note that these studies included the K-ras mutant cell line H460 which is significant in that patients with K-ras mutant tumors are in general unresponsive to EGFR TKIs). Supra-additive induction of apoptosis was seen with the combination of nanoparticle FUS1 and concentrations of gefitinib similar to steady-state serum concentrations achievable with oral dosing. To understand the mechanism of gefitinib-induced resistance, a gefitinib-resistant HCC827GR NSCLC cell line ($IC_{50}$=16 μM) was established by selecting against gefitinib from the parental HCC827 cells that contain an activating deletion mutation of the EGFR gene and are extremely sensitive to gefitinib treatment ($IC_{50}$=0.016 uM). No secondary mutations in the EGFR gene in the HCC827GR cells was found, but these cells registered a significantly elevated level of phosphorylated AKT protein. Combination treatment with FUS1-nanoparticles and gefitinib at a dose level of $IC_{10}$ significantly re-sensitized the cells to gefitinib, as demonstrated by synergistically enhanced growth inhibition and apoptosis. FUS1 nanoparticle treatment alone or with gefitinib markedly inactivated EGFR and AKT, as shown by decreased phosphorylation levels of both proteins on Western blots, compared with either agent alone (FIG. 12D). Cleavage of caspase-3, caspase-9, and PARP was also significantly induced by the combination of FUS1 and gefitinib in HCC872GR and other gefitinib-resistant NSCLC cells. The combination of FUS1 and erlotinib induced similar levels of tumor cell growth inhibition, apoptosis induction, and inactivation of oncogenic PTKs as those observed in NSCLC cells treated by a combination of FUS1 and gefitinib (FIG. 12A-D).

Figure 13:
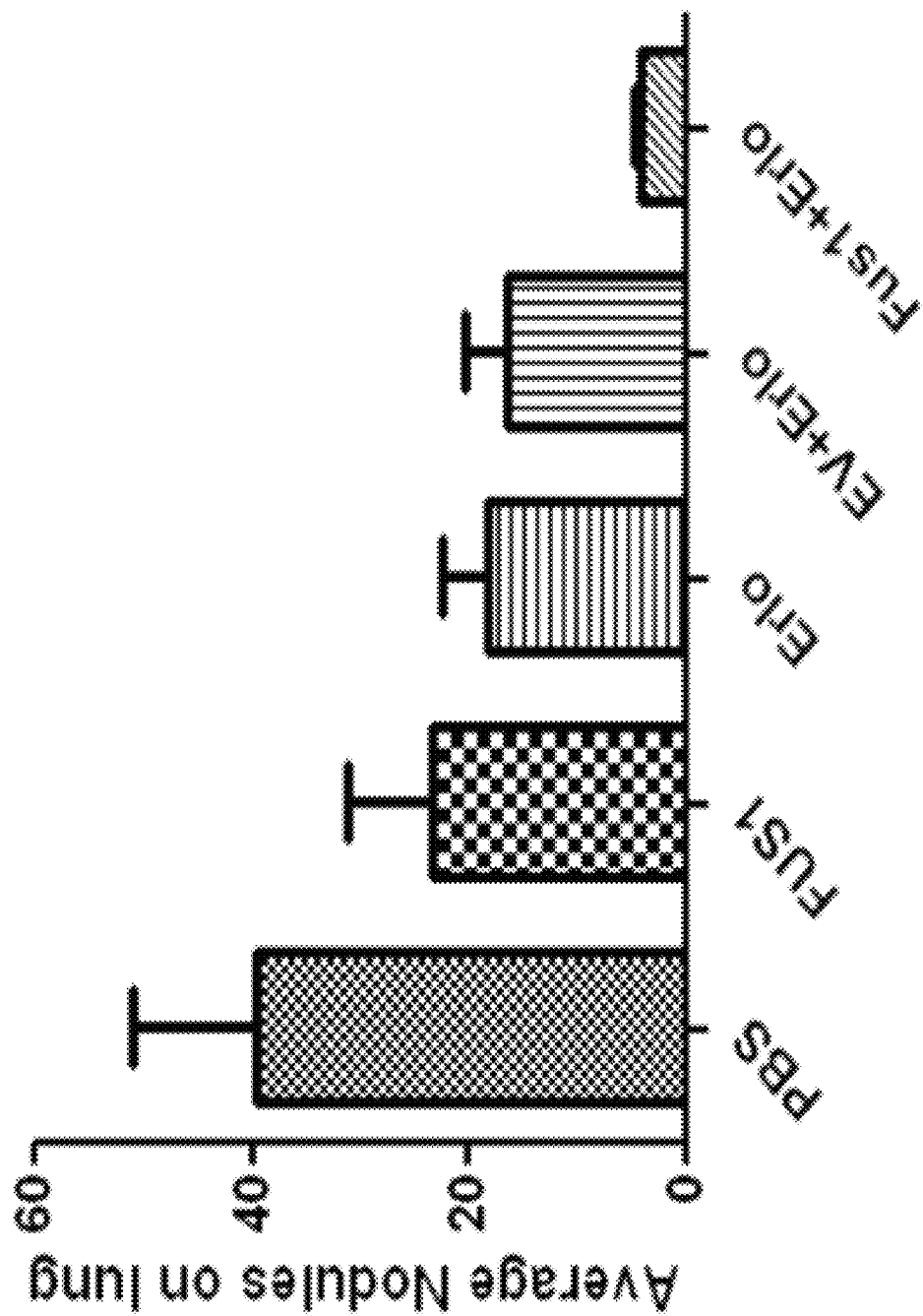
FIG. 13: FUS1 nanoparticle and Erlotinib combination therapy on A549 Lung Colonies. Mice (5-6 wk old nu/nu) were injected in the tail vein with $10^6$ A549 cells. Ten days later treatment was begun with erlotinib 30 mg/kg orally daily for 7 days and FUS1 nanoparticles (25 µg) intravenously on days 10, 13, and 16. Mice were killed on day 36 and lung tumors counted. Erlo=erlotinib; EV=empty vector. The FUS1+erlotinib group is significantly less than all other groups by the two independent sample Wilcoxon rank sum test (p<0.0005).

Example 12 In Vivo Assessment of TSC2 Therapy in Combination with EGFR-Targeted Therapy The cooperative interaction between erlotinib and FUS1 nanoparticles was confirmed in vivo using a lung colony formation metastases model in nu/nu mice with A549 human lung cancer cells injected in the tail vein. Following injection mice were treated with FUS1 nanoparticles and erlotinib and various controls (FIG. 13). The greatest reduction in lung colonies occurred with the FUS1 nanoparticle/erlotinib combination (90% reduction) which was significantly reduced compared to all control groups (p<0.0005).

These studies along with those in Example 11 showed that a combination treatment of FUS1 nanoparticles and gefitinib or erlotinib can promote a synergistic tumor cell killing and overcome drug-induced resistance by simultaneously inactivating the EGFR and the AKT signaling pathways and by inducing apoptosis in resistant cells with wild-type EGFR.

Example 13 Bystander Effect of FUS1-Nanoparticle in NSCLC

Figure 14:
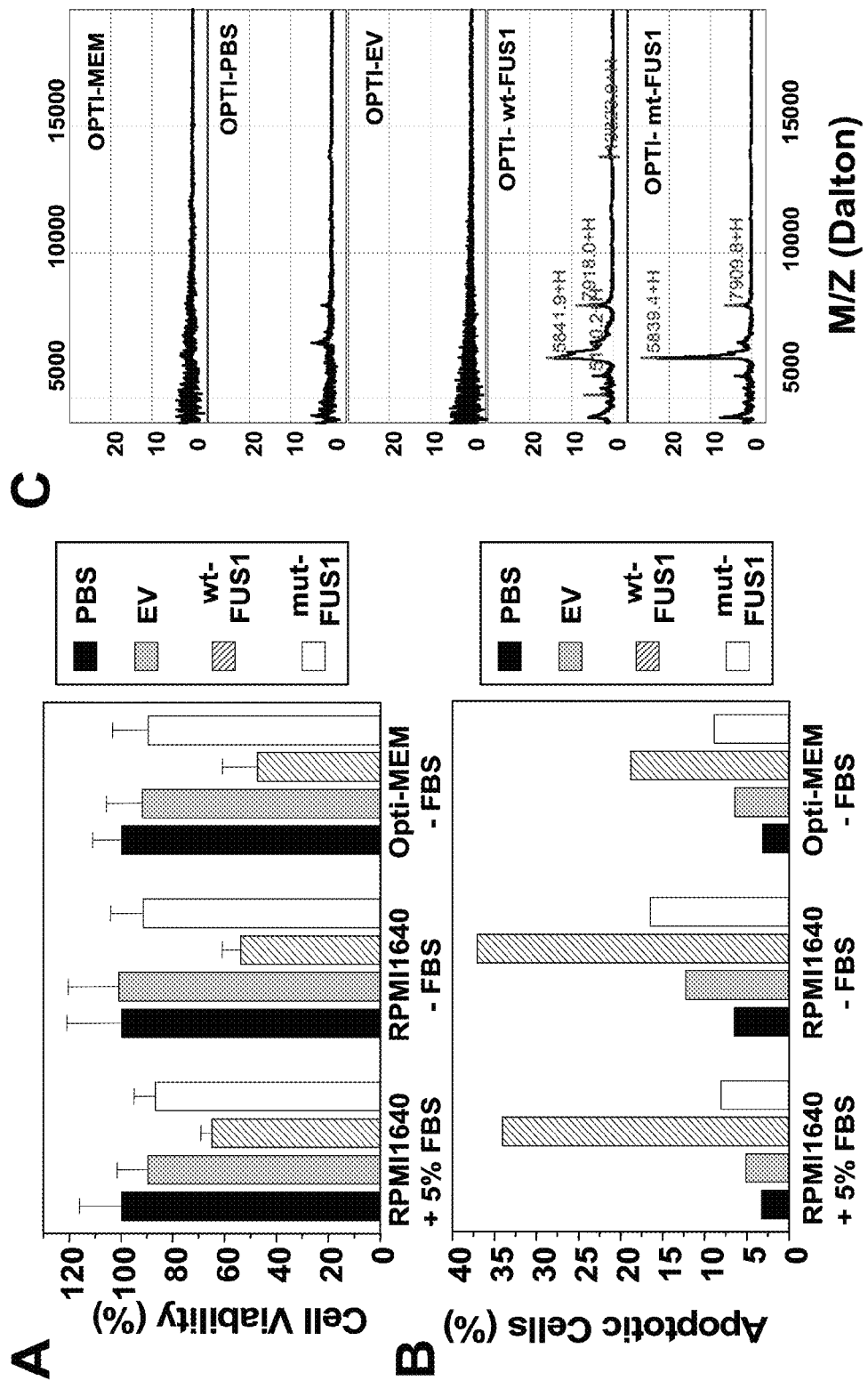
FIG. 14A-C: Effect of Conditioned Medium (CM) from FUS1-nanoparticle Treated H1299 Cells on H1299 Tumor Cell Growth (FIG. 14A) and apoptosis (FIG. 14B).
Figure 15:
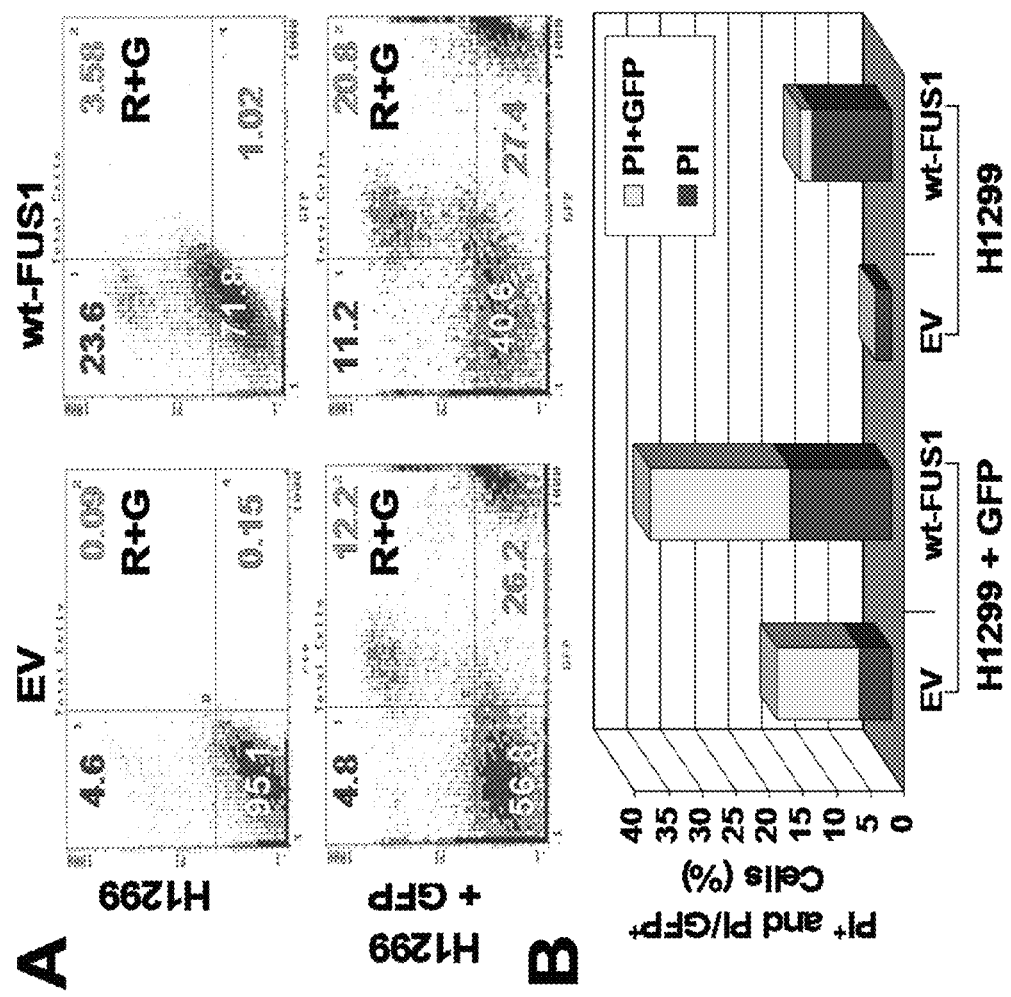
FIG. 15A-B: Bystander effects induced by FUS1-nanoparticle-mediated gene transfer in NSCLC H1299 cells by FACS analysis (FIG. 15A and FIG. 15B). The populations of dead/apoptotic cells are represented by both PI (upper left quadrant)-positive and PI/GFP ("R+G") positive cells. FUS1-transfected H1299 cells were used as effecter cells and Ad-GFP-transduced H1299 cells as target cells and mixed at a ratio of 1:1.

Many currently available gene transfer protocols and techniques are capable of transducing only a fraction of tumor cells in vivo, and thus, relying on a bystander effect (killing of non-transduced cells by products of transduced cells) to achieve clinically-meaningful therapeutic efficacy. For example, bystander effects have been observed in cancer gene therapy by adenoviral or retroviral vector-mediated gene transfer of tumor suppressor genes such as p53 and TRAIL and for suicide gene HSV-TK in cancer cells. These bystander effects are induced through various mechanisms including intercellular communication, interaction of cell surface receptors and ligands, secretion of cytotoxic or apoptotic metabolites and peptides, and activation of anti-cancer cytokine cascades and the immune response. To test whether ectopic expression of FUS1 in tumor cells can cause neighboring cell killing by triggering the release of cytotoxic soluble factors, conditioned medium (CM) was collected from FUS1-transduced H1299 cells. CM was collected after 48 h in cell culture either containing or free of bovine fetal serum (BFS) and concentrated 2-5 fold by lyophilization. The CMs from untransduced (PBS), or empty vector (EV), and myristoylation-deficient mutant FUS1 (mt-FUS1)-transduced cells were used as controls. A marked inhibition of tumor cell growth (FIG. 14A) and induction of apoptosis (FIG. 14B) were detected in H1299 cells treated by concentrated CMs from wt-FUS1-transduced cells compared with those of controls. In addition, distinct soluble protein/peptide species were clearly detected in the serum-free wt-FUS1-CM on protein mass spectra by a ProteinChip array-based SELDI-TOF-MS analysis (FIG. 14C), compared to those of control CMs, suggesting release of specific soluble peptides. To further test the potential bystander effects of FUS1 on lung cancer cells, the wt-FUS1-nanoparticles-transfected H1299 cells were used as effector cells and mixed them with the Ad-GFP-transduced H1299 target cells, which do not express FUS1, at a ratio of 1:1. The empty vector (EV)-nanoparticle-transfected H1299 effectors were used as the control. The mixed cells were then seeded into a 6-well plate and cultured for 48 hr. The dead/apoptotic cells were labeled by PI staining and analyzed by flow cytometry to determine the extent of cell death and apoptosis in both effector and target (GFP) cells. An increased population of dead/apoptotic cells was detected in the GFP-expressing target cells mixed with wt-FUST-transfected H1299 effecter cells, compared with that of target cells mixed with EV-transfected effectors (FIG. 15). This effect is comparable to that seen with a secreted protein such as TRAIL. These preliminary data support the presence of bystander effects induced by FUS1-nanoparticle-mediated gene transfer in lung cancer cells.

Example 14 Preclinical Animal Studies with FUS1-Nanoparticles

Murine Studies

The mouse $LD_{10}$ for a single intravenous dose of DOTAP:Cholesterol-Fus1 liposome complex was determined from a series of experiments. For each experiment, C3H strain mice (4 to 6 weeks old, estimated total blood volume 1 ml) were injected over a period of approximately 3 minutes. The doses ranged from 50 to 150 mcg of DOTAP:Cholesterol-Fus1 liposome complex, and the total injection volume ranged from 100 to 300 microliters. The results of the dose-escalation study in mice are summarized below in Table 9.

TABLE 9

DOTAP: Chol-Fus1 dose escalation in mice

| DOTAP: Chol-Fus1 dose (mcg) | Total number of mice | Injection volumn (ml) | Number of deaths (%) |
| --- | --- | --- | --- |
| 50 | 8 | 100 | 0 |
| 60 | 8 | 120 | 0 |
| 70 | 8 | 140 | 0 |
| 80 | 8 | 160 | 0 |
| 90 | 8 | 180 | 0 |
| 100 | 23 | 200 | 2 (8.6%) |
| 110 | 18 | 220 | 0 |
| 120 | 18 | 240 | 1 (5.6%) |
| 130 | 18 | 260 | 7 (39%) |
| 150 | 23 | 300 | 7 (30%) |

The $LD_{10}$ for a single intravenous injection in mice was conservatively estimated to be 100 micrograms. Of significance, the drug was infused over approximately 3 minutes, and the injection volumes ranged from 100 to 300 microliters, or the equivalent of 10 to 30% of the animals' total blood volume. This rapid rate of infusion would never be used in humans, and the relationship of the rapid infusion rate to the observed animal toxicity remains unclear.

Autopsies were obtained on all animals that died secondary to acute toxicity. Pathological examination of the brain, heart, lungs, spleen, liver, gastrointestinal tract, and kidneys were performed by an attending veterinary pathologist. The pathology findings are summarized below in Table 10.

TABLE 10

Pathology in DOTAP: Chol-Fus1 treated mice

| Dose (mcg) | Number of autopsies | Pathology findings (number of animals) |
| --- | --- | --- |
| 100 | 2 | Lymphoid tissue and spleen, necrosis, apoptosis, and atrophy, moderate (2) |
| | | Multifocal liver degeneration and necrosis, mild (1) |
| | | Acute liver necrosis, mild (1) |
| 120 | 1 | Lymphoid tissue, spleen, and GALT necrosis, apoptosis, and atrophy, moderate (1) |
| | | Acute liver necrosis, moderate (1) |
| | | Malignant lymphoma, kidney (1) |
| | | Glomerulonephritis (1) |

TABLE 10-continued

Pathology in DOTAP: Chol-Fus1 treated mice

| Dose (mcg) | Number of autopsies | Pathology findings (number of animals) |
| --- | --- | --- |
| 130 | 7 | Lymphoid tissue and spleen, necrosis, apoptosis, and atrophy, mild (1), moderate (6) |
| | | Acute liver necrosis, mild (3), moderate (3), severe (1) |
| | | Multifocal myocardial degeneration, necrosis, and mineralization, moderate (2), severe (1) |
| | | Acute tubular necrosis, kidney, minimal (1) |
| | | Lung granuloma/foreign bodies (1) |
| | | Intestinal crypt epithelial acute necrosis, mild (1) |
| 150 | 7 | Lymphoid tissue and spleen, necrosis, apoptosis, and atrophy, mild (3), moderate (4) |
| | | Acute liver necrosis, mild (4), moderate (1), severe (2) |
| | | Multifocal myocardial degeneration, necrosis, and mineralization, mild (1), moderate (2) |
| | | Acute tubular necrosis, kidney, mild (1) |
| | | Multiple subacute to chronic kidney infarcts (1) |
| | | Spleen red pulp myeloid hyperplasia (1) |
| | | Spleen sinus histiocyte marked hyperplasia (1) |
| | | Intestinal crypt epithelial acute necrosis, mild (1) |

Note:
Multifocal myocardial degeneration, necrosis, and mineralization are most likely incidental findings observed in control C3H mice (ref. Vargas, K J, Stephens, L C, Clifford, C B, et al. Dystrophic Cardiac Calcinosis in C3H/HeN Mice. Lab Anim Sci, 46: 572-575, 1996.)
Minimal = 1+, 5-10%; Mild = 2+, 10-20%; Moderate = 3+, 20-50%: Severe = 4+, >50%.

GLP Toxicology Studies

The objective of this study was to determine single dose toxicology of DOTAP:Chol/fus1 in preparation for Phase I studies. The non-toxic dose and dose-limiting toxicity for C3H/HeNCR mice were determined. The study contained three control groups: D5W (vehicle), 4 mM DOTAP:Chol (highest dose of lipid), and 70 µg DNA (highest dose of fus1 plasmid). The study also contained three experimental groups: 70 µg DNA, DOTAP:Chol, 40 µg DNA, DOTAP:Chol and 10 µg DNA, DOTAP:Chol. Each group contained 15 mice (8 female and 7 male). Acute (0-72 hours), subacute (14 days) and chronic (6 weeks) toxicity were evaluated. At 3 and 14 days and at 6 weeks, five mice per group were euthanized. For each mouse, an attempt was made to collect urine for analysis for CBC and serum chemistries. Necropsies were performed and histopathological analysis done on all mice, including those that died during the study. This study was conducted in an AAALAC accredited facility (2000).

All mice in the three control groups (D5W, 4 mM DOTAP:Chol, and 70 micrograms DNA alone) and in the experimental group receiving 10 micrograms DNA, DOTAP:Chol were observed to be normal at all observation time points.

Mice in the experimental group receiving 40 micrograms DNA, DOTAP:Chol appeared normal at the end of the 4 hours post-injection observation period. When observed later that day at approximately 7 hours post injection 14/15 mice were squinting and appeared to be lethargic. One female mouse was very weak, trembling and sat hunched with her eyes closed. She was euthanized and sent to necropsy at that time. On day one post injection (PI), all mice had decreased activity levels and the eyes appeared to be swollen. On day two PI, all mice appeared to have returned to normal activity levels and general appearance. One female mouse had an area of necrosis involving approximately 20% of one pinna at this time point, but otherwise appeared normal. The damaged pinna was interpreted to be the result of trauma. All mice were thereafter normal at all observation time points. In summary, one female mouse became moribund on day zero and was euthanized.

Mice in the experimental group receiving 70 micrograms DNA, DOTAP:Chol appeared normal at the end of the 4 hours post-injection observation period. When observed later that day at approximately 7 hours post injection, all mice were squinting and appeared to be lethargic. On day one PI, one female mouse died. Three male mice and one female mouse were found to be moribund and were euthanized and necropsied. One female mouse was reported to have a swollen face. This mouse and the remaining mice in the group all appeared to have decreased activity levels and abnormal appearance at day one PI. On day two PI, the female mouse that had the swollen face on day one PI was found to be moribund and was euthanized and necropsied. Another female mouse was found dead on day two PI. The remaining mice had decreased or slightly decreased activity levels and some were squinting. On day three PI, 2/8 remaining mice appeared normal, while 6/8 still had decreased activity levels and abnormal general appearance. From day four PI and thereafter, all mice appeared normal at all observation time points. In summary, two female mice died. Three male and two female mice were found moribund and were euthanized.

Non-Human Primate Toxicology

Ten (10) cynomolgus monkeys (*Macaca fascicularis*) were used in the study. Six experimental animals (three male and three female) were injected with DOTAP:Chol/Fus 1 complex on Day 1 and Day 21 of the study. Four control animals (two male and two female) were injected with DOTAP:Cholesterol alone on Day 1 and Day 21 of the study. At days 46-52 the animals were necropsied, blood was collected for hematology and chemistries, and organs were collected for histopathological analysis.

Significant gross and microscopic lesions were found in 1/10 monkeys on protocol. This animal received 1 dose of 0.6 mg/kg DNA, DOTAP:Chol (high dose) and died within 18-20 hours. Lesions in this monkey were most likely treatment related. A second monkey that received the high dose of DNA, DOTAP:Chol had changes in a lymph node. The significance of these minimal changes is not known. Equivocal lesions were found in the femoral bone marrow of two low dose (0.2 mg/kg DNA, DOTAP:Chol) monkeys. The latter may be incidental findings, but were not seen in other protocol animals. No significant gross or microscopic lesions were found in the remaining six animals that received either DOTAP:Chol only or 0.2 mg/kg DNA, DOTAP:Chol.

Example 15 Enhancement of Anti-Tumor Activity of MK2206 in Human Lung Cancer Cells by Tumor Suppressor Gene FUS1

Studies were undertaken to investigate whether FUS1 nanoparticles can sensitize lung cancer cells to chemotherapeutic agents such as MK2206. First preliminary studies were performed to determine the DC transfection efficiency in various lung cancer cell lines. Results of these studies are shown below in Tables 11 and 12.

TABLE 11

Cell lines with high DC transfection efficiency

| Cell line | GFP(%) |
| --- | --- |
| H2882 | 53.9 |
| H1395 | 52.9 |
| H2450 | 51.4 |

TABLE 11-continued

Cell lines with high DC transfection efficiency

| Cell line | GFP(%) |
| --- | --- |
| H358 | 46.1 |
| H1299 | 40.2 |
| H1171 | 37.8 |
| H2887 | 34.6 |
| H661 | 33.1 |
| H522 | 30.8 |
| Calu-1 | 25 |
| H1650 | 24.8 |
| H322 | 24.7 |
| HCC827 | 23.6 |
| HCC366 | 22.4 |

TABLE 12

Cell lines with low DC transfection efficiency

| Cell line | GFP(%) |
| --- | --- |
| H196 | 17 |
| H460 | 11.46 |
| H1944 | 11.4 |
| H1703 | 11.3 |
| H1355 | 9.03 |
| H1648 | 8.9 |
| Calu-6 | 8.6 |
| H1993 | 8.4 |
| H1975 | 7.97 |
| Calu-3 | 7.74 |
| HCC193 | 7.53 |
| H2052 | 6.01 |
| H515 | 6 |
| H2009 | 3.51 |
| H838 | 2.88 |
| H2935 | 1.83 |
| H1792 | 1.67 |
| H157 | 1 |
| H3122 | 0.88 |
| H226 | 0.56 |
| H1437 | 0.44 |
| H125 | 0.36 |

Figure 16:
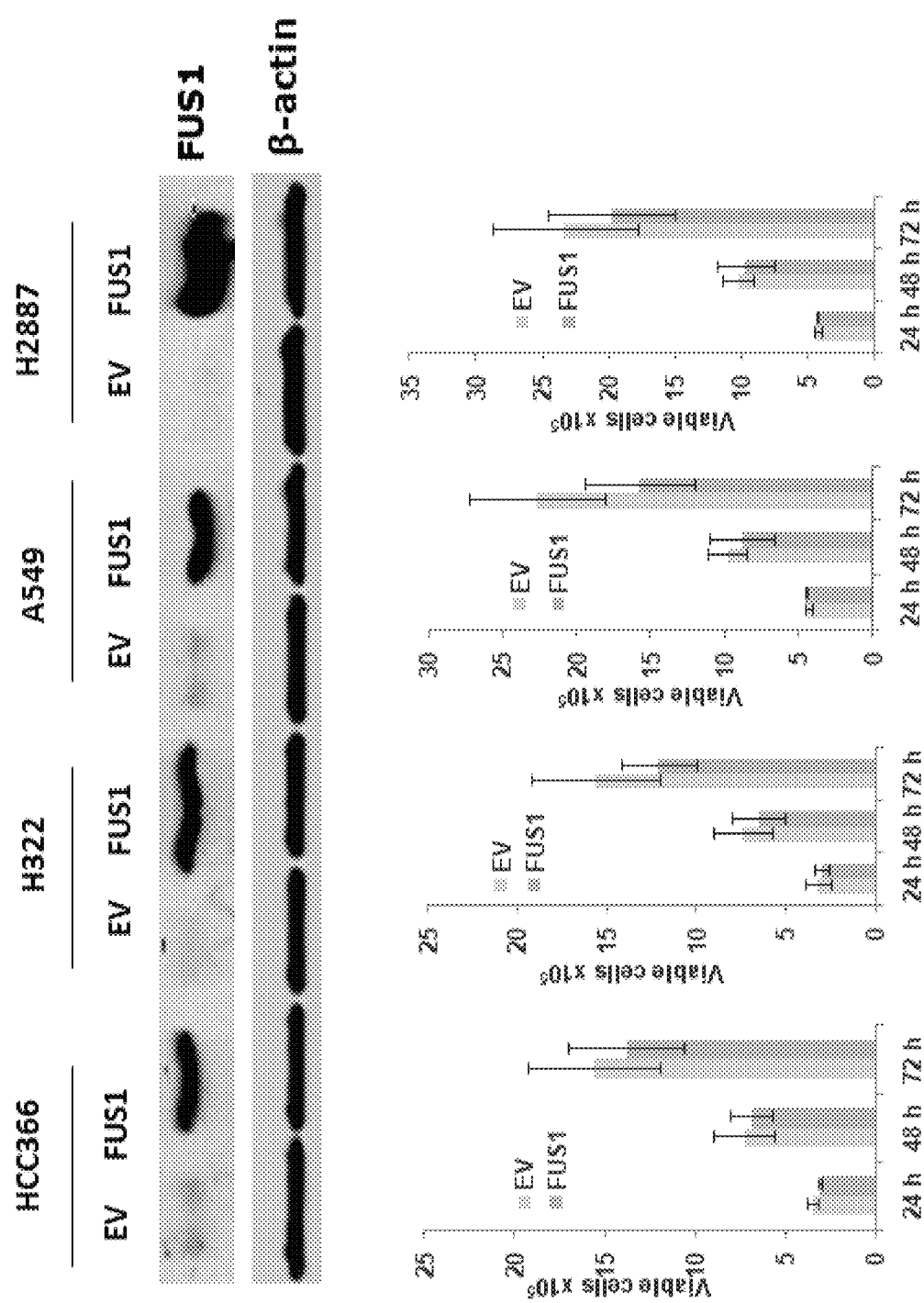
FIG. 16: Effect of FUS1 nanoparticles alone on lung cancer cell lines. Top panel is a representation of Western blot to detect FUS1 expression in cancer cell lines HCC366, H322, A549 or H2887. β-actin a was used as a loading control. Bottom panel are graphs that show the total number of viable cells for each of the four cell lines calculated at 24, 48 and 72 hours upon treatment with FUS1 nanoparticles or empty vector (EV).

Next the effect of FUS1 nanoparticle treatment alone was assessed in an array of lung cancer cell lines. As shown in FIG. 16, FUS1 was effectively expressed in the HCC366, H322, A549 and H2887 cell lines. FUS1 expression resulted in a consistent (but not significant) decrease in cell viability in all cell lines (bottom panel).

Figure 17:
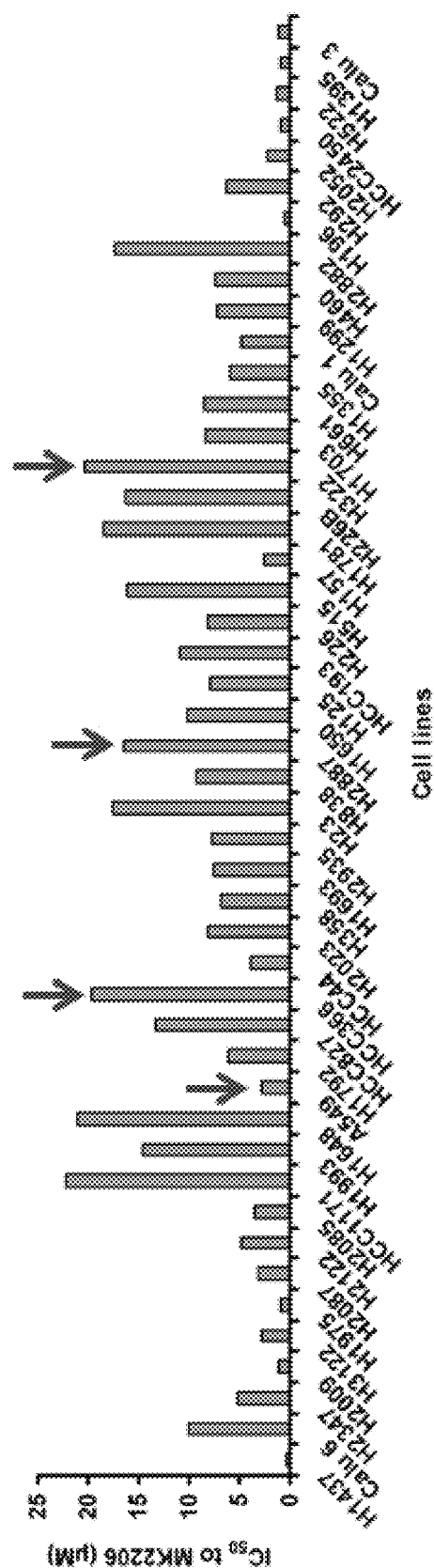
FIG. 17: Single drug treatment of MK2206 on lung cancer cells. Graph shows the inhibitory concentration 50 ($IC_{50}$) for AKT inhibitor MK2206 on various cancer cells. Cell lines that were further analyzed are indicated by arrows.

Single drug treatment with AKT inhibitor MK2206 was also assessed in a wide range of lung cancer cell lines. The effective $IC_{50}$ on the various cells are shown in FIG. 17. Cell lines indicated by arrows (H322, A549, H2887 and HCC386) were subjected to further analysis. First, each of the cell lines was treated with FUS1 nanoparticles or empty vector at increasing concentrations of MK2206. Results shown in FIG. 18 show synergistic cell killing mediated by the combination of FUS1 and the kinase inhibitor. The effect of the combined therapy was especially evident in H2887, H322 and HCC366 cells. Next, the ability of combined FUS1/MK2206 treatment to inhibit colony formation was studied in the cell lines. Graphs shown in FIG. 19 demonstrate that the combination of MK2206 and FUS1 was significantly more effective than either treatment alone at inhibiting colony formation. Thus, FUS1 treatment is able to sensitize cancer cells to the effects of kinase inhibitors such as the AKT inhibitor MK2206. This effect was quantified relative to each studied cell line below in Table 13.

Additional colony formation assays in both H322 and H1299 cells demonstrated that TUSC2 nanoparticles synergistically inhibited colony formation in the cancer cells when combined with the EGFR-targeted therapeutic afatinib (FIG. 26A-B). In these studies, afatinib showed even greater effect in combination with TUSC2 than similar concentrations of erlotinib combined with TUSC2. Still further studies indicated that dasatinib has enhanced anti-cancer activity when used in conjunction with TUSC2 nanoparticles.

TABLE 13

Fold decrease in $IC_{50}$ of MK2206 when combined with FUS1-nanoparticles and gene mutation status

| Cell line | $IC_{50}$ (MK2206 alone) | $IC_{50}$ (MK2206 + FUS1) | Fold reduction | kras | Braf | EGFC | PIK3CA | LKB1 |
|---|---|---|---|---|---|---|---|---|
| H322 | 20.39 | 1.24 | 16.4 | wt | wt | wt | wt | mutant |
| HCC366 | 18.4 | 2.17 | 8.5 | — | — | — | — | mutant |
| H2887 | 16.53 | 1.28 | 12.9 | — | — | — | — | — |
| A549 | 2.86 | 0.56 | 5.1 | mutant | wt | wt | wt | mutant |

Further studies were undertaken to evaluate the ability of FUS1 and MK2206 treatment to induce apoptosis. Cells were treated with the two agents, or each individually, stained by propidium iodide (PI) and analyzed by flow cytometry. Results of these studies are shown in the histograms of FIG. 20. In the case of each cell line, combined FUS1 and MK2206 treatment resulted in significantly more apoptotic cells as compared to either agent alone (indicated by the horizontal bar in the histograms).

Figure 21:
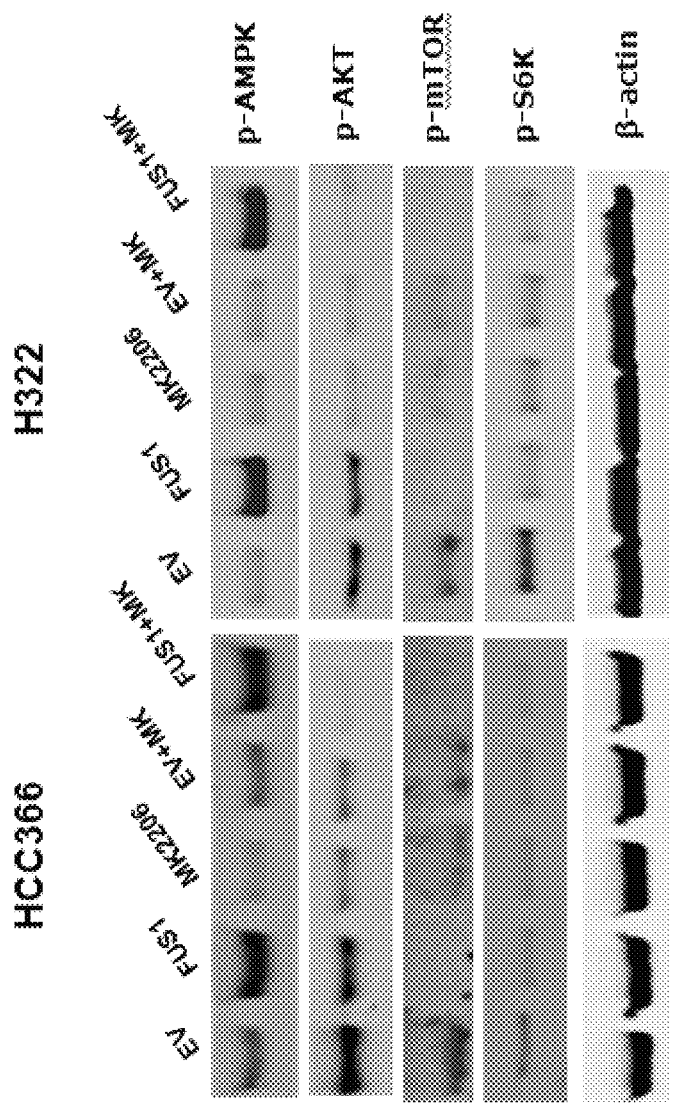
FIG. 21: Immunoblot of p-AKT, p-AMPK and p-mTOR in FUS1/MK2206-treated cell lines. Phosphorylation specific antibodies were used to assess expression of phosphorylated AMPK, AKT, mTOR and S6K in HCC366 or H322 cells. Cells were treated with empty vector (EV); FUS1 nanoparticles (FUS1); MK2206; empty vector+MK2206 (EV+MK); or FUS1 nanoparticles+MK2206 (FUS1+MK) prior to assessment for phosphorylated protein expression. Immunoblot of β-actin was used as a loading control.
Figure 22:
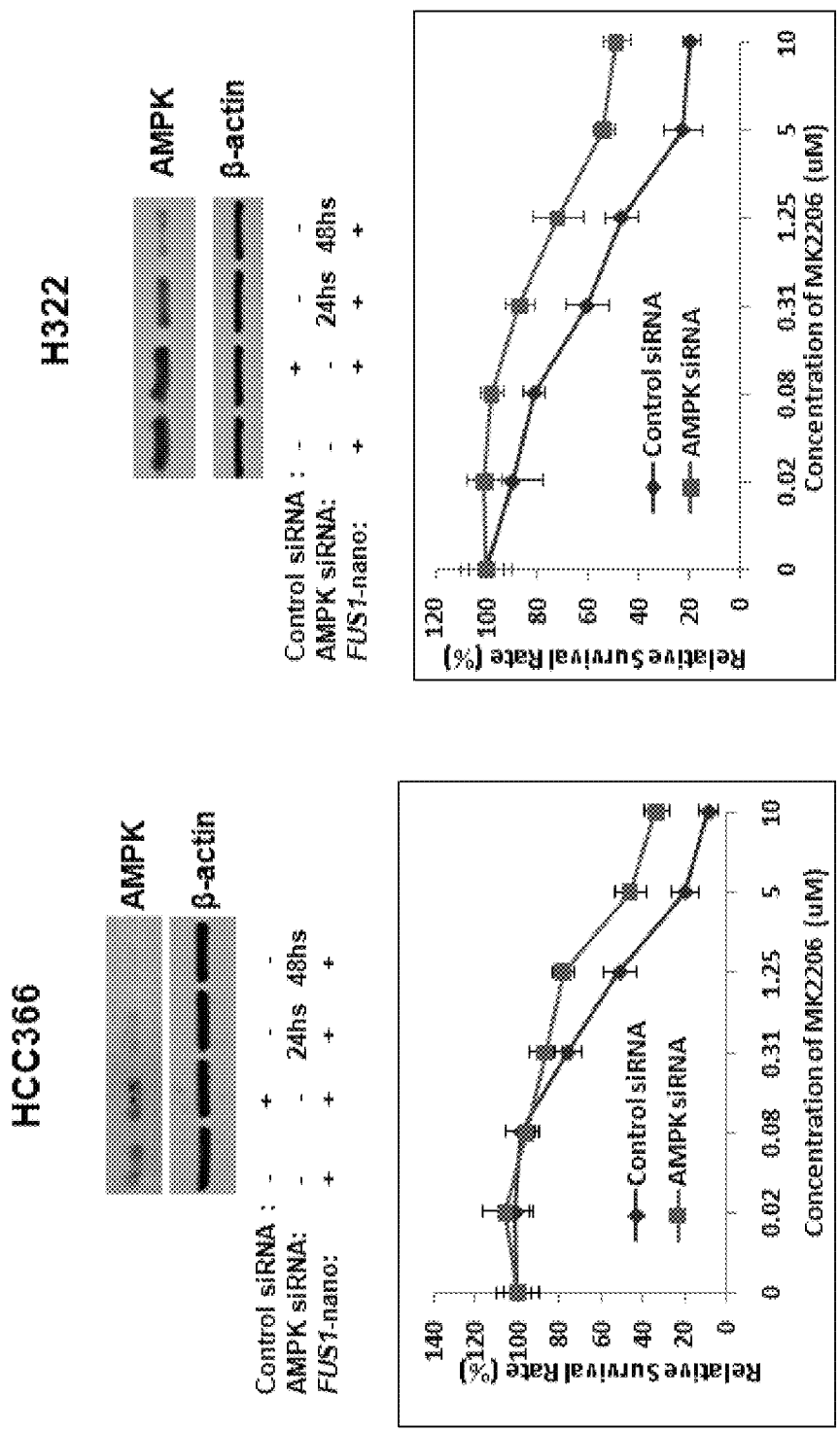
FIG. 22: The effect of AMP-activated protein kinase (AMPK)-specific siRNA on FUS1/MK2206-induced cell death. Cell survival was assessed in HCC366 and H322 cells treated with FUS1 nanoparticles and various concentrations of MK2206 in the presence or absence of siRNA targeted to AMPK. Top panels are representations of Western blots confirming effective knock-down of AMPK expression upon introduction of siRNA. Bottom panels are graphs showing relative cell survival (y-axis) at various concentrations of MK2206 (x-axis) with and without AMPK siRNA as indicated.
Figure 25:
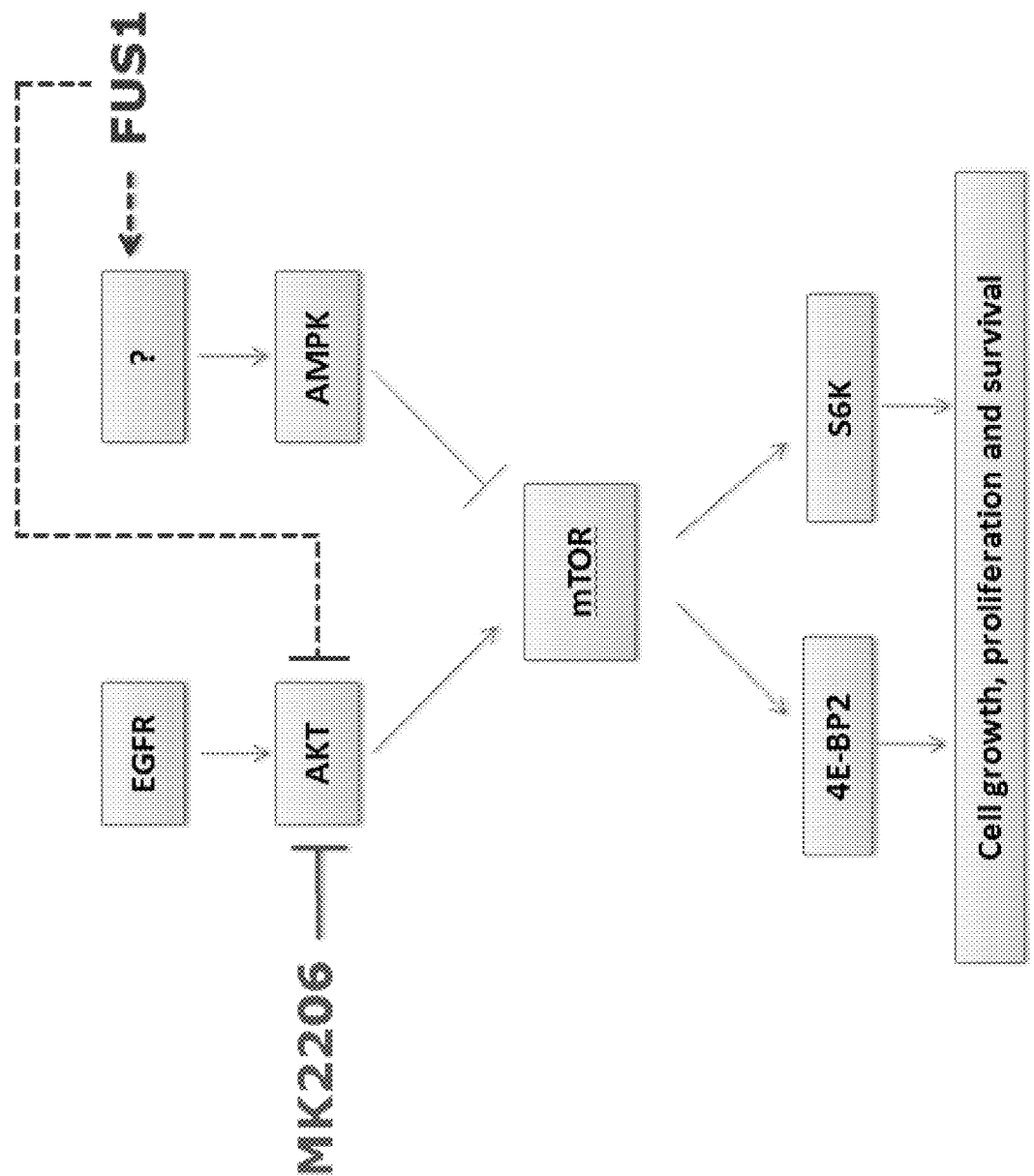
FIG. 25: Proposed mechanism of FUS1/MK2206-induced cell death through AKT/AMPK/mTOR pathway. Schematic shows example members of a signaling pathway modulated by FUS1 and MK2206 treatment.

To better determine the mechanism for synergistic FUS1/MK2206 effect, treated cells were subjected to an immunoblots to assess the phosphorylation status of cell signaling molecules. As shown in FIG. 21, FUS1 alone resulted in an increased in phosphorylated AMPK (p-AMPK), but had little effect on the level of phosphorylated AKT (p-AKT). On the other hand, the addition of MK2206 significantly reduced phosphorylated AKT levels, while a robust increase in phosphorylated AMPK (mediated by FUS1) was maintained. Indeed, the role of AMPK signaling in FUS1-mediated cell killing was confirmed by the fact that treatment of cells with a AMPK-targeted siRNA partially protected the cells from the effects of FUS1/MK2206 treatment (see, e.g., FIG. 22). Likewise, an inhibitor of AMPK activity (Compound C) was also able to partially protect cancer cells from FUS1/MK2206-mediated killing (FIG. 23). Thus, FUS1-increased sensitivity to MK2206 is associated with the down-regulation of AKT and mTOR phosphorylation and up-regulation of AMPK phosphorylation. In view of these studies a proposed FUS/MK2206 signaling pathway is provided as FIG. 25.

The in vivo effectiveness of combination FUS1 and MK2206 treatment was further assessed using a mouse xenograft model. For these studies H322 cells were transplanted into mice and the explanted cells allowed to grow in vivo. Tumor mass was assessed at various time points in the presence of FUS1 therapy, MK2206 therapy or the combination of the two. In all cases expression of FUS1 and activity of MK2206 (as evidenced by reduced p-AKT expression) was histologically evaluated in samples from the mice. As shown in FIG. 24, results of these studies showed that combined FUS1 and MK2206 therapy was far more effective than either treatment alone at inhibiting tumor growth in the animals.

REFERENCES

The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,533,254
U.S. Pat. No. 4,554,101
U.S. Pat. No. 4,728,575
U.S. Pat. No. 4,728,578
U.S. Pat. No. 4,737,323
U.S. Pat. No. 4,921,706
U.S. Pat. No. 5,030,453
U.S. Pat. No. 5,397,987
U.S. Pat. No. 5,855,911
U.S. Pat. No. 5,962,016
U.S. Pat. No. 6,413,544
U.S. Pat. No. 6,610,657
U.S. Pat. No. 6,680,068
U.S. Pat. No. 6,770,291
U.S. Pat. No. 6,770,291
U.S. Pat. No. 7,902,441
U.S. Publn. 2004/0208921
U.S. Publn. 2006/0251726
U.S. Publn. 2007/0092968
U.S. Publn. 2009/0023207
U.S. Publn. 2011/0052570
Aksentijevich et al., *Human Gene Therapy*, 7:1111-22, 1996.
Arap et al., *Cancer Res.*, 55(6):1351-1354, 1995.
Ausubel et al., *Current Protocols in Molecular Biology*, John Wiley & Sons, Inc., New York, N.Y., 1996; 1998
Bakhshi et al., *Cell*, 41(3):899-906, 1985.
Ballou et al., *Bioconjugate Chemistry*, 15:79-86, 2004.
Ben-Neriah et al., *Science*, 233:212-214, 1986.
Bishop, *Cell*, 64:235-48, 1991.
Blankenberg, *Cancer Biology & Therapy*, 7(10):1525-1532, 2008.
Brady and Dodson, *Nature*, 368:692-693, 1994.
Buchhagen et al., *Head and Neck*, 18:529-537, 1996.
Butturini et al., *Leukemia Res.*, 20(6):523-529, 1996.
Caldas et al., *Nat. Genet.*, 8(1):27-32, 1994.
Chapman et al., *Nucleic acid Res*, 19: 3979-3986, 1991.
Cheng et al., *Cancer Res.*, 54(21):5547-5551, 1994.
Cheng et al., *Invest. Radiol.*, 22(1):47-55, 1987.
Clayman et al., *Journal of Clinical Oncology*, 16:2221-32, 1998.
Cleary and Sklar, *Proc. Natl. Acad. Sci. USA*, 82(21):7439-43, 1985.
Cleary et al., *J. Exp. Med.*, 164(1):315-320, 1986.
Colledge and Scott, *Trends in Cell Biology*, 9:216-221, 1999.
Daly et al., *Oncogene*, 8:1721-1729, 1993.
Deng et al., *Cancer Res.*, 67:709-17, 2007.
Drin et al., *AAPS Pharm. Sci.*, 4(4):1-7, 2002.
Du et al., *J. Pept. Res.*, 51:235-243, 1998.
Dubertret et al., *Science*, 298:1759-1762, 2002.
Dwarakanath et al., *Biochem. Biophysical Res. Commun.*, 325:739-743, 2004.
Eggermont et al., *EMBO J.*, 12: 2539-2548, 1993.

Ellerby et al. *Nature Med.*, 9:1032-1038, 1999.
Farhood et al., *Biochim. Biophys. Act*, 289-295, 1995.
Ferrari, *Nature Reviews*, 5:161-171, 2005.
Fidler and Ellis, *Cell*, 79(2):185-188, 1994.
Folkman and Shing, *J. Biol. Chem.*, 267(16):10931-10934, 1992.
Folkman, *Nature Med.*, 1:27-31, 1995.
Frangioni, *Current Opin. Chem. Biol.*, 7:626-634, 2003.
Gazdar et al. In: *Sym. Quant. Biol.*, Cold Spring Harbor, 59:565-572, 1994.
Gazdar et al., *Intl. J. Cancer*, 78:766-774, 1998.
Ghosh and Bachhawat, In: *Liver Diseases, Targeted Diagnosis and Therapy Using Specific Receptors and Ligands*, Wu et al. (Eds.), Marcel Dekker, N.Y., 87-104, 1991.
Goodwin et al., *J. Biol. Chem.*, 267: 16330-16334, 1992.
Gorunova et al., *Genes Chrom. Cancer*, 23:81-99, 1998.
Great Britain Appln. 2193095 A
Gupta et al., *Biomaterials*, 26:3995-4021, 2005.
Gupta et al., *Biomaterials*, 26:3995-4021, 2005.
Gupta et al., *Biomaterials*, 26:3995-4021, 2005.
Gupta, *IEEE Trans. Nanobioscience.*, 3:66-73, 2004.
Hanahan and Folkman, *Cell*, 86(3):353-364, 1996.
Hantschel et al., *Cell*, 112:845-857, 2003.
Hollstein et al., *Science*, 253(5015):49-53, 1991.
Hope et al., 1985
Horowitz, In: *MRI Physics for Radiologists: A Visual Approach*, 1995
Hughson et al., *Cancer Genet. Cytogenet.*, 106:93-104, 1998.
Hussussian et al., *Nat. Genet.*, 8(1):15-21, 1994.
Hvalby et al., *Proc. Natl. Acad. Sci. USA*, 91:4761-4765, 1994.
Ito et al., *Mol. Ther.*, 7:409-18, 2003.
Ito et al., *Cancer Gene Ther.*, 11:733-9, 2004.
Jameson et al., *Nature* 368: 744-746, 1994
Ji et al., *Cancer Res.*, 62:2715-2720, 2000.
Ji et al., *Cancer Res.*, 62:2715-20, 2002.
Ji et al., *Future Oncology*, 1:79-92, 2005.
Ji et al., *Journal of Thoracic Oncology.*, 327-30 10.1097/JTO.0b013e31816bce65, 2008.
Johnson et al., *J. Virol.*, 67:438-445, 1993.
Kamb et al., *Nat. Genet.*, 8(1):23-26, 1994.
Kamb et al., *Science*, 2674:436-440, 1994.
Kerr et al., *Br. J. Cancer*, 26(4):239-257, 1972.
Kerr et al., *Br. J. Cancer*, 26(4):239-257, 1972.
Kersemaekers et al., *Intl. J. Cancer*, 79:411-417, 1998.
Kloetzer et al., *Virology*, 140(2):230-238, 1985.
Kohno et al., *Cancer*, 85:341-347, 1999.
Kondo et al., *Oncogene*, 20:6258-6262, 2001.
Kondo et al., *Oncogene*, 20:6258-6262, 2001.
Kyte and Doolittle, *J. Mol. Biol.*, 157(1):105-132, 1982.
Lerman et al., *Cancer Res.*, 60:6116-33, 2000.
Lewin et al., *Nat. Biotechnol.*, 18:410-414, 2000.
Lin et al., *Oncogene*, 20:1873-1881, 2001.
Ling et al., *Cancer Res.*, 63:298-303, 2003.
Liposome Technology, Gregoriadis (Ed.), Boca Raton, Fla., CRC Press, 1984.
Lowe et al., *Nature*, 2004; 432:307-15, 2004.
Mabry et al., In: *Lung Cancer in the Genetic Basis of Human Cancer*, Vogelstein and Kinzler (Eds.), McGraw Hill, 671-679, 1998.
Mayer et al., *Biochim. Biophys. Acta*, 858(1):161-168, 1986.
Mayhew et al., *Biochim. Biophys. Acta*, 775(2):169-174, 1984.
Mayhew et al., *Methods Enzymol.*, 149:64-77, 1987.
Michalet et al., *Science*, 307:538-544, 2005.
Miller et al., *Cancer*, 47:207-214, 1981.
Miller et al., *Oncogene*, 22:6006-6013, 2003.
Minna et al., In: *Cancer: Principles and Practice of Oncology*, 5th Ed., Philadelphia: Lippincott, 849-857, 1997.
Morawski et al., *Current Opinion Biotech.*, 16, 89-92, 2005.
Mori et al., *Cancer Res.*, 54(13):3396-3397, 1994.
Nishihara et al., *Cancer Letter*, 180(1):55-61, 2002.
Nobri et al., *Nature (London)*, 368:753-756, 1995.
Obenauer et al., *Nucleic Acids Res.*, 31(13):3635-3641, 2003.
Okamoto et al., *Proc. Natl. Acad. Sci. USA*, 91(23):11045-11049, 1994.
Orlow et al., *Cancer Res*, 54(11):2848-2851, 1994.
Orlow et al., *Int. J. Oncol.*, 15(1):17-24, 1994.
O'Quigley J et al., *Biometrics*, 46:33-48, 1990.
PCT Appln. PCT/US85/01161
PCT Appln. PCT/US89/05040
PCT Appln. WO 02/100435A1
PCT Appln. WO 03/015757A1
PCT Appln. WO 04/002453A1
PCT Appln. WO 04029213A2
Pure & Appl. Chem., 63(3):427-463, 1991.
Ramesh et al., *Mol. Ther.*, 3:337-50, 2001.
Remington's Pharmaceutical Sciences" 15th Edition, pages 1035-1038 and 1570-1580, 1990.
Roberts et al., *Adv. Drug Del. Rev.*, 54(4):459-476, 2002.
Rojas et al., *J. Biol. Chem.*, 271:27456-27461, 1996.
Rojas et al., *Nature Biotechnol.*, 16:370-375, 1998.
Roth et al., *Nat. Med.*, 2:985-91, 1996.
Roth, *Forum*, 8:368-376, 1998.
Roth, *Expert Opinion on Biological Therapy*, 6:55-61, 2006.
Sambrook et al., In: *Molecular Cloning: A Laboratory Manual*, 2nd Ed., Cold Spring Harbor Press, Cold Spring Harbor, N.Y., 1989
Schwarze et al., *Science*, 285:1569-1572, 1999.
Schwarze et al., *Trends Cell Biol.*, 10:290-295, 2000.
Sekido et al., *Biochimica. Biophysica. Acta*, 1378:F21-F59, 1998.
Sekido et al., *Oncogene*, 16:3151-3157, 1998.
Sekido et al., *Proc. Natl. Acad. Sci. USA*, 93:4120-4125, 1996.
Serrano et al., *Nature*, 366:704-707, 1993.
Serrano et al., *Science*, 267(5195):249-252, 1995.
Sestier et al., *Electrophoresis*, 19:1220-1226, 1998.
Simberg et al., *Human Gene Therapy*, 16:1087-96, 2005.
Simberg et al., *Proceedings of the National Academy of Sciences*, 104:932-6, 2007.
Spandidos et al., *Anticancer Res.*, 9(2):383-386, 1989.
Stayton et al., *J. Controlled Release*, 65:203-220, 2000.
Sun et al., *Biopolymers*, 60(1):61-75, 2001.
Swisher et al., *J Natl Cancer Inst.*, 91:763-71, 1999.
Templeton, *Nature Biotech.*, 15:647-652, 1997.
Templeton, *Nature Biotechnology*, 15:647-652, 1997.
Travali et al., *FASEB J.*, 4(14):3209-3214, 1990.
Tsujimoto and Croce, *Proc. Natl. Acad. Sci. USA*, 83(14):5214-5218, 1986.
Tsujimoto et al., *Science*, 228(4706):1440-1443, 1985.
Uno et al., *Cancer Research*, 64:2969-2976, 2004.
Uzawa et al., *Cancer Genet. Cytogenet.*, 107:125-131, 1998.
Virmani et al., *Genes Chrom Cancer*, 21:308-319, 1998.
Wang, *Oncogene*, 19(49):5643-5650, 2000.
Weinberg, *Science*, 254(5035):1138-1146, 1991.
Weinberg, *Science*, 254:1138-1146, 1991.
Wen and Van Etten, *Genes and Development*, 11:2456-2467, 1997.
West, *Methods in Molec. Biol.*, 238:113-122, 2004.
Wilhelm et al., *Biomaterials*, 24:1001-1011, 2003.
Wistuba et al., *Cancer Res.*, 57:3154-3158, 1997.

Wistuba et al., *Cancer Res.*, 59:1973-1979, 1999.
Wistuba et al., *Oncogene*, 18:643-650, 1999.
Woodring et al., *J. Cellular Science*, 116(Pt.13):2613-2626, 2003.
Zbar et al., *Nature*, 327:721-724, 1987.
Yang et al., *Gene Ther.*, 4:950-60, 1997.
Zhao, *Anti-Cancer Agents in Medicinal Chemistry*, 9:1018-1023, 2009.

What is claimed is:

1. A method for treating a human subject having a cancer, wherein it was determined that at least 10% of the pretreated cells of said cancer, having been obtained by biopsy from said subject, are apoptotic, the method comprising administering a TUSC2 therapy to the subject.

2. The method of claim 1, wherein the TUSC2 therapy comprises administration of a TUSC2 expression vector.

3. The method of claim 2, wherein the TUSC2 expression vector is plasmid DNA.

4. The method of claim 3, wherein the plasmid is pLJ143/KGB2/FUS1.

5. The method of claim 2, wherein the TUSC2 expression vector is provided in a liposome.

6. The method of claim 5, wherein the liposome is a DOTAP:cholesterol liposome.

7. The method of claim 6, wherein the DOTAP:cholesterol ratio is between about 1.5:1 and 1:1.5.

8. The method of claim 6, wherein the TUSC2 expression vector and DOTAP:cholesterol liposome are administered in a dose of from about 0.01 mg/kg to about 0.10 mg/kg.

9. The method of claim 1, wherein it was previously determined that at least 20% of the cells of said cancer are apoptotic.

10. The method of claim 1, further comprising administering at least a second anti-cancer therapy to the subject.

11. The method of claim 10, wherein the second anti-cancer therapy is chemotherapy, radiotherapy, gene therapy, surgery, hormonal therapy, anti-angiogenic therapy or cytokine therapy.

12. The method of claim 11, wherein the second anti-cancer therapy is an EGFR inhibitor.

13. The method of claim 1, wherein the cancer is a lung cancer.

14. The method of claim 13, wherein the lung cancer is a non-small cell lung cancer.

15. The method of claim 13, wherein the cancer is a metastatic lung cancer.

16. The method of claim 1, wherein the cancer is resistant to at least a first chemotherapy.

17. The method of claim 16, wherein the cancer is resistant to a platinum-based chemotherapy.

18. The method of claim 1, wherein the TUSC2 therapy comprises administration of a TUSC2 polypeptide.

19. The method of claim 18, wherein the TUSC2 polypeptide is myristoylated.

20. The method of claim 18, wherein the TUSC2 polypeptide is comprised in a nanoparticle.

21. The method of claim 20, wherein the nanoparticle is a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube.

* * * * *

UNITED STATES PATENT AND TRADEMARK OFFICE
CERTIFICATE OF CORRECTION

PATENT NO. : 9,675,663 B2
APPLICATION NO. : 14/480341
DATED : June 13, 2017
INVENTOR(S) : Jack Roth et al.

It is certified that error appears in the above-identified patent and that said Letters Patent is hereby corrected as shown below:

In the Specification

In Column 1, Lines 10-13, delete the paragraph and insert --This invention was made with government support under grant number CA070907, CA016672, and CA113450 awarded by the National Institutes of Health. The government has certain rights in the invention.-- therefor.

Signed and Sealed this
Twenty-fifth Day of September, 2018

Andrei Iancu
*Director of the United States Patent and Trademark Office*

```
                        SEQUENCE LISTING

<160> NUMBER OF SEQ ID NOS: 5

<210> SEQ ID NO 1
<211> LENGTH: 7936
<212> TYPE: DNA
<213> ORGANISM: Artificial Sequence
<220> FEATURE:
<223> OTHER INFORMATION: Plasmid vector

<400> SEQUENCE: 1
cgaaatcatc aataatatac cttattttgg attgaagcca atatgataat gctttagtag      60
ttattatatg gaataaaacc taacttcggt tatactatta gagggggtgg agtttgtgac     120
gtggcgcggg gcgtgggaac ggggcgggtg ctcccccacc tcaaacactg caccgcgccc     180
cgcacccttg ccccgcccac acgtagtagt gtggcggaag tgtgatgttg caagtgtggc     240
ggaacacatg tgcatcatca caccgccttc acactacaac gttcacaccg ccttgtgtac     300
taagcgacgg atgtggcaaa agtgacgttt ttggtgtgcg ccgtgtata attcgctgcc      360 tacaccgttt tcactgcaaa aaccacacgc ggccacatat cgggaagtga caattttcgc     420
gcggttttag gcggatgttg tagtaaattt gcccttcact gttaaaagcg cgccaaaatc     480
cgcctacaac atcatttaaa gggcgtaacc aagtaatatt tggccatttt cgcgggaaaa     540
ctgaataaga cccgcattgg ttcattataa accgtaaaaa gcgccctttt gacttattct     600
ggaagtgaaa tctgaataat tctgtgttac tcatagcgcg taatatttgt ccttcacttt     660
agacttatta agacacaatg agtatcgcgc attataaaca ctagggccgc ggggactttg     720
accgtttacg tggagactcg cccaggtgtt gatcccggcg ccctgaaac tggcaaatgc      780 acctctgagc gggtccacaa tttctcaggt gttttccgcg ttccgggtca agttggcgt     840 tttattatta aaagagtcca caaaaggcgc aaggcccagt ttcaaccgca aaataataat     900
tagtcagctc tagagcccga cattgattat tgactagtta ttaatagtaa atcagtcgag     960
atctcgggct gtaactaata actgatcaat aattatcatt tcaattacgg ggtcattagt    1020
tcatagccca tatatggagt tccgcgttac agttaatgcc ccagtaatca agtatcgggt    1080 atataccctca aggcgcaatg ataacttacg gtaaatggcc cgcctggctg accgcccaac    1140
gacccccgcc tattgaatgc catttaccgg gcggaccgac tggcgggttg ctggggcgg     1200 cattgacgtc aataatgacg tatgttccca tagtaacgcc aatagggact gtaactgcag    1260
ttattactgc atacaagggt atcattgcgg ttatccctga ttccattgac gtcaatgggt    1320
ggagtattta cggtaaactg cccacttggc aaggtaactg cagttaccca cctcataaat    1380
gccatttgac gggtgaaccg agtacatcaa gtgtatcata tgccaagtac gcccctatt     1440 gacgtcaatg tcatgtagtt cacatagtat acggttcatg cggggataa ctgcagttac      1500 acggtaaatg gcccgcctgg cattatgccc agtacatgac cttatgggac tgccatttac    1560
cgggcggacc gtaatacggg tcatgtactg gaataccctg tttcctactt ggcagtacat    1620
ctacgtatta gtcatcgcta ttaccatggt aaaggatgaa ccgtcatgta gatgcataat    1680
cagtagcgat aatggtacca gatgcggttt tggcagtaca tcaatgggcg tggatagcgg    1740
tttgactcac ctacgccaaa accgtcatgt agttaccgc acctatcgcc aaactgagtg     1800
ggggatttcc aagtctccac cccattgacg tcaatgggag tttgttttgg cccctaaagg    1860
```

```
ttcagaggtg gggtaactgc agttaccctc aaacaaaacc caccaaaatc aacgggactt    1920
tccaaaatgt cgtaacaact ccgccccatt gtggttttag ttgccctgaa aggttttaca    1980
gcattgttga ggcggggtaa gacgcaaatg ggcggtaggc gtgtacggtg ggaggtctat    2040
ataagcagag ctgcgtttac cgccatccg cacatgccac cctccagata tattcgtctc    2100
ctcgtttagt gaaccgtcag atcgcctgga gacgccatcc acgctgtttt gagcaaatca    2160
cttggcagtc tagcggacct ctgcggtagg tgcgacaaaa gacctccata gaagacaccg    2220
ggaccgatcc agcctccgcg gccgggaacg ctggaggtat cttctgtggc cctggctagg    2280
tcggaggcgc cggcccttgc gtgcattgga acggacctgc agcccaagct tggtaccgag    2340
ctcggatcca cacgtaacct tgcctggacg tcgggttcga accatggctc gagcctaggt    2400
ctagtccagt gtggtggaat tcggcttgac atgggcgcca gcgggtccaa gatcaggtca    2460 caccaccta agccgaactg taccgcggt cgcccaggtt agctcggggc ctgtggccct    2520
tcgcctcggc ggccggaggc ggcggctcag tcgagcccg gacaccggga agcggagccg    2580
ccggcctccg ccgccgagtc aggcagcagg agctgagcaa gctttggtgc ggcctcgggg    2640
ccgagctgtg tccgtcgtcc tcgactcgtt cgaaaccacg ccggagcccc ggctcgacac    2700
ccccccttcg tattcacgcg ccgcggctct atgttctatg atgaggatgg ggggggaagc    2760
ataagtgcgc ggcgccgaga tacaagatac tactcctacc ggatctggct cacgagttct    2820
atgaggagac aatcgtcacc aagaacgggc cctagaccga gtgctcaaga tactcctctg    2880
ttagcagtgg ttcttgcccg agaagcgggc caagctgagg cgagtgcata agaatctgat    2940
tcctcagggc tcttcgcccg gttcgactcc gctcacgtat tcttagacta aggagtcccg    3000
atcgtgaagc tggatcaccc ccgcatccac gtggatttcc ctgtgatcct tagcacttcg    3060
acctagtggg ggcgtaggtg cacctaaagg gacactagga ctatgaggtg tgaccctgga    3120
agccgaattc tgcagatatc cagcacaagt gatactccac actgggacct tcggcttaag    3180
acgtctatag gtcgtgttca ggcggccgct cgagtctaga gggcccgttt aaacccgctg    3240
atcagcctcg ccgccggcga gctcagatct cccgggcaaa tttgggcgac tagtcggagc    3300
actgtgcctt ctagttgcca gccatctgtt gtttgccct cccccgtgcc tgacacggaa    3360
gatcaacggt cggtagacaa caaacgggga gggggcacgg ttccttgacc ctggaaggtg    3420
ccactcccac tgtcctttcc taataaaatg aaggaactgg accttccac ggtgagggtg    3480 acaggaaagg attattttac aggaaattgc atcgcattgt ctgagtaggt gtcattctat    3540 tctgggggt tcctttaacg tagcgtaaca gactcatcca cagtaagata agacccccca    3600
ggggtggggc aggacagcaa ggggaggat tgggaagaca atagcaggca ccccaccccg    3660
tcctgtcgtt ccccctccta acccttctgt tatcgtccgt tgctgggat gcggtgggct    3720 ctatggcttc tactgggcgg ttttatggac acgacccta cgccacccga gataccgaag    3780
atgacccgcc aaaatacctg agcaagcgaa ccggaattgc cagctgggc gccctctggt    3840 aaggttggga tcgttcgctt ggccttaacg gtcgacccg cgggagacca ttccaaccct    3900
agccctgcaa agtaaactgg atggctttct cgccgccaag gatctgatgg tcgggacgtt    3960
tcatttgacc taccgaaaga gcggcggttc ctagactacc cgcaggggat caagctctga    4020
tcaagagaca ggatgaggat cgtttcgcat gcgtccccta gttcgagact agttctctgt    4080
cctactccta gcaaagcgta gattgaacaa gatggattgc acgcaggttc tccggccgct    4140
tgggtggaga ctaacttgtt ctacctaacg tgcgtccaag aggccggcga acccacctct    4200
```

```
ggctattcgg ctatgactgg gcacaacaga caatcggctg ctctgatgcc ccgataagcc    4260
gatactgacc cgtgttgtct gttagccgac gagactacgg gccgtgttcc ggctgtcagc    4320 gcagggcgc ccggttctt ttgtcaagac cggcacaagg ccgacagtcg cgtccccgcg     4380
ggccaagaaa aacagttctg cgacctgtcc ggtgccctga atgaactgca agacgaggca    4440
gcgcggctat gctggacagg ccacgggact tacttgacgt tctgctccgt cgcgccgata    4500
cgtggctggc cacgacgggc gttccttgcg cagctgtgct cgacgttgtc gcaccgaccg    4560
gtgctgcccg caaggaacgc gtcgacacga gctgcaacag actgaagcgg aagggactg    4620 gctgctattg ggcgaagtgc cggggcagga tgacttcgcc cttccctgac cgacgataac    4680
ccgcttcacg gccccgtcct tctcctgtca tctcaccttg ctcctgccga aaagtatcc    4740 atcatggctg agaggacagt agagtggaac gaggacggct cttttcatagg tagtaccgac    4800 atgcaatgcg gcggctgcat acgcttgatc cggctacctg cccattcgac tacgttacgc    4860
cgccgacgta tgcgaactag gccgatggac gggtaagctg caccaagcga acatcgcat    4920 cgagcgagca cgtactcgga tggaagccgg gtggttcgct ttgtagcgta gctcgctcgt    4980
gcatgagcct accttcggcc tcttgtcgat caggatgatc tggacgaaga gcatcagggg    5040
ctcgcgccag agaacagcta gtcctactag acctgcttct cgtagtcccc gagcgcggtc    5100
ccgaactgtt cgccaggctc aaggcgagca tgcccgacgg cgaggatctc ggcttgacaa    5160
gcggtccgag ttccgctcgt acgggctgcc gctcctagag gtcgtgaccc atggcgatgc    5220
ctgcttgccg aatatcatgg tggaaaatgg cagcactggg taccgctacg gacgaacggc    5280
ttatagtacc accttttacc ccgcttttct ggattcatcg actgtggccg gctgggtgtg    5340
gcggaccgct ggcgaaaaga cctaagtagc tgacaccggc cgacccacac cgcctggcga    5400
atcaggacat agcgttggct acccgtgata ttgctgaaga gcttggcggc tagtcctgta    5460
tcgcaaccga tgggcactat aacgacttct cgaaccgccg gaatgggctg accgcttcct    5520
cgtgctttac ggtatcgccg ctcccgattc cttacccgac tggcgaagga gcacgaaatg    5580
ccatagcggc gagggctaag gcagcgcatc gccttctatc gccttcttga cgagttcttc    5640
tgaattatta cgtcgcgtag cggaagatag cggaagaact gctcaagaag acttaataat    5700
acgcttacaa tttcctgatg cggtattttc tccttacgca tctgtgcggt tgcgaatgtt    5760
aaaggactac gccataaaag aggaatgcgt agacacgcca atttcacacc gcatacaggt    5820 ggcactttt ggggaaatgt gcgcggaacc taaagtgtgg cgtatgtcca ccgtgaaaag    5880
cccctttaca cgcgccttgg cctatttgtt tattttctta aatacattca aatatgtatc    5940
cgcttaagaa ggataaacaa ataaaaagat ttatgtaagt ttatacatag gcgaattctt    6000
catgtgagca aaaggccagc aaaaggccag gaaccgtaaa aaggccgcgt gtacactcgt    6060
tttccggtcg tttccggtc cttggcattt ttccggcgca tgctggcgtt tttccatagg    6120
ctccgccccc ctgacgagca tcacaaaaat acgaccgcaa aaggtatcc gaggcggggg    6180 gactgctcgt agtgttttta cgacgctcaa gtcagaggtg gcgaacccg acaggactat    6240 aaagatacca gctgcgagtt cagtctccac cgctttgggc tgtcctgata tttctatggt    6300
ggcgtttccc cctggaagct ccctcgtgcg ctctcctgtt ccgaccctgc cgcaaaggg    6360 ggaccttcga gggagcacgc gagaggacaa ggctgggacg cgcttaccgg atacctgtcc    6420
gcctttctcc cttcgggaag cgtggcgctt gcgaatggcc tatggacagg cggaaagagg    6480
gaagcccttc gcaccgcgaa tctcatagct cacgctgtag gtatctcagt tcggtgtagg    6540
tcgttcgctc agagtatcga gtcgacatc catagagtca agccacatcc agcaagcgag    6600
```

```
caagctgggc tgtgtgcacg aaccccccgt tcagcccgac cgctgcgcct gttcgacccg    6660
acacacgtgc ttggggggca agtcgggctg gcgacgcgga tatccggtaa ctatcgtctt    6720
gagtccaacc cggtaagaca cgacttatcg ataggccatt gatagcagaa ctcaggttgg    6780
gccattctgt gctgaatagc ccactggcag cagccactgg taacaggatt agcagagcga    6840
ggtatgtagg ggtgaccgtc gtcggtgacc attgtcctaa tcgtctcgct ccatacatcc    6900
cggtgctaca gagttcttga agtggtggcc taactacggc tacactagaa gccacgatgt    6960
ctcaagaact tcaccaccgg attgatgccg atgtgatctt gaacagtatt tggtatctgc    7020
gctctgctga agccagttac cttcggaaaa cttgtcataa accatagacg cgagacgact    7080
tcggtcaatg gaagcctttt agagttggta gctcttgatc cggcaaacaa accaccgctg    7140
gtagcggtgg tctcaaccat cgagaactag gccgtttgtt tggtggcgac catcgccacc    7200 ttttttttgtt tgcaagcagc agattacgcg cagaaaaaaa ggatctcaag aaaaaaacaa    7260
acgttcgtcg tctaatgcgc gtctttttttt cctagagttc aagatccttt gatcttttct    7320
acggggtctg acgctcagtg gaacgaaaac ttctaggaaa ctagaaaaga tgccccagac    7380
tgcgagtcac cttgcttttg tcacgttaag ggattttggt catggctagt taatcatgag    7440
attatcaaaa agtgcaattc cctaaaacca gtaccgatca attagtactc taatagtttt    7500
aggatcttca cctagatcct tttaaattaa aaatgaagtt ttaaatcaat tcctagaagt    7560
ggatctagga aaatttaatt tttacttcaa aatttagtta ctaaagtata tatgagtaaa    7620
cttggtctga cagttaccaa tgcttaatca gatttcatat atactcattt gaaccagact    7680
gtcaatggtt acgaattagt gtgaggcacc tatctcagcg atctgtctat ttcgttcatc    7740
catagttgcc cactccgtgg atagagtcgc tagacagata aagcaagtag gtatcaacgg    7800
tgactccccg tcgtgtagat aactacgata cgggagggct taccatctgg actgaggggc    7860
agcacatcta ttgatgctat gccctcccga atggtagacc ccccagtgct gcaatgatgg    7920
ggtcacgacg ttacta                                                    7936
```

<210> SEQ ID NO 2
<211> LENGTH: 17
<212> TYPE: PRT
<213> ORGANISM: Homo sapiens

<400> SEQUENCE: 2

Gly Ala Ser Gly Ser Lys Ala Arg Gly Leu Trp Pro Phe Ala Ser Ala
1               5                   10                  15

Ala

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
ggacctgcag cccaagct                                                  18

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

```
<400> SEQUENCE: 4
gcccatgtca agccgaatt                                                19

<210> SEQ ID NO 5
<211> LENGTH: 27
<212> TYPE: DNA
<213> ORGANISM: Artificial Sequence
<220> FEATURE:
<223> OTHER INFORMATION: Synthetic primer

<400> SEQUENCE: 5
cgagctcgga tccactagtc cagtgtg                                       27
```